United States Patent
Qi

(10) Patent No.: US 9,271,932 B2
(45) Date of Patent: Mar. 1, 2016

(54) FUSOGENIC PROPERTIES OF SAPOSIN C AND RELATED PROTEINS AND PEPTIDES FOR APPLICATION TO TRANSMEMBRANE DRUG DELIVERY SYSTEMS

(75) Inventor: Xiaoyang Qi, Loveland, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 1291 days.

(21) Appl. No.: 11/741,323

(22) Filed: Apr. 27, 2007

(65) Prior Publication Data

US 2009/0142267 A1 Jun. 4, 2009

Related U.S. Application Data

(60) Provisional application No. 60/745,969, filed on Apr. 28, 2006.

(51) Int. Cl.
| | |
|---|---|
| *A61K 38/00* | (2006.01) |
| *A61P 35/00* | (2006.01) |
| *C08K 3/34* | (2006.01) |
| *A61K 9/127* | (2006.01) |
| *A61K 9/00* | (2006.01) |
| *A61K 38/18* | (2006.01) |

(52) U.S. Cl.
CPC ............... *A61K 9/127* (2013.01); *A61K 9/006* (2013.01); *A61K 9/007* (2013.01); *A61K 9/0014* (2013.01); *A61K 9/0043* (2013.01); *A61K 38/18* (2013.01)

(58) Field of Classification Search
None
See application file for complete search history.

(56) References Cited

U.S. PATENT DOCUMENTS

| | | | |
|---|---|---|---|
| 887,290 | A | 5/1908 | Taylor |
| 3,472,931 | A | 10/1969 | Stoughton |
| 4,006,218 | A | 2/1977 | Sipos |
| 4,162,282 | A | 7/1979 | Fulwyler et al. |
| 4,310,505 | A | 1/1982 | Baldeschwieler et al. |
| 4,533,254 | A | 8/1985 | Cook et al. |
| 4,588,580 | A | 5/1986 | Gale et al. |
| 4,645,502 | A | 2/1987 | Gale et al. |
| 4,684,479 | A | 8/1987 | D'Arrigo |
| 4,728,575 | A | 3/1988 | Gamble et al. |
| 4,728,578 | A | 3/1988 | Higgins et al. |
| 4,737,323 | A | 4/1988 | Martin et al. |
| 4,788,062 | A | 11/1988 | Gale et al. |
| 4,806,356 | A | 2/1989 | Shaw |
| 4,816,258 | A | 3/1989 | Nedberge et al. |
| 4,900,555 | A | 2/1990 | Cheng et al. |
| 4,904,475 | A | 2/1990 | Gale et al. |
| 4,921,706 | A * | 5/1990 | Roberts et al. ............... 424/450 |
| 4,927,408 | A | 5/1990 | Haak et al. |
| 4,940,587 | A | 7/1990 | Jenkins et al. |
| 5,053,227 | A | 10/1991 | Chiang et al. |
| 5,149,319 | A | 9/1992 | Unger |
| 5,154,924 | A | 10/1992 | Friden |
| 5,176,996 | A | 1/1993 | Hogan et al. |
| 5,182,107 | A | 1/1993 | Friden |
| 5,205,290 | A | 4/1993 | Unger |
| 5,215,680 | A | 6/1993 | D'Arrigo |
| 5,312,617 | A | 5/1994 | Unger et al. |
| 5,376,380 | A * | 12/1994 | Kikuchi et al. ............... 424/450 |
| 5,527,527 | A | 6/1996 | Friden |
| 5,668,648 | A | 9/1997 | Saito et al. |
| 5,672,683 | A | 9/1997 | Friden et al. |
| 5,707,649 | A * | 1/1998 | Inokuchi et al. ............. 424/450 |
| 5,707,804 | A | 1/1998 | Mathies et al. |
| 5,716,780 | A | 2/1998 | Edwards et al. |
| 5,728,528 | A | 3/1998 | Mathies et al. |
| 5,766,626 | A | 6/1998 | Gross |
| 5,833,988 | A | 11/1998 | Friden |
| 5,853,992 | A | 12/1998 | Glazer et al. |
| 5,869,255 | A | 2/1999 | Mathies et al. |
| 5,925,517 | A | 7/1999 | Tyagi et al. |
| 5,977,307 | A | 11/1999 | Friden et al. |

(Continued)

FOREIGN PATENT DOCUMENTS

| | | |
|---|---|---|
| GB | 2193095 A | 3/1988 |
| JP | 04-103527 | 4/1992 |

(Continued)

OTHER PUBLICATIONS

Chu et al. abstract presented at 7th International Conference on Neuroprotective agents, Nov. 14-19, 2004.*
Burgess et al., J of Cell Biol., 111:2129-2138, 1990.*
Lazar et al. Molecular and Cellular Biology, 8:1247-1252, 1988.*
Bowie et al. Science, 247:1306-1310, 1990.*
Skolnick, et al. Trends in Biotech. 18, 34-39, 2000.*
Ngo et al., in The Protein Folding Problem and Tertiary Structure Prediction, 1994, Merz, et al., (ed.), Birkhauser, Boston, MA, pp. 433 and 492-495.*
Ames, B.N. et al., "Illicit Transport: the Oligopeptide Permease" Proc. Natl. Acad. Sci. USA, vol. 70(2) (Feb. 1973) pp. 456-458.
Berent, S.L., et al., "Mechanism of Activation of Glucocerebrosidase by CO-β-Glucosidase (Glucosidase Activator Protein)," Biochimica et Biophysica Acta, vol. 664, (1981) pp. 572-582.

(Continued)

*Primary Examiner* — Hong Sang
(74) *Attorney, Agent, or Firm* — Hahn Loeser & Parks, LLP

(57) ABSTRACT

The present invention comprises a method for delivering pharmaceutical and/or imaging agents within and/or through the dermal, mucosal and other cellular membranes, and across the blood-brain barrier, utilizing a fusogenic protein. The fusogenic protein is associated with a phospholipid membrane, such as a liposome. The liposome may include dioleoylphosphatidylserine, a negatively charged long-chain lipid. Alternatively, the liposome is comprised of a mixture of negatively charged long-chain lipids, neutral long-chain lipids, and neutral short-chain lipids. Preferred fusogenic proteins include saposin C and other proteins, polypeptides and peptide analogs derived from saposin C. The active agent contained within the liposome may comprise biomolecules and/or organic molecules. This technology can be used for both cosmetic and medicinal applications in which the objective is delivery of the active agent within and/or beneath biological membranes or across the blood-brain barrier and neuronal membranes.

15 Claims, 9 Drawing Sheets

(56) References Cited

U.S. PATENT DOCUMENTS

| | | | |
|---|---|---|---|
| 6,001,311 | A | 12/1999 | Brennan |
| 6,037,130 | A | 3/2000 | Tyagi et al. |
| 6,099,857 | A | 8/2000 | Gross |
| 6,569,451 | B1 | 5/2003 | Li et al. |
| 6,787,132 | B1* | 9/2004 | Gabizon et al. ............... 424/85.2 |
| 6,872,406 | B2* | 3/2005 | Qi ................................. 424/450 |
| 6,962,686 | B2 | 11/2005 | Kayyem et al. |
| 2002/0012698 | A1 | 1/2002 | Bauerlein et al. |
| 2003/0095999 | A1 | 5/2003 | Qi |
| 2004/0229799 | A1* | 11/2004 | Qi ................................. 514/12 |
| 2005/0100591 | A1 | 5/2005 | Qi |

FOREIGN PATENT DOCUMENTS

| | | |
|---|---|---|
| JP | 2009-535348 | 10/2009 |
| WO | WO 86/00238 | 1/1986 |
| WO | WO 89/02439 | 3/1989 |
| WO | WO 90/04943 | 5/1990 |
| WO | WO 95/06731 | 3/1995 |
| WO | WO 95/11910 | 5/1995 |
| WO | WO 98/40049 | 9/1998 |
| WO | WO 99/52505 | 10/1999 |
| WO | WO 99/54459 | 10/1999 |
| WO | WO00/12553 | 3/2000 |
| WO | WO 2007/127439 | 11/2007 |
| WO | WO 2008/051818 | 5/2008 |

OTHER PUBLICATIONS

Burchiel, S.W., et al., "Expression and Detection of Human Tumor-Associated Antigens," Radioimmunoimaging and Radioimmunotherapy, Elsevier, New York, New York (1983) pp. 13-23.

Campana, W.M., et al., "Introduction of MAPK Phosphorylation by Prosaposin and Prosaptide in PC12 Cells," Biochem. Biophys. Res. Commun., vol. 229 (1996) pp. 706-712.

Fujibayashi, S., et al., Assignment of the Gene for Human Sphingolipid Activator Protein-2 (SAP-2) to Chromosome 10, vol. 37 (1985) pp. 741-748.

Furst, et al., Activator proteins and topology of lysosomal sphingolipid catabolism, Ciochimica et Biophysica Acta, vol. 1126 (1992) pp. 1-16.

Grabowski, G., A., et al., "Acid β-Glucosidase: Enzymology and Molecular Biology of Gaucher Disease," Crit. Rev. Biochem. Mol. Biol., vol. 25 (1990) pp. 385-414.

Greenberg, P. et al., "Human acid β-glucosidase: use of sphingosyl and N-alkylglucosylamine inhibitors to investigate the properties of the active site,"Biochimica et. Biophysica Acta, vol. 1039 (1990) pp. 12-20.

Harzer, K., et al., "Saposins (sap) A and C activate the degradation of galactosylceramide in living cells," FEBS Letters, vol. 417 (1997) pp. 270-274.

Hiraiwa, M., et al., "Prosaposin Receptor: Evidence for a G-Protein-Associated Receptor," Biochem. Biophys. Res. Commun., vol. 240 (1997) Article No. RC977673, pp. 415-418.

Hiraiwa, M., et al., "Binding and transport of gangliosides by prosaposin," Proc. Natl. Acad. Sci., USA, vol. 89 (Dec. 1992) pp. 11254-11258.

Kawabata, K., et al., "Effect of second-harmonic superimposition on efficient induction of sonochemical effect," Ultrasonics Sonochemistry, vol. 3 (1996) pp. 1-5.

Kean, D.M., et al., "Magnetic Resonance Imaging: Principles and Applications", 1986, Williams and Wilkins, Baltimore.

Kishimoto, Y., et al., "Saposins: structure, function, distribution, and molecular genetics," J. Lipid. Res., vol. 33 (1992) pp. 1255-1267.

Klien, A., et al., "Sphingolipid Activator Protein D (sap-D) Stimulates the Lysosomal Degradation of Ceramide in Vivo," Biochem. Biophys. Res. Commun., vol. 200(3) (May 16, 1994) pp. 1440-1448.

Li, H., et al., "MR and Fluorescent Imaging of Low-Density Lipoprotein Receptors", Acad. Radiol., vol. 11 (2004) pp. 1251-1259.

Madden, et al., "The accumulation of drugs within large unilamellar vesicles exhibiting a proton gradient: a survey," Chemistry and Physics of Lipids, vol. 53 (1990) pp. 37-46.

Magerstadt, M., "Antibody Conjugates and Malignant Disease", 1991, CRC Press, Boca Raton, Florida.

Nakano, T., et al., "Structure of Full-Length cDNA Coding for Sulfatide Activator, a Co-β-Glusodidase and Two Other Homologous Proteins: Two Alternate Forms of the Sulfatide Activator," J. Biochem., vol. 105 (1989) pp. 152-154.

O'Brien, et al., "Coding of Two Sphingolipid Activator Proteins (SAP-1 and SAP-2) by Same Genetic Locus," Science, vol. 241 (1988) pp. 1098-1101.

O'Brien, J.S., et al., "Identification of the neurotrophic factor sequence of prosaposin,"FASEB J., vol. 9 (May 1995) pp. 681-685.

Qi, X, et al., "Functional Organization of Saposin C," J. Biol. Chem, vol. 271 (1996) pp. 6874-6880.

Qi, X., et al., "Conformational and Amino Acid Residue Requirements for the Saposin C Neuritogenic Effect," Biochemistry, vol. 38 (1999) pp. 6284-6291.

Qi, X., et al., "Fusogenic domain and lysines in saposin C," Arch. Biochem. Biophys., vol. 424 (2004) pp. 210-218.

Qi, X., et al., "Acid β-Glucosidase: Intrinsic Fluorescence and Conformational Changes Induced by Phospholipids and Saposin C," Biochemistry, vol. 37 (1998) pp. 11544-11554.

Qi, X., et al., "Differential Membrane Interactions of Saposins A and C," J. Biol. Chem., vol. 276(29) (2001) pp. 27010-27017.

Reiner, O.J., et al., "Human Sphingolipid Activator Protein-1 and Sphingolipid Activator Protein-2 are Encoded by the Same Gene," J. Mol. Neurosci., vol. 1, (1989) pp. 225-233.

Rorman, E.G., et al., "Molecular Cloning of a Human Co-β-glucosidase cDNA: Evidence That Four Sphingolipid Hydrolase Activator Proteins Are Encoded by Single Genes in Humans and Rats," Genomics, 1989, vol. 5 (May 18, 1989) pp. 486-492.

Russell-Jones, G.J. et al., "Vitamin B12: A Novel Carrier for Orally Presented Antigens," Proc. Int. Symp. Cont. Rel. Bioact. Mater., vol. 15 (1988) p. 142-143.

Schnabel, D., et al., "Simultaneous Deficiency of Sphingolipid Activator Proteins 1 and 2 IS Caused by a Mutation in the Initiation Codon of Their Common Gene," J. Biol. Chem., vol. 267 (Feb. 15, 1992) pp. 3312-3315.

Vaccaro, A.M., et al., "pH-dependent Conformational Properties of Saposins and Their Interactions with Phospholipid Membranes," J. Biol., Chem., vol. 270(51) (Dec. 22, 1995) pp. 30576-30580.

Vaccaro, A.M., et al., "Saposin C induces pH-dependent destabilization and fusion of phosphatidylserine-containing vesicles," FEBS Lett., vol. 349 (1994) pp. 181-186.

Vaccaro, A.M., et al., "Structural Analysis of Saposin C and B," J. Biol. Chem., vol. 270(17) (Apr. 28, 1995) pp. 9953-9960.

Wang, Y., et al., "Phospholipid vesicle fusion induced by saposin C," Arc. Biochem. Biophys., vol. 415 (2003) pp. 43-53.

You, H. X., et al., "Phospholipid Membrane Interactions of Saposin C: in Situ Atomic Force Microscopic Study," Biophys. J., vol. 84 (Mar. 2003) pp. 2043-2057.

You, H. X., et al., "Phospholipid membrane restructuring induced by saposin C: a topographic study using atomic force microscopy," FEBS Lett., vol. 503 (2001) pp. 97-102.

International Search Report and Written Opinion dated Jul. 11, 2008 for Application No. PCT/US2007/081880.

Pardridge, Brain Drug Targeting: The future of brain drug development, 2001, pp. 183-184.

Ritter et al., "Ganglioside antigens expressed by human cancer cells," Semin Cancer Biol., 1991; 2:401-409.

Hoon et al., "Aberrant expression of gangliosides in human renal cell carcinomas," J. Urol. 1993; 150:2013-2018.

Welch et al., eds., "Blood-Brain Barrier Transport Mechanisms," In Primer on Cerebrovascular Diseases, 1997, pp. 21-25.

Office Action, mailed in counterpart Canadian Patent Application No. 2,650,691, dated Feb. 11, 2014, 2 pgs. (received Mar. 14, 2014).

Basu et al., "Degradation of cationized low density lipoprotein and regulation of cholesterol metabolism in homozygous familial hypercholesterolemia fibroblasts," Proc. Natl. Acad. Sci. USA., Sep. 1976; pp. 3178-3182, vol. 73(9).

(56) References Cited

OTHER PUBLICATIONS

Bock et al., "Selection of single-stranded DNA molecules that bind and inhibit human thrombin," Nature, Feb. 6, 1992, pp. 564-566, vol. 355(6360) [abstract only].
Bogdanov et al., Trapping of dextran-coated colloids in liposomes by transient binding to aminophospholipid: preparation of ferrosomes, Biochim Biophys Acta., Jul. 13, 1994, pp. 212-218, vol. 1193(1) [abstract only].
Brennan et al., "Two-dimensional parallel array technology as a new approach to automated combinatorial solid-phase organic synthesis," Biotechnol. Bioeng., Winter 1998, pp. 33-45, vol. 61(1) [abstract only].
Broder et al., "Antiretroviral Therapy in AIDS," Ann. Intern. Med., 1990, pp. 604-618, vol. 113.
Brody et al., "Aptamers as therapeutic and diagnostic agents," J. Biotechnol., Mar. 2000, pp. 5-13, vol. 74(1) [abstract only].
Burkhardt et al., "Accumulation of sphingolipids in SAP-precursor (prosaposin)-deficient fibroblasts occurs as intralysosomal membrane structures and can be completely reversed by treatment with human SAP-precursor," Eur. J. Cell Biol., May 1997, vol. 73(1), pp. 10-18 [abstract only].
Campbell et al.,"Oligodeoxynucleoside phosphorothioate stability in subcellular extracts, culture media, sera and cerebrospinal fluid," J. Biochem. Biophys. Methods, Mar. 1990, pp. 259-267, vol. 20(3) [abstract only].
Caplen et al., "Specific inhibition of gene expression by small double-stranded RNAs in invertebrate and vertebrate systems," Proc. Natl. Acad. Sci. USA, Aug. 14, 2001, pp. 9742-9747, vol. 98(17).
Cheng et al., "The production and evaluation of contrast-carrying liposomes made with an automatic high-pressure system," Invest Radiol., Jan. 1987, pp. 47-55, vol. 22(1) [abstract only].
Chiang et al., "Antisense oligonucleotides inhibit intercellular adhesion molecule 1 expression by two distinct mechanisms," J. Biol. Chem., Sep. 25, 1991, pp. 18162-18171, vol. 266(27).
Ch'ng et al., "Antisense RNA complementary to 3' coding and noncoding sequences of creatine kinase is a potent inhibitor of translation in vivo," Proc. Natl. Acad. Sci. USA, Dec. 1989, pp. 10006-10010, vol. 86(24).
Christomanou et al., "Activtor protein deficient Gaucher's disease. A second patient with the newly identified lipid storage disorder.," Klin. Wochenschr., Oct. 2, 1989, vol. 67(19), pp. 999-1003 [abstract only].
Christomanou et al., "Immunochemical characterization of two activator proteins stimulating enzymic sphingomyelin degradation in vitro. Absence of one of them in a human Gaucher disease variant," Biol. Chem. Hoppe Seyler, Sep. 1986, vol. 367(9), pp. 879-890 [abstract only].
Chu et al., " Saposin C-LBPA interaction in late-endosomes/lysosomes," Exp. Cell Res., Feb. 15, 2005, pp. 300-307, vol. 303(2) [abstract only].
Cload et al., "Polyether Tethered Oligonucleotide Probes," J. Am. Chem. Soc., 1991, pp. 6324-6326, vol. 113 (16) [1st page only].
Cole-Strauss et al., "Correction of the mutation responsible for sickle cell anemia by an RNA-DNA oligonucleotide," Science, Sep. 6, 1996, pp. 1386-1389, vol. 273(5280) [abstract only].
Dubertret et al., "In vivo imaging of quantum dots encapsulated in phospholipid micelles," Science, Nov. 29, 2002, pp. 1759-1762, vol. 298(5599) [abstract only].
Durand et al., "Circular dichroism studies of an oligodeoxyribonucleotide containing a hairpin loop made of a hexaethylene glycol chain: conformation and stability," Nucleic Acids Res., Nov. 11, 1990, pp. 6353-6359, vol. 18(21).
Ellington et al., "In vitro selection of RNA molecules that bind specific ligands," Nature, Aug. 30, 1990, pp. 818-822, vol. 346(6287) [abstract only].
Ferentz et al., "Disulfide-crosslinked oligonucleotides," J. Am. Chem. Soc., May 1991, pp. 4000-4002, vol. 113 (10) [1st page only].
Forster et al., "External guide sequences for an RNA enzyme," Science, Aug. 17, 1990, pp. 783-786, vol. 249(4970) [abstract only].
Fritzsch et al., "Diffusion and imaging properties of three new lipophilic tracers, NeuroVue™ Maroon, NeuroVue™ Red and NeuroVue™ Green and their use for double and triple labeling of neuronal profile," Brain Res Bull., Aug. 15, 2005, pp. 249-258, vol. 66(3).
Froehler et al., "Phosphoramidate analogues of DNA: synthesis and thermal stability of heteroduplexes," Nucleic Acids Res., Jun. 10, 1988, pp. 4831-4839, vol. 16(11).
Fujita et al., "Targeted disruption of the mouse sphingolipid activator protein gene: a complex phenotype, including severe leukodystrophy and wide-spread storage of multiple sphingolipids," Hum. Mol. Genet., Jun. 1996, vol. 5(6), pp. 711-725.
Ginty et al., "Retrograde neurotrophin signaling: Trk-ing along the ax," Curr. Opin. Neurobiol., Jun. 2002, vol. 12(3), pp. 268-274 [abstract only].
Glickman et al., "A comparison of ALPHAScreen, TR-FRET, and TRF as assay methods for FXR nuclear receptors," J Biomol Screen., Feb. 2002, pp. 3-10, vol. 7(1).
Gold et al., "Diversity of oligonucleotide functions," Annu. Rev. Biochem., 1995, pp. 763-797, vol. 64 [abstract only].
Guerrier-Takada et al., "Phenotypic conversion of drug-resistant bacteria to drug sensitivity," Proc. Natl. Acad. Sci. USA, Aug. 5, 1997, pp. 8468-8472, vol. 94(16).
Harzer et al., "Sphingolipid activator protein deficiency in a 16-week-old atypical Gaucher disease patient and his fetal sibling: biochemical signs of combined sphingolipidoses," Eur. J. Pediatr., Oct. 1989, vol. 149(1), pp. 31-39 [abstract only].
Heye et al., "Assessment of blood-brain barrier disruption using dynamic contrast-enhanced MRI. A systematic review," NeuroImage: Clinical, 2014, pp. 262-274, vol. 6.
Honig et al., "DiI and diO: versatile fluorescent dyes for neuronal labelling and pathway tracing," Trends Neurosci., Sep. 1989, pp. 333-335 and 340-341, vol. 12(9) [abstract only].
Hope et al., "Production of large unilamellar vesicles by a rapid extrusion procedure: characterization of size distribution, trapped volume and ability to maintain a membrane potential," Biochim. Biophys. Acta., Jan. 10, 1985, pp. 55-65, vol. 812(1) [abstract only].
Hulková et al., "A novel mutation in the coding region of the prosaposin gene leads to a complete deficiency of prosaposin and saposins, and is associated with a complex sphingolipidosis dominated by lactosylceramide accumulation," Hum. Mol. Genet., Apr. 15, 2001, vol. 10(9), pp. 927-940.
Jaiswal et al., "Long-term multiple color imaging of live cells using quantum dot bioconjugates," Nature Biotechnology, Jan. 2003, pp. 47-51, vol. 21(1).
Jayasena, "Aptamers: an emerging class of molecules that rival antibodies in diagnostics," Clin. Chem., Sep. 1999, pp. 1628-1650, vol. 45(9).
Katzmann et al., "Receptor downregulation and multivesicular-body sorting," Nat. Rev. Mol. Cell Biol., Dec. 2002, vol. 3(12), pp. 893-905 [abstract only].
Kotani et al., "A hydrophilic peptide comprising 18 amino acid residues of the prosaposin sequence has neurotrophic activity in vitro and in vivo," J. Neurochem., May 1996, vol. 66(5), pp. 2197-2200 [abstract only].
Kotani et al., "Prosaposin facilitates sciatic nerve regeneration in vivo," J. Neurochem., May 1996, vol. 66(5), pp. 2019-2025 [abstract only].
Kusser , "Chemically modified nucleic acid aptamers for in vitro selections: evolving evolution," J. Biotechnol., Mar. 2000, pp. 27-38, vol. 74(1) [abstract only].
Lockman et al., "Heterogeneous Blood-Tumor Barrier Permeability Determines Drug Efficacy in Experimental Brain Metastases of Breast Cancer," Clin. Cancer Res., Dec. 1, 2010, pp. 5664-5678 (25 pgs.), vol. 16(23).
Loreau et al., "Blockage of AMV reverse transcriptase by antisense oligodeoxynucleotides," FEBS Lett., Nov. 12, 1990, pp. 53-56, vol. 274(1-2) [abstract only].
Ma et al., "Design and synthesis of RNA miniduplexes via a synthetic linker approach," Biochemistry, Feb. 23, 1993, pp. 1751-1758, vol. 32(7) [abstract only].
Ma et al., "Design and synthesis of RNA miniduplexes via a synthetic linker approach. 2. Generation of covalently closed, double-stranded cyclic HIV-1 TAR RNA analogs with high Tat-binding affinity," Nucleic Acids Res., Jun. 11, 1993, pp. 2585-2589, vol. 21(11).

(56) References Cited

OTHER PUBLICATIONS

Macaya et al., "Thrombin-binding DNA aptamer forms a unimolecular quadruplex structure in solution," Proc. Natl. Acad. Sci. USA, Apr. 15, 1993, pp. 3745-3749, vol. 90(8).
Martinez et al., "Single-stranded antisense siRNAs guide target RNA cleavage in RNAi," Cell, Sep. 6, 2002, pp. 563-74, vol. 110(5).
Matsukura et al., "Phosphorothioate analogs of oligodeoxynucleotides: inhibitors of replication and cytopathic effects of human immunodeficiency virus," Proc. Natl. Acad. Sci. USA, Nov. 1987, pp. 7706-7710, vol. 84(21).
Mayer et al., "Vesicles of variable sizes produced by a rapid extrusion procedure," Biochim. Biophys. Acta., Jun. 13, 1986, pp. 161-168, vol. 858(1) [abstract only].
Mayhew et al., "Characterization of liposomes prepared using a microemulsifier," Biochim. Biophys. Acta., Aug. 22, 1984, pp. 169-174, vol. 775(2) [abstract only].
Mayhew et al., "High-pressure continuous-flow system for drug entrapment in liposomes," Methods. Enzymol., 1987; pp. 64-77, vol. 149 [abstract only].
McCurdy et al., "Deoxyoligonucleotides with Inverted Polarity Synthesis and Use in Triple-Helix Formation," Nucleosides and Nucleotides, 1991, pp. 287-290, vol. 10(1-3) [1st page only].
Morales et al., "Biogenesis of lysosomes by endocytic flow of plasma membrane," Biocell., Dec. 1999, vol. 23(3), pp. 149-160 [abstract only].
Nelson et al., "Bifunctional oligonucleotide probes synthesized using a novel CPG support are able to detect single base pair mutations," Nucleic Acids Res., Sep. 25, 1989, pp. 7187-7194, vol. 17(18).
O'Brien et al., "Identification of prosaposin as a neurotrophic factor," Proc. Natl. Acad. Sci. USA, Sep. 1994, vol. 91(20), pp. 9593-9596.
Ono et al., "DNA triplex formation of oligonucleotide analogues consisting of linker groups and octamer segments that have opposite sugar-phosphate backbone polarities," Biochemistry, Oct. 15, 1991, pp. 9914-9912, vol. 30(41) [abstract only].
Oya et al., "Pathological study of mice with total deficiency of sphingolipid activator proteins (SAP knockout mice)," Acta Neuropathol., Jul. 1998, vol. 96(1), pp. 29-40 [abstract only].
Pagano et al., "Interactions of liposomes with mammalian cells," Annu. Rev. Biophys. Bioeng., 1978, pp. 435-468, vol. 7 [abstract only].
Pàmpols et al., "Neuronopathic juvenile glucosylceramidosis due to sap-C deficiency: clinical course, neuropathology and brain lipid composition in this Gaucher disease variant," Acta Neuropathol., Jan. 1999, vol. 97(1), pp. 91-97 [abstract only].
Pardridge, "Brain Drug Targeting: The Future of Brain Drug Development," J. Clin. Pathol., Feb. 2002, pp. 158, vol. 55(2).
Pardridge, "The Blood-Brain Barrier: Bottleneck in Brain Drug Development," NeuroRx., Jan. 2005, pp. 3-14, vol. 2(1).
Perez et al., "Magnetic relaxation switches capable of sensing molecular interactions," Aug. 2002, pp. 753-853, vol. 20(8) [abstract only].
Rafi et al., "Mutational analysis in a patient with a variant form of Gaucher disease caused by SAP-2 deficiency," Somat. Cell Mol. Genet., Jan. 1993, pp. 1-7, vol. 19(1) [abstract only].
Richardson et al., "Tethered Oligonucleotide Probes. A Strategy for the Recognition of Structured RNA," J. Am. Chem. Soc., 1991, pp. 5109-5111, vol. 113 (13).
Scaringe et al., "Chemical synthesis of biologically active oligoribonucleotides using beta-cyanoethyl protected ribonucleoside phosphoramidites," Nucleic Acids Res., Sep. 25, 1990, pp. 5433-5441, vol. 18(18).
Schnabel et al., "Mutation in the sphingolipid activator protein 2 in a patient with a variant of Gaucher disease," FEBS Lett., Jun. 17, 1991, pp. 57-59, vol. 284(1).
Schwarz et al., "Evidence that siRNAs function as guides, not primers, in the Drosophila and human RNAi pathways," Mol. Cell, Sep. 2002, pp. 537-548, vol. 10(3).
Seela et al., "Oligodeoxyribonucleotides containing 1,3-propanediol as nucleoside substitute," Nucleic Acids Res., Apr. 10, 1987, pp. 3113-3129, vol. 15(7).
Shaw et al., "Induction of Macrophage Antitumor Activity by Acetylated Low Density Liproprotein Containing Lipophilic Muramyl Tripeptide Density Lipoprotein Containing Lipophilic Muramyl Tripeptide", Proc. Natl. Acad. Sci. USA, Aug. 1988, pp. 6112-6116, vol. 85(16).
Stein et al., "Oligodeoxynucleotides as inhibitors of gene expression: a review," Cancer Res., May 15, 1988, pp. 2659-2668, vol. 48(10).
Steinbrecher, "Oxidation of Human Low Density Lipoprotein Results in Derivatization of Lysine Residues of Apolipoprotein B by Lipid Peroxide Decomposition Products", The Journal of Biological Chemistry, Mar. 15, 1987, pp. 3603-3608, vol. 262(8).
Sun, "Technology evaluation: Selex, Gilead Sciences Inc.," Curr. Opin. Mol. Ther., Feb. 2000, pp. 100-105, vol. 2(1) [abstract only].
Szoka et al., "Comparative Properties and Methods of Preparation of Lipid Vesicles (Liposomes)," Annu. Rev. Biophys. Bioeng., 1980, pp. 467-508, vol. 9 [1st page only].
Tsuboi et al., "Prosaposin prevents programmed cell death of rat cerebellar granule neurons in culture," Brain Res. Dev. Brain Res., Oct. 1, 1998, vol. 110(2), pp. 249-255 [abstract only].
Tyagi et al., "Molecular Beacons: Probes that Fluoresce upon Hybridization," Nature Biotechnology, Mar. 1996, pp. 303-308, vol. 14(3) [abstract only].
Usman et al., "The automated chemical synthesis of long oligoribuncleotides using 2'-O-silylated ribonucleoside 3'-O-phosphoramidites on a controlled-pore glass support: synthesis of a 43-nucleotide sequence similar to the 3'-half molecule of an *Escherichia coli* formylmethionine tRNA," J. Am. Chem. Soc., 1987, pp. 7845-7854, vol. 109(25) [1st page only].
Wang et al., "A DNA aptamer which binds to and inhibits thrombin exhibits a new structural motif for DNA," Biochemistry, Mar. 2, 1993, pp. 1899-1904, vol. 32(8) [abstract only].
Wenger et al., "Clinical, pathological, and biochemical studies on an infantile case of sulfatide/GM1 activator protein deficiency," Am. J. Med. Genet., Jun. 1989, pp. 255-265, vol. 33(2) [abstract only].
Wincott et al., "A practical method for the production of RNA and ribozymes," Methods Mol. Biol., 1997, pp. 59-68, vol. 74 [abstract only].
Wincott et al., "Synthesis, deprotection, analysis and purification of RNA and ribozymes," Nucleic Acids Res., Jul. 25, 1995, pp. 2677-2684, vol. 23(14).
Wu et al., "Immunofluorescent labeling of cancer marker Her2 and other cellular targets with semiconductor quantum dots," Nature Biotechnology, Jan. 2003, pp. 41-46, vol. 21(1).

\* cited by examiner

SDVYCEVCEFLVKEVTKLIDNNKTEKEILDAFDKMCSKLPKSLSEECQEVVDTYGSSILSILLEEVSPELVCSMLHLCSG
  1     ↑LBR          ↑NR                          ↑AR        ↑       LBR
80

Figure 3

Delivery of GFP 22 siRNA into EGFP 4T1 breast tumor cells 20X len, 800 mSec exposure, Photoshop: input levels 27, 1.19, 164, output level 255. Size: 3X2.29 inches.

Delivery of GFP 22 siRNA into neuroblastoma (CHLA-20) cancer cells.

Rhodamine-GFP22 siRNA     Phase-Contrast     Merged (a)                       (b)                (c)

FUSOGENIC PROPERTIES OF SAPOSIN C AND RELATED PROTEINS AND PEPTIDES FOR APPLICATION TO TRANSMEMBRANE DRUG DELIVERY SYSTEMS

CROSS-REFERENCE TO RELATED APPLICATION

This application claims the benefit of U.S. Provisional Patent Application Ser. No. 60/745,969 filed Apr. 28, 2006, which application is hereby incorporated by reference in its entirety.

This invention was made with government support under DK057690 awarded by the National Institutes of Health. The government has certain rights in the invention.

FIELD OF INVENTION

The present invention relates to methods of delivering pharmaceutical or therapeutic agents across biological membranes, where the agent is contained within or intercalated into a phospholipid membrane and delivery is facilitated by a membrane fusion protein. More particularly, the present invention relates to methods for enhancing the transport and delivery of pharmaceutical agents across and/or within dermal and mucosal membranes or the blood-brain barrier, where the pharmaceutical agent is contained within a liposome, and delivery is facilitated using saposin C, which is in association with the liposome.

BACKGROUND OF THE INVENTION

The therapeutic efficacy of pharmaceutical or therapeutic agents relies on the delivery of adequate doses of a pharmaceutical agent to the site of action. Many modes of delivery have been developed, including, for example, enteral (oral), parenteral (intramuscular, intravenous, subcutaneous), and topical administration. In most instances the administration system is chosen for reliable dosage delivery and convenience.

Typically, parenteral administration is the most reliable means of delivering a pharmaceutical to a patient. See, Goodman et al., Goodman and Gilman's Pharmacological Basis of Therapeutics, Pergamon Press, Elmsford, N.Y. (1990) and Pratt et al. Principles of Drug Action: The Basis of Pharmacology, Churchill Livingstone, New York, N.Y. (1990). Each parenteral mechanism insures that a prescribed dosage of the pharmaceutical agent is inserted into the fluid compartment of the body where it can be transported. The disadvantage of these modes of delivery is that they require an invasive procedure. The invasive nature of administration is inconvenient, painful and subject to infectious contamination.

Enteral and topical administration are more convenient, generally non-painful, and do not predispose to infection, however both have limited utility. The gastrointestinal and dermal surfaces present formidable barriers to transport and therefore, some pharmaceutical agents are not absorbed across these surfaces. Another drawback to patient directed modes of administration (enteral, topical and subcutaneous) is compliance. Pharmaceutical agents that have a short half-life require multiple daily doses. As the number of doses increases, patient compliance and therapeutic efficacy decrease. Simplified and/or less frequent administration schedules can aid in optimizing patient compliance. Wilson et al. (1991) Harrison's Principles of Internal Medicine, 12th Ed., McGraw-Hill, Inc., New York, N.Y.

The skin is an efficient barrier to the penetration of water soluble substances, and the rate of transdermal pharmaceutical agent absorption is primarily determined by the agent's lipid solubility, water solubility, and polarity. Highly polar or water soluble pharmaceutical agents are effectively blocked by the skin. Even very lipophilic pharmaceutical agents penetrate the dermis very slowly compared with the rate of penetration across cell membranes. See Pratt et al. supra.

Efforts to develop more effective and convenient modes of pharmaceutical administration have led to the development of transdermal delivery systems. Many current transdermal pharmaceutical agent delivery systems rely upon pharmaceutical agents that are absorbed when admixed with inert carriers. See Cooper et al. (1987) "Penetration Enhancers", in Transdermal Delivery of Drugs, Vol. II, Kyodonieus et al., Eds., CRC Press, Boca Raton, Fla. Few pharmaceutical agents fit this profile and those which do are not always predictably absorbed. Various forms of chemical enhancers, such as those enhancing lipophilicity, have been developed to improve transdermal transport when physically mixed with certain therapeutic agents and provide more predictable absorption. See for example, U.S. Pat. Nos. 4,645,502; 4,788,062; 4,816,258; 4,900,555; 3,472,931; 4,006,218; and 5,053,227. Carriers have also been coupled to pharmaceutical agents to enhance intracellular transport. See Ames et al. (1973) Proc. Natl. Acad. Sci. USA, 70:456-458 and (1988) Proc. Int. Symp. Cont. Rel. Bioact. Mater., 15:142.

Similar to the problems inherent in trans-dermal delivery of pharmaceuticals, the blood-brain barrier is an obstacle to CNS drug delivery. In fact, the blood-brain barrier is considered to be a "bottleneck" in brain drug development, and is perhaps the single most important limitation on the future growth of neurotherapeutics. (Pardridge, W. M., The Blood-Brain Barrier: Bottleneck in Brain Drug Development, The Journal of the American Society for Experimental Neuro-Therapeutics, Vol 2, 3-14, January 2005; Pardridge, W. M. Brain drug targeting: the future of brain drug development. Cambridge, UK: Cambridge University Press, 2001.) The BBB is formed by the brain capillary endothelium and prevents transport of approximately 100% of large-molecules (such as monoclonal antibodies, recombinant proteins, antisense or gene therapeutics) and more than 98% of all small-molecule drugs into the brain. Although the average molecular mass of a CNS-active drug is 357 daltons, even a small, 100 dalton molecule such as histamine does not pass through the BBB when infused into a mouse and allowed to distribute over thirty minutes time. In fact, a review of the Comprehensive Medicinal Chemistry database shows that, of more than 7000 small molecule drugs, only 5% treat the CNS, and this 5% treats only depression, schizophrenia, and insomnia.

Thus, most drugs do not cross the BBB. Unfortunately, many disorders of the central nervous system (CNS) could benefit from improved drug therapy directed towards the CNS. While there is relatively little research with respect to agents known to cross the BBB, there are characteristics that are predictive of a likelihood of success of delivery into the CNS. These are: 1) molecular mass under a 400-500 Dalton threshold, and 2) high lipid solubility. Presently, only four categories of CNS disorders respond to such molecules, including affective disorders, chronic pain, and epilepsy. Migraine headache may be considered a CNS disorder, and could also be included in this category. In contrast, patients with diseases such as Alzheimer's disease, Parkinson's disease, Huntington's disease, A.L.S., multiple sclerosis, neuro-AIDS, brain cancer, stroke, brain or spinal cord trauma, autism, lysosomal storage disorders, fragile X syndrome, inherited ataxias, and blindness have very limited options with respect to pharmaceutical treatments. (There has been some success with L-DOPA treatment in Parkinson's patients, and multiple sclerosis can be treated with cytokines acting on the peripheral immune system.) (See generally, Partridge, supra).

In many of the above listed disorders, delivery across the BBB is the rate limiting problem in gene therapy or enzyme replacement therapy. Many of these disorders could be treated with drugs, enzymes or genes already discovered. However, these drugs do not cross the BBB and cannot be considered for therapeutic use for that reason. Because of the impermeability of the BBB, other approaches to drug delivery into the CNS must be used. These include the use of small molecules, trans-cranial brain drug delivery, and BBB disruption. However, none of these approaches provide solutions to the BBB problem that can be practically implemented in a large number of patients. (Pardridge, W. M., "The Blood-Brain Barrier")

Saposins, a family of small (~80 amino acids) heat stable glycoproteins, are essential for the in vivo hydrolytic activity of several lysosomal enzymes in the catabolic pathway of glycosphingolipids (see Grabowski, G. A., Gatt, S., and Horowitz, M. (1990) Crit. Rev. Biochem. Mol. Biol. 25, 385-414; Furst, W., and Sandhoff, K., (1992) Biochim. Biophys. Acta 1126, 1-16; Kishimoto, Y., Kiraiwa, M., and O'Brien, J. S. (1992) J. Lipid. Res. 33, 1255-1267). Four members of the saposin family, A, B, C, and D, are proteolytically hydrolyzed from a single precursor protein, prosaposin (see Fujibayashi, S., Kao, F. T., Hones, C., Morse, H., Law, M., and Wenger, D. A. (1985) Am. J. Hum. Genet. 37, 741-748; O'Brien, J. S., Kretz, K. A., Dewji, N., Wenger, D. A., Esch, F., and Fluharty, A. L. (1988) Science 241, 1098-1101; Rorman, E. G., and Grabowski, G. A. (1989) Genomics 5, 486-492; Nakano, T., Sandhoff, K., Stumper, J., Christomanou, H., and Suzuki, K. (1989) J. Biochem. (Tokyo) 105, 152-154; Reiner, O., Dagan, O., and Horowitz, M. (1989) J. Mol. Neurosci. 1, 225-233). The complete amino acid sequences for saposins A, B, C and D have been reported as well as the genomic organization and cDNA sequence of prosaposin (see Fujibayashi, S., Kao, F. T., Jones, C., Morse, H., Law, M., and Wenger, D. A. (1985) Am. J. Hum. Genet. 37, 741-748; O'Brien, J. S., Kretz, K. A., Dewji, N., Wenger, D. A., Esch, F., and Fluharty, A. L. (1988) Science 241, 1098-1101; Rorman, E. G., and Grabowski, G. A. (1989) Genomics 5, 486-492). A complete deficiency of prosaposin with mutation in the initiation codon causes the storage of multiple glycosphingolipid substrates resembling a combined lysosomal hydrolase deficiency (see Schnabel, D., Schroder, M., Furst, W., Klien, A., Hurwitz, R., Zenk, T., Weber, J., Harzer, K., Paton, B. C., Poulos, A., Suzuki, K., and Sandhoff, K. (1992) J. Biol. Chem. 267, 3312-3315).

Saposins are defined as sphingolipid activator proteins or coenzymes. Structurally, saposins A, B, C, and D have approximately 50-60% similarity including six strictly conserved cysteine residues (see Furst, W., and Sandhoff, K., (1992) Biochim. Biophys. Acta 1126, 1-16) that form three intradomain disulfide bridges whose placements are identical (see Vaccaro, A. M., Salvioli, R., Barca, A., Tatti, M., Ciaffoni, F., Maras, B., Siciliano, R., Zappacosta, F., Amoresano, A., and Pucci, P. (1995) J. Biol. Chem. 270, 9953-9960). All saposins contain one glycosylation site with conserved placement in the N-terminal sequence half, but glycosylation is not essential to their activities (see Qi. X., and Grabowski, G. A. (1998) Biochemistry 37, 11544-11554; Vaccaro, A. M., Ciaffoni, F., Tatti, M., Salvioli, R., Barca, A., Tognozzi, D., and Scerch, C. (1995) J. Biol. Chem. 270, 30576-30580). In addition, saposin A has a second glycosylation site in C-terminal half.

All saposins and saposin-like proteins and domains contain a "saposin fold" when in solution. This fold is a multiple α-helical bundle motif, characterized by a three conserved disulfide structure and several amphipathic polypeptides. Despite this shared saposin-fold structure in solution, saposins and saposin-like proteins have diverse in vivo biological functions in the enhancement of lysosomal sphingolipid (SL) and glycosphingolipid (GSL) degradation by specific hydrolases. Because of these roles, the saposins occupy a central position in the control of lysosomal sphingolipid and glycosphingolipid metabolisms (see Kishimoto, Y., Kiraiwa, M., and O'Brien, J. S. (1992) J. Lipid. Res. 33, 1255-1267; Fujibayashi, S., Kao, F. T., Hones, C., Morse, H., Law, M., and Wenger, D. A. (1985) Am. J. Hum. Genet. 37, 741-748; O'Brien, J. S., Kretz, K. A., Dewji, N., Wenger, D. A., Esch, F., and Fluharty, A. L. (1988) Science 241, 1098-1101).

The structural characteristic of these saposins is of great importance to the diverse mechanisms of activation. Since all of these proteins have high sequence similarity, but different mechanisms of action with lipid membranes, one can speculate that the specific biological functions of saposins and saposin-like proteins are the result of the differential interactions with the biological membrane environments. In vitro, saposin A enhances acid β-glucosidase activity at μM concentration, but saposin C deficiency leads to glucosylceramide storage and a "Gaucher disease-like" phenotype (see Schnable, D., Schroder, M., and Sandhoff, K. (1991) FEBS Lett. 284, 57-59; Rafi. M. A., deGala, G., Zhang, X. L., and Wenger, D. A. (1993) Somat. Cell Mol. Genet. 19, 1-7). Activation of saposin B takes place through solubilizing and presenting glycosphingolipid substrates to lysosomal enzymes (see Furst, W., and Sandhoff, K., (1992) Biochim. Biophys. Acta 1126, 1-16).

Saposin C promotes acid β-glucosidase activity by inducing in the enzyme conformational change at acidic pH (see Berent, S. L., and Radin, N. S. (1981) Biochim. Biophys. Acta 664, 572-582; Greenberg, P., Merrill, A. H., Liotta, D. C., and Grabowski, G. A. (1990) Biochim. Biophys. Acta 1039, 12-20; Qi. X., and Grabowski, G. A. (1998) Biochemistry 37, 11544-11554). This interaction of saposin C with the enzyme occurs on negatively charged phospholipid surfaces. In vitro and ex vivo saposins A and D function to enhance the degradation of galactosylceramide and ceramide/sphingomyelin, respectively (see Harzer, K., Paton, B. C., Christomanou, H., Chatelut, M., Levade, T., Hiraiwa, M. and O'Brien, J. S. (1997) FEBS Lett. 417, 270-274; Klien, A., Henseler, M., Klein, C., Suzuki, K., Harzer, K., and Sandhoff, K. (1994) Biochem. Biophys. Res. Commun, 200, 1440-1448). Patients lacking the individual saposins B and C showed a variant form of metachromatic leukodystrophy and Gaucher disease, respectively. (see Wenger, D. A., DeGala, G., Williams, C., Taylor, H. A., Stevenson, R. E., Pruitt, J. R., Miller, J., Garen, P. D., and Balentine, J. D. (1989) Am. J. Med. Genet. 33, 255-265) (see Christomanou, H., Aignesberger, A., and Linke, R. P. (1986) Biol. Chem. Hoppe-Seyler 367, 879-890).

The primary physiological function of saposin C has been defined by a glycosphingolipid (GSL) storage disease similar to neuronopathic "Gaucher's disease" in patients with a deficiency of the protein. Saposin C is a critical physiologic activator for the lysosomal enzyme, acid β-glucosidase. In addition to stimulating the glucosylceramide degradation by acid β-glucosidase, saposin C has several other potential roles. These include inter-membrane transport of gangliosides and GSLs, reorganization and destabilization of phospholipids-containing membranes, and fusion of acid phospholipids vesicles (see Hiraiwa, M., and Soeda, S. et al.

(1992) Proc. Natl. Acad. Sci. USA, 89, 11254-11258; You, H. X., and Yu, L. et al., (2001) FEBS Lett. 503, 97-102; You, H. X. and Qi, X. et al. (2003) Biophys. J. 84, 2043-2057; Vaccaro, A. M., and Tatti, M. et al., (1994) FEBS Lett. 349, 181-186; Wang, Y., and Grabowski, G. et al., Biochem. Biophys., 415: 43-53; Qi, X. and Chu, Z., (2004) Arch. Biochem. Biophys., 424: 210-218). Saposin C associates with phophatidyserine (PS) membranes by embedding its amino- and carboxyl-end helices into the outer leaflet of membranes (see Qi, X. and Grabowski, G. A., (2001) J. Biol. Chem., 276, 27010-27017). Increasing evidence indicates that intereactions of saposins with appropriate membranes are crucial for their specificity and activity.

Moreover, PSAP, the precursor of saposins, is a neurotropic factor with in vitro neuritogenic, in vivo nerve growth promoting, and apoptosis protection properties (see Qi, X. and Qin, W. et al. (1996) J. Biol. Chem., 217, 6874-6880; O'Brien, J. S. and Carson, G. S. et al. (1994) Proc. Natl. Acad. Sci. USA 91, 9593-9596; Qi, X. and Kondoh, K. et al. (1999) Biochemistry 38, 6284-6291; Kotani, Y. S, and Matsuda, S. et al. (1996) J. Neurochem. 66, 2019-2025; Koani, Y. and Matsuda, S. et al. (1996) J. Neurochem. 66, 2197-2200; Tsuboi, K. and Hiraiwa, M. et al. (1998) Brain Res. Dev. Brain Res. 110, 249-255). Such neuritogenic functions are mediated through sequences in the $NH_2$-terminal half of saposin C (see Qi, X. and Qin, W. et al. (1996) J. Biol. Chem. 271, 6874-6880; O'Brien, J. S, and Carson, G. S. et al. (1995) FASEB J. 9, 681-685). The minimum sequence required for in vitro neuritogenic activity spans amino acid residues 22-31 of saposin C in humans and mice. Neurological functions of PSAP and saposin C are mediated by activation of the enzymes in the MAPK pathway through a G-protein-associated cell membrane receptor in a number of neuralgia-derived cells (see Campana, W. M. and Hiraiwa, M. et al. (1996) Biochem. Biophys. Res. Commun. 229, 706-712; Hiraiwa, M. and Campana, W. M. et al. (1997) Biochem. Biophys. Res. Commun. 240, 415-418).

Human and mouse PSAP genetic defects result in total saposin deficiency (see Harzer, K. and Paton, B. C. et al. (1989) Eur. J. Pediatr. 149, 31-39; Hulkova, H., and Cervenkova, M. et al. (2001) Hum. Mol. Genet. 10, 927-940; Fujita, N. and Suzuki, K. et al., Hum. Mol. Genet. 5, 711-725). This deficiency can lead to aberrant accumulation of multivesicular bodies (MVBs), as observed in the skin fibroblasts from PSAP-deficient patients (see Harzer, K. and Paton, B. C. et al. (1989) Eur. J. Pediatri. 149, 31-39; Burkhardt, J. K. and Huttler, S. et al. (1997) Eur. J. Cell Biol. 73, 10-18). Further, the sinusoidal cells in liver from a PSAP-deficient patient has been observed to be crowded with multivesicular inclusions (see Sandhoff, K. and Kolter, T. et al. (2000) The Metabolic and Molecular Bases of Inherited Disease, 3371-3388; Harzer, K. and Paton, B. C. et al. (1989) Eur. J. Pediatr. 149, 31-39). Similar MVB structures also were found in fibroblasts from a saposin C-deficient patient (see Pampols, T. and Pineda, M. et al. (1999) Acta Neuropathol. 97, 91-97). In PSAP −/− (double-knock out) mice, inclusions consisting of numerous concentric lamellar bodies and dense granular structures were noted in a variety of tissues and cells (see Oya, Y., and Nakayasu, H. et al. (1998) Acta Neuropathol 96, 29-40). Thin sections of mouse PSAP −/− cells revealed a selective accumulation of MVBs by electron microscopy (see Morales, C. R. and Zhao, Q. et al. (1999) Biocell 23, 149-160).

MVBs, a subset of the late endosomes, have a crucial role in communications by vesicular transport between the trans-Golgi network, the plasma membrane, and lysosomal/vacuolar organelles (see Katzman, D. J. and Odorizzi, G. et al. (2002) Nat. Rev. Mol. Cell. Biol. 3, 893-905). One function of MVBs is to maintain the cellular homeostasis required for neuronal development and growth. The hypothetical "signaling endosome" model explains that the ligand-receptor complex on an endosomal signaling platform is transported retrogradely from the distal axon to the cell body to promote gene expression and neuron survival (see Ginty, D. D. and Segal, R. A. (2002) Curr. Opin. Neurobiol. 12, 268-274). The abnormalities in MVB structures in neurons of PSAP−/− mice may disrupt the retrograde movement of neurotrophins via vesicular signaling transports and may impair the development of neuronal cells in the CNS.

Introducing exogenous PSAP or saposin C into the medium of cultured fibroblasts from the PSAP-deficient patient reverses the aberrant accumulation of MVBs, suggesting that saposin C is a key regulatory molecule in MVB formation (see Burkhardt, J. K. and Huttler, S. et al. (1997) Eur. J. Cell Biol. 73 10-18; Chu, Z., and Witte, D. P. et al. (2004) Exp. Cell Res.).

In addition to mediating MVB formation, saposin plays a role in membrane fusion. Membrane fusion is a major event in biological systems driving secretion, endocytosis, exocytosis, intracellular transport, fertilization, and muscle development (see Christomanou, H., Chabas, A., Pampols, T., and Guardiola, A. (1989) Klin, Wochenschr. 67, 999-1003). Recent experimental evidence generated by this inventor has indicated that saposin-lipid membrane interactions play a critical role in saposin-mediated membrane fusion of lipids thereby facilitating transport of active agents across these biological membranes.

The present invention also relates to a method of administering imaging agents across cellular membranes including the blood-brain barrier using saposin C containing liposomes. Non-invasive imaging techniques can be used to monitor the distribution and efficacy of liposomal delivery systems, thereby facilitating the evaluation and clinical application of gene therapy or therapeutic treatment using liposomes. Imaging agents may use magnetic resonance, fluorescence, or CT/PET as a means of detection. However, key obstacles to successful use of imaging agents to monitor liposome delivery are ease of detection, availability of pertinent technology and ease and efficiency of delivery.

With respect to using liposomes to deliver imaging agents, lipophilic molecules are generally appropriate, though the present invention is not limited to use with such molecules. Without intending to be limited by theory, lipophilic dyes or dyes containing a lipophilic moiety may intercalate into the liposomal membrane or reconstitute into the lipid core of liposomal structures. Examples of such dyes known in the art are the indocarbocyanine dye, DiI. DiI is a fluorescent carbocyanine dye that is routinely used to label lipid membranes. Other similar dyes are DiA or DiaO as described in Honig, M. G. et al, *DiI and DiO: versatile fluorescent dyes for neuronal labeling and pathway tracing*. Trends Neurosci. 12:333-335, 340-331, 1989. Other lipophilic dyes that may be used with the present invention include PKH2, NeuroVue Green, PKH 26, NeuroVue Red, and NeuroVue Maroon, as described by Fritzsch, et al. *Diffusion and Imaging properties of Three New Lipophilic Tracers, Neuro Vue Maroon, Neuro Vue and Neurovue Green and their use for Double and Triple Labeling of Neuronal Profile*, manuscript. Any of these dyes may be used with the present invention described herein, either alone or in combination.

Also used in the art and appropriate to the present invention are imaging agents having two or more imaging properties. Such agents allow the researcher or clinician the ability to use multiple methods of imaging to detect administered imaging agents. An example of such agents are the so-called PTIR dyes as described by Li, H., et al., *MR and Fluorescent Imaging of Low-Density Lipoprotein Receptors*, Acad Radiol. 2004; 11:1251-1259, incorporated herein by reference. These dyes contain both a fluorophore and a Gd(III) moiety that allow for detection via magnetic resonance imaging (MRI) or confocal fluorescence microscopy. The lipophilic side chain facilitates the intercalation of the dye into phospholipid monolayers. Thus, these dyes are appropriate for use with liposomal delivery systems such as the one described herein.

Proton MR imaging offers the advantages of being noninvasive, tomographic, and of high resolution. In recent years, magnetic resonance imaging (MRI) has emerged as a powerful tool in clinical settings because it is noninvasive and yields an accurate volume rendering of the subject. See generally, U.S. Pat. No. 6,962,686 Kayyem, et al. entitled Cell-specific gene delivery vehicles. These advantages make MRI the technique of choice in both medical imaging and as an imaging tool for use in biological experiments. Unlike light-microscope imaging techniques based upon the use of dyes or fluorochromes, MRI does not produce toxic photobleaching by-products. Furthermore, unlike light-microscopy, MRI is not limited by light scattering or other optical aberrations to cells within approximately only one hundred microns of the surface. Agents having MRI properties such as those described above may be used with the present invention.

Accordingly, there exists a significant need for nontoxic agents which can improve the delivery or transport of pharmaceutical or imaging agents across or through biological membranes, including the blood-brain barrier. The present invention fulfills these needs.

SUMMARY OF THE INVENTION

The present invention relates to methods of delivering agents, e.g., pharmaceutical or therapeutic agents, across biological membranes, where the agent is contained within or intercalated into a phospholipid membrane and delivery is facilitated by a membrane fusion protein. More particularly, the present invention relates to methods for enhancing the transport and delivery of agents across and/or within dermal and mucosal membranes or the blood-brain barrier, where the agent is contained within a liposome, and delivery is facilitated using saposin C, which is in association with the liposome.

As described herein, the present invention comprises a method for delivering a pharmaceutical agent through a biological membrane, including the blood-brain barrier and cellular membranes, wherein the method comprises applying to the membrane a composition comprising anionic phospholipids with or without neutral phospholipids, a safe and effective amount of the pharmaceutical agent contained within the phospholipids, and a fusogenic protein or polypeptide derived from prosaposin in a pharmaceutically acceptable carrier.

In one embodiment, the anionic phospholipid membrane is a vesicle. In another embodiment, the vesicle is a liposome. The liposomes are a form of nanocontainer and nanocontainers, such as nanoparticles or liposomes, are commonly used for encapsulation of drugs. Cationic phospholipids may also be used, provided that the overall charge of the resulting liposome is negative.

In another embodiment of the present invention, the pH of the protein-lipid composition is acidic. In another embodiment of the present invention, the pH of the composition is between about 6.8 and 2. In another embodiment of the present invention, the pH of the composition is between about 5.5 and 2. In another embodiment, the pH is between about 5.5 and about 3.5.

In another embodiment, the protein and lipid composition is provided in a dry form, e.g., a powder. In another embodiment, the protein and lipid composition dry form is treated with an acid. In one embodiment, the acid is an acidic buffer or organic acid. In another embodiment, the acid is added at a level sufficient to protonate at least a portion of the protein, wherein the composition has a pH of from about 5.5 and about 2. In another embodiment, the acid is added at a level sufficient to substantially protonate the protein, wherein the composition has a pH of from about 5.5 and about 2.

In a further embodiment, the pH of the protein and lipid composition dry powder that has been treated with an acid sufficient to protonate at least a portion of the protein is then substantially neutralized. In one embodiment, the pH is neutralized with a neutral pH buffer. In one embodiment, the pH is neutralized with a neutral pH buffer sufficiently to control the size of the resulting liposome. In another embodiment, the pH is neutralized with a neutral pH buffer sufficiently to control the size of the resulting liposome to provide for liposomes having mean diameters of about 200 nanometers. In another embodiment, the liposomes have a mean diameter of between 50 and 350 nanometers. In another embodiment, the liposomes have a mean diameter of between 150 and 250 nanometers. In another embodiment, the buffer is added to the composition to provide a final composition pH of from about 5 to about 14, preferably from about 7 to 14, more preferably from about 7 to about 12, more preferably from about 7 to about 10, and even more preferably from about 8 to about 10.

In one embodiment of the present invention, short-chain lipids are used. Generally, the concentration of the fusogenic protein or polypeptide is of a sufficient amount to deliver the pharmaceutical agent within and/or through the membrane. In another embodiment, the concentration of phospholipids in in vitro membranes is in at least a 5-fold excess to that of the fusogenic protein or polypeptide by molar ratio. In another embodiment, the concentration of phospholipids in in vitro membranes is in at least a 10-fold excess to that of the fusogenic protein or polypeptide by molar ratio. In another embodiment, the concentration of phospholipids in in vitro membranes is in at least a 15-fold excess to that of the fusogenic protein or polypeptide by molar ratio. In one embodiment, the concentration of phospholipids in in vitro membranes is in at least a 20-fold excess to that of the fusogenic protein or polypeptide by molar ratio. In another embodiment, the concentration of phospholipids in in vitro membranes are in about a 10 to about 50-fold excess or about 20 to about 30 fold excess to that of the fusogenic protein or polypeptide by molar ratio.

In one embodiment, the concentration of phospholipids in in vivo or cell membrane systems are in at least a 1-fold excess to that of the fusogenic peptide by molar ratio. In one embodiment, the concentration of phospholipids in in vivo or cell membrane systems are in at least a 2-fold excess to that of the fusogenic peptide by molar ratio. In another embodiment, the concentration of phospholipids in in vivo or cell membrane systems are in at least a 3-fold excess to that of the fusogenic peptide by molar ratio. In another embodiment, the concentration of phospholipids in in vivo or cell membrane systems are in about a 1 to about a 10 fold excess or about 3 to 7 fold excess to that of the fusogenic peptide by molar ratio.

Without wishing to be bound by theory in any way, it is believed that the membrane fusion protein is associated with the phospholipid membrane, through electrostatic and hydrophobic and hydrophobic interactions and the overall charge of the lipid composition is negative.

In accordance with the present invention, the targeted biological membranes include, but are not limited to, dermal membranes, mucosal membranes, the blood-brain barrier and cellular membranes.

The preferred membrane fusion proteins include saposin C as well as other proteins, polypeptide analogues or polypeptides derived from either saposin C, SEQ. ID. NO. 1 through 13 and mixtures thereof.

In one embodiment, the membrane fusion protein comprises at least 8, 10, 12, 14, 16, 18, 20, 22, 24 or more contiguous amino acids of a sequence selected from saposin C, SEQ. ID. NO. 1 and SEQ. ID. NO. 2. In one embodiment, the membrane fusion protein comprises a peptide of the formula:

```
h-u-Cys-Glu-h-Cys-Glu-h-h-h-Lys-Glu-h-u-Lys-h-h-
Asp-Asn-Asn-Lys-u-Glu-Lys-Glu-h-h-Asp-h-h-Asp-
Lys-h-Cys-u-Lys-h-h (SEQ ID No. 14),
``` where h=hydrophobic amino acids, including, Val, Leu, Ile, Met, Pro, Phe, and Ala; and where u=uncharged polar amino acids, including, Thr, Ser, Tyr, Gly, Gln, and Asn, and mixtures thereof.

In another embodiment, the membrane fusion protein comprises one or more protein selected from other proteins, polypeptide analogues or polypeptides derived from either saposin C, SEQ. ID. NO. 1, SEQ. ID. NO. 2, polypeptides of the formula may be used:

```
h-u-Cys-Glu-h-Cys-Glu-h-h-h-Lys-Glu-h-u-Lys-h-h-
Asp-Asn-Asn-Lys-u-Glu-Lys-Glu-h-h-Asp-h-h-Asp-
Lys-h-Cys-u-Lys-h-h (SEQ ID No. 14),
``` where h=hydrophobic amino acids, including, Val, Leu, Ile, Met, Pro, Phe, and Ala; and where u=uncharged polar amino acids, including, Thr, Ser, Tyr, Gly, Gln, and Asn, and mixtures thereof.

In one embodiment, the membrane fusion protein comprises at least 8, 10, 12, 14, 16, 18, 20, 22, 24, 30 or more contiguous amino acids of the sequence: Ser Asp Val Tyr Cys Glu Val Cys Glu Phe Leu Val Lys Glu Val Thr Lys Leu Ile Asp Asn Asn Lys Thr Glu Lys Glu Ile Leu Asp Ala Phe Asp Lys Met Cys Ser Lys Leu Pro (SEQ ID No. 1). the membrane fusion protein comprises at least 8, 10, 12, 14, 16, 18, 20, 22, 24, 30 or more contiguous amino acids of the sequence: Val Tyr Cys Glu Val Cys Glu Phe Leu Val Lys Glu Val Thr Lys Leu Ile Asp Asn Asn Lys Thr Glu Lys Glu Ile Leu Asp Ala Phe Asp Lys Met Cys Ser Lys Leu Pro (SEQ ID No. 2).

In another embodiment, the membrane fusion protein comprising the sequence: Ser Asp Val Tyr Cys Glu Val Cys Glu Phe Leu Val Lys Glu Val Thr Lys Leu Ile Asp Asn Asn Lys Thr Glu Lys Glu Ile Leu Asp Ala Phe Asp Lys Met Cys Ser Lys Leu Pro (SEQ ID No. 1). In another embodiment, the membrane fusion protein comprising the sequence: Val Tyr Cys Glu Val Cys Glu Phe Leu Val Lys Glu Val Thr Lys Leu Ile Asp Asn Asn Lys Thr Glu Lys Glu Ile Leu Asp Ala Phe Asp Lys Met Cys Ser Lys Leu Pro SEQ ID No. 2). In another embodiment, the membrane fusion protein is a 22-mer comprising the sequence: CEFLVKEVTKLIDNNKTEKEIL (SEQ ID No. 18).

In another embodiment, the membrane fusion protein comprises saposin C. In another embodiment, the membrane fusion protein comprises saposin C in an oxidized, acetylated (for example, formylated and acetylated), acetoacetylated or lactosylated form by modification according to known methods (see, in particular, J. M. Shaw, op. cit.; Basu et al., Proc. Natl. Acad. Sci. USA 73, 3178-3182 (1976); J. Steinbrechert, Biol. Chem. 262, 3703 (1987)).

In one embodiment, the phospholipid membranes are anionic liposomes containing the pharmaceutical agent. In another embodiment, the liposomes are made from any mixture of lipids that contain anionic long-chain lipids. In another embodiment, the liposomes are made from a mixture containing anionic long-chain lipids, neutral long-chain lipids, and neutral short-chain lipids, wherein the overall charge of the resulting liposome is negative.

In selecting a lipid for preparing the liposomes used in the present invention, a wide variety of lipids will be found to be suitable for their construction. Particularly useful are any of the materials or combinations thereof known to those skilled in the art as suitable for liposome preparation. The lipids used may be of natural, synthetic or semi-synthetic origin.

In another embodiment, the liposomes are made from one or more biocompatible lipid. In another embodiment, the biocompatible lipid is selected from the group consisting of fatty acids, lysolipids, phosphatidylcholines, phosphatidylethanolamines, phosphatidylserines, phosphatidylglycerols, phosphatidylinositols, sphingolipids, glycolipids, glucolipids, sulfatides, glycosphingolipids, phosphatidic acids, palmitic acids, stearic acids, arachidonic acids, oleic acids, lipids bearing polymers, lipids bearing sulfonated monosaccharides, lipids bearing sulfonated disaccharides, lipids bearing sulfonated oligosaccharides, lipids bearing sulfonated polysaccharides, cholesterols, tocopherols, lipids with ether-linked fatty acids, lipids with ester-linked fatty acids, polymerized lipids, diacetyl phosphates, dicetyl phosphates, stearylamines, cardiolipin, phospholipids with fatty acids of 6-8 carbons in length, synthetic phospholipids with asymmetric acyl chains, ceramides, non-ionic lipids, sterol aliphatic acid esters, sterol esters of sugar acids, esters of sugar acids, esters of sugar alcohols, esters of sugars, esters of aliphatic acids, saponins, glycerol dilaurate, glycerol trilaurate, glycerol dipalmitate, glycerol, glycerol esters, alcohols of 10-30 carbons in length, 6-(5-cholesten-3beta-yloxy)-1-thio-beta-D-galactopyranoside, digalactosyldiglyceride, 6-(5-cholesten-3beta-yloxy)hexyl-6-amino-6-deoxy-1-thio-beta-D-galacto pyranoside, 6-(5-cholesten-3beta-yloxy)hexyl-6-amino-6-deoxyl-1-thio-alpha-D-manno pyranoside, 12-(((7'-diethylaminocoumarin-3-yl)carbonyl)methylamino)-octadecanoic acid, N-[12-(((7'-diethylaminocoumarin-3-yl) carbonyl)methyl-amino)octadecanoyl]-2-aminopalimitic acid, cholesteryl(4'-trimethyl-ammonio)butanoate, N-succinyldioleoylphosphatidylethanol-amine, 1,2-dioleoyl-sn-glycerol, 1,2-dipalmitoyl-sn-3-succinylglycerol, 1,3-dipalmitoyl-2-succinylglycerol, 1-hexadecyl-2-palmitoylglycerophosphoethanolamine, palmitoylhomocysteine, cationic lipids, N-[1-(2,3-dioleoyloxy)propyl]-N,N,N-trimethylammoium chloride, 1,2-dioleoyloxy-3-(trimethylammonio)propane, 1,2-dioleoyl-3-(4'-trimethyl-ammonio)butanoyl-sn-glycerol, lysophospholipids, lysobisphosphatidic acid (LBPA), semi-lysobisphosphatidic acid (semi-LBPA), cardiolipin, lipids bearing cationic polymers, alkyl phosphonates, alkyl phosphinates, and alkyl phosphites.

In one embodiment, the phosphatidylcholine is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine, and distearoylphosphatidylcholine; wherein the phosphatidylethanolamine is selected from the group consisting of dipalmitoylphosphatidylethanolamine and dioleoylphosphatidylethanolamine; wherein the sphingolipid is sphingomyelin; wherein the glycolipid is selected from the group consisting of ganglioside GM1 and ganglioside GM2; wherein in the lipids bearing polymers the polymer is selected from the group consisting of polyethyleneglycol, chitin, hyaluronic acid and polyvinylpyrrolidone; wherein the sterol aliphatic acid esters are selected from the group consisting of cholesterol sulfate, cholesterol butyrate, cholesterol isobutyrate, cholesterol palmitate, cholesterol stearate, lanosterol acetate, ergosterol palmitate, and phytosterol n-butyrate; wherein the sterol esters of sugar acids are selected from the group consisting of cholesterol glucuronide, lanosterol glucuronide, 7-dehydrocholesterol glucuronide, ergosterol glucuronide, cholesterol gluconate, lanosterol gluconate, and ergosterol gluconate; wherein the esters of sugar acids and the esters of sugar alcohols are selected from the group consisting of lauryl glucuronide, stearoyl glucuronide, myristoyl glucuronide, lauryl gluconate, myristoyl gluconate, and stearoyl gluconate; wherein the esters of sugars and the esters of aliphatic acids are selected from the group consisting of sucrose laurate, fructose laurate, sucrose palmitate, sucrose stearate, glucuronic acid, gluconic acid, accharic acid, and polyuronic acid; wherein the saponins are selected from the group consisting of sarsasapogenin, smilagenin, hederagenin, oleanolic acid, and digitoxigenin; wherein the glycerol esters are selected from the group consisting of glycerol tripalmitate, glycerol distearate, glycerol tristearate, glycerol dimyristate, glycerol and trimyristate; wherein the alcohols are of 10-30 carbon length and are selected from the group consisting of n-decyl alcohol, lauryl alcohol, myristyl alcohol, cetyl alcohol, and n-octadecyl alcohol; wherein in the lipids bearing cationic polymers the cationic polymers are selected from the group consisting of polylysine and polyarginine.

In another embodiment, the lipid is selected from the group consisting of dipalmitoylphosphatidylcholine, dipaimitoylphosphatidylethanolamine, and dipalmitoylphosphatidic acid.

In another embodiment, the pharmaceutical agent contained within the liposome comprises biomolecules and/or organic molecules. This technology can be used for both cosmetic and medicinal applications in which the objective is delivery of the active agent across membrane such as the dermal, mucosal, blood-brain barrier, or cellular membranes.

The present invention also relates to a method of treating disease by transporting macromolecules such as genes, proteins, and other biological or organic molecules across the blood-brain barrier wherein the method comprises the administration of a composition comprising anionic liposomes with or without short-chain lipids, a safe and effective amount of a macromolecular therapeutic agent contained within the liposomes and saposin C.

In further embodiments, the instant invention features compositions comprising a small nucleic acid molecule, such as short interfering nucleic acid (siNA), a short interfering RNA (siRNA), a double-stranded RNA (dsRNA), microRNA (mRNA), or a short hairpin RNA (shRNA), admixed or complexed with, or conjugated to, a saposin fusogenic membrane or liposome.

The present invention also relates to a method by which neuroblastoma, cerebral inflammation, metachromatic leukodystrophy (MLD), Niemann-Pick, stroke, Parkinson's, Alzheimer's diseases, demyelination disorders, retinal neuropathy, Huntington's disease, A.L.S., multiple sclerosis, neuro-AIDS, brain cancer, brain or spinal cord trauma, autism, lysosomal storage disorders, fragile X syndrome, inherited ataxias, and blindness can be treated in which the method comprises the steps of making a liposomal delivery system in which the liposome is comprised of acidic long-chain lipids, with or without the addition of neutral long-chain lipids and neutral short-chain lipids, and saposin C, prosaposin, as well as other proteins, polypeptide analogues or polypeptides derived from saposin C or prosaposin. The liposome can contain therapeutic agents such as anti-inflammatory agents, anti-apoptotic, and neuroprotective agents, or enzymes, proteins, or the corresponding genes, DNA or RNA sequences for genes identified as lacking in these diseases.

In one embodiment, compositions and methods are provided comprising a polynucleotide, or a precursor thereof, in combination with fusogenic anionic phospholipid membranes or liposomes, a fusogenic protein or polypeptide derived from prosaposin, and a pharmaceutically acceptable carrier.

In one embodiment, compositions and methods are provided comprising a short interfering nucleic acid (siNA), or a precursor thereof, in combination with fusogenic anionic phospholipid membranes or liposomes, a fusogenic protein or polypeptide derived from prosaposin, and a pharmaceutically acceptable carrier. Within the novel compositions of the invention, the siNA may be admixed or complexed with, or conjugated to, the fusogenic anionic phospholipid membranes or liposomes with a fusogenic protein or polypeptide derived from prosaposin to form a composition that enhances intracellular delivery of the siNA.

The present invention also comprises a method for treating Gaucher's Disease, wherein the method comprises the administration of a composition comprising anionic liposomes, a safe and effective amount of acid beta-glucosidase contained within the liposomes; and saposin C, all contained in a pharmaceutically acceptable carrier, wherein the pH of the composition is about 7, 6.8, 6.5, 6, 5.9, 5.8, 5.7, 5.6, 5.5, 5.4, 5.3, 5.2, 5.1, 5.0 or less and the saposin C is associated with the surface of the liposome through an electrostatic and hydrophobic interaction. Generally, the concentration of the liposome is about a 1 to 10-fold excess to that of saposin C. In one embodiment, the pH of the composition is less than about 6.8. In another embodiment, the pH of the composition is less than about 6.0. In another embodiment, the pH of the composition is less than about 5.5. In another embodiment, the pH of the composition is less than about 5.0.

The present invention also relates to a method for treating Peyer's patches, mesenteric lymph nodes, bronchial lymph nodes wherein the method comprises the administration of a composition comprising anionic long-chain lipids, long-chain neutral lipids and/or neutral short-chain lipids, a safe and effective amount of lipid, DNA or protein antigens, saposin C, prosaposin, as well as other proteins, polypeptide analogues or polypeptides derived from saposin C or prosaposin.

The present invention also relates to a method of imaging tissues and cells wherein the composition is comprised of a saposin-C containing liposome and a detectable imaging agent selected from the group consisting of MRI detectable agents, fluorescent agents, CT/PET detectable agents, agents having multiple detection properties, or combinations thereof. The agent can be either intercalated into the lipid membrane or encapsulated within the liposome. In another embodiment of the present invention, the saposin C liposomal complex can incorporate one, two or three distinct agents having different imaging properties such that multiple, distinct detection methods can be used with a single administration of saposin C liposomes.

Other ancillary agents include fluorophores (such as fluorescein, dansyl, quantum dots, and the like) and infrared dyes or metals may be used in optical or light imaging (e.g., confocal microscopy and fluorescence imaging).

In another embodiment, the composition further comprises a radionuclide, a chelating agent, biotin, a fluorophore, an antibody, horseradish peroxidase, alkaline phosphatase, nanoparticles, quantum dots, nanodroplets of anticancer agents, anticancer agents or chemotherapeutic agents, liposomal drugs, cytokines or small molecule toxins attached thereto.

In another embodiment, the imaging moiety is selected from the group consisting of a radionuclide, biotin, a fluorophore, an antibody, horseradish peroxidase, alkaline phosphatase, nanoparticles, quantum dots, nanodroplets of detectable anticancer agents, liposomal drugs and cytokines.

One of ordinary skill is familiar with methods for attaching radionuclides, chelating agents, and chelating agent-linker conjugates to the ligands of the present invention. In particular, attachment of radionuclides, chelating agents, and chelating agent-linker conjugates to the ligands of the present invention can be conveniently accomplished using, for example, commercially available bifunctional linking groups (generally heterobifunctional linking groups) that can be attached to a functional group present in a non-interfering position on the compound and then further linked to, for example, a radionuclide, chemotherapeutic agent, anticancer agent, nanoparticle, quantum dot, nanodroplet of an anticancer agent or a small molecule toxin. In this manner, the compounds of the present invention can be used to carry suitable agents to a target site, generally, a tumor or organ or tissue having cancerous cells. In another embodiment, a ligand Qdot complex Is prepared by incubating biotinylated ligand with streptavidin-Qdot605 (Quantum Dot Corp.; Hayward, Calif.).

In one embodiment of this invention, the liposome containing a traceable imaging agent can be used to target tumors such as neuroblastoma, allowing for determination of tumor size, growth, location or metastasis.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Throughout this document, all temperatures are given in degrees Celsius, and all percentages are weight percentages unless otherwise stated. All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

BRIEF DESCRIPTION OF THE DRAWINGS

This invention, as defined in the claims, can be better understood with reference to the following drawings. The drawings are not necessarily to scale, emphasis instead being placed upon clearly illustrating principles of the present invention.

FIG. 3: A schematic of the functional organization of the neuritogenic, acid β- glucosidase activation and lipid binding properties of saposin C (SEQ ID No. 17). Except for the box indicating the predicated turn and the disulfide bonds, the figure is not meant to represent known physical structure. The residues from 22-32 are of major significance to the neurotrophic effect. The region spanning residues 42-61 is critical to the acid β-glucosidase activation effects of saposin C, and the presence of all three disulfide bonds is also important for this function. In addition, higher order structure is required to have full activities of saposin C. Lipid/lipid membrane interaction regions are located at both $NH_2$— and COOH-terminal regions.

FIGS. 7A and 7B show PTIR-271 uptake as delivered by SapC-DOPS liposomes. FIGS. 7C and 7D show PTIR-316 uptake in as delivered by SapC-DOPS liposomes. Control liposomes (treated with SapC-DOPS liposomes without PTIR-271 or PTIR-316) are shown in FIGS. 7E and 7F. Red images represent uptake of dyes. Visualized using Zeiss Axiovert-ApoTome Microscope (63× and 40× oil lens): $\lambda_{EX}/\lambda_{EM}$; Beam splitter: 660; B/W phase contrast for cell morphology. Axiovision software used for imaging.

FIGS. 9A and 9C represent GFP22 siRNA containing liposomes; FIGS. 9B and 9D represent negative controls in which a non-silencing siRNA (consisting of a 22 nucleotide double-stranded RNA fragment) that does not affect GFP expression was used. All RNA was purchased from QIAGEN.

Figure 1:
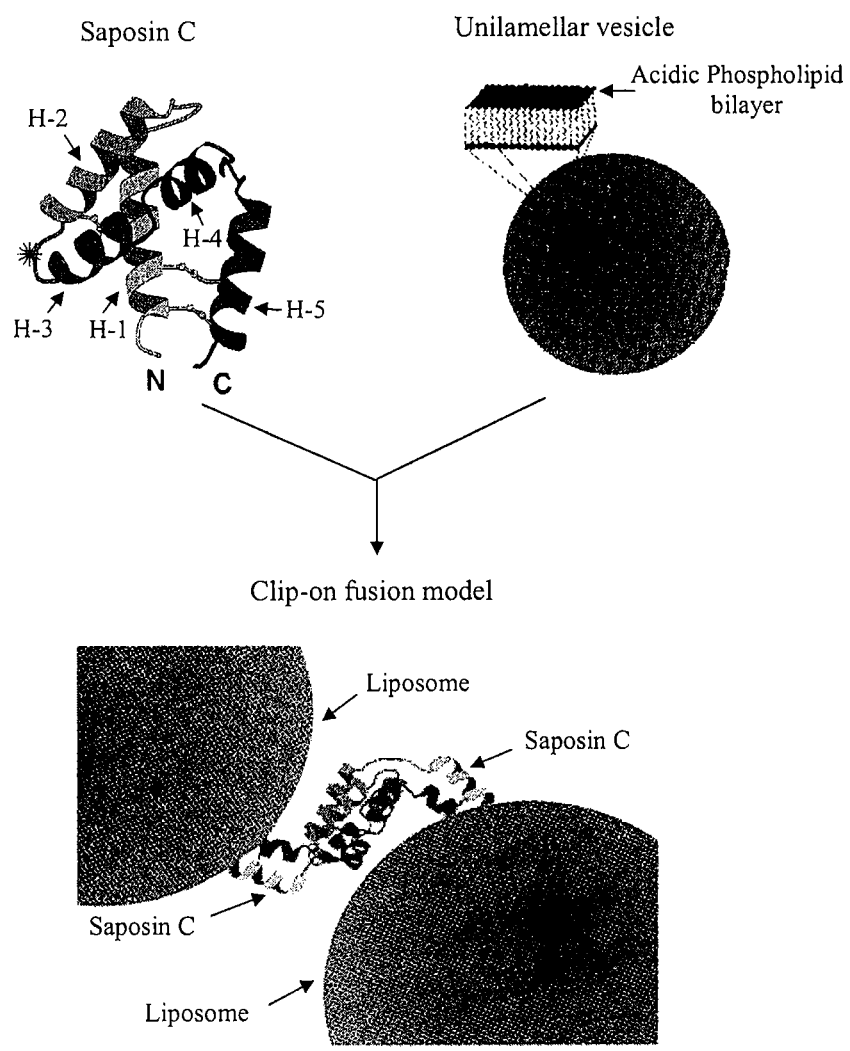
FIG. 1: Clip-on model for saposin C induced fusion: Liposome-bound saposin Cs clip one to another through hydrophobic interaction, and induce liposome fusion.

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

DETAILED DESCRIPTION OF THE INVENTION

Before the present compositions and methods are described, it is to be understood that this invention is not limited to the specific methodology, devices, and formulations as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Definitions

The terms "administered" and "administration" refer generally to the administration to a patient of a biocompatible material, including, for example, lipid and/or vesicle compositions and flush agents. Accordingly, "administered" and "administration" refer, for example, to the injection into a blood vessel of lipid and/or vesicle compositions and/or flush agents. The terms "administered" and "administration" can also refer to the delivery of lipid and/or vesicle compositions and/or flush agents to a region of interest.

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "amphipathic lipid" means a molecule that has a hydrophilic "head" group and hydrophobic "tail" group and has membrane-forming capability.

As used herein, the terms "anionic phospholipid membrane" and "anionic liposome" refer to a phospholipid membrane or liposome that contains lipid components and has an overall negative charge at physiological pH.

"Anionic phospholipids" means phospholipids having negative charge, including phosphate, sulphate and glycerol-based lipids.

"Bioactive agent" refers to a substance which may be used in connection with an application that is therapeutic or diagnostic in nature, such as in methods for diagnosing the presence or absence of a disease in a patient and/or in methods for the treatment of disease in a patient. As used herein, "bioactive agent" refers also to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including nucleosides, nucleotides and polynucleotides.

The term "contained (with)in" refers to a pharmaceutical agent being enveloped within a phospholipid membrane, such that the pharmaceutical agent is protected from the outside environment. This term may be used interchangeably with "encapsulated."

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

The term "fusogenic protein or polypeptide" as used herein refers to a protein or peptide that when added to two separate bilayer membranes can bring about their fusion into a single membrane. The fusogenic protein forces the cell or model membranes into close contact and causes them to fuse.

The words "insertion" or "addition," as used herein, refer to changes in an amino acid or nucleotide sequence resulting in the addition of one or more amino acid residues or nucleotides, respectively, to the sequence found in the naturally occurring molecule.

The terms "lipid" and "phospholipid" are used interchangeably and to refer to structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, vesicles, lipid ribbons or sheets. In the preferred embodiment, the lipid is an anionic liposome. The lipids may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

"Lipid composition" refers to a composition which comprises a lipid compound, typically in an aqueous medium. Exemplary lipid compositions include suspensions, emulsions and vesicle compositions. "Lipid formulation" refers to a lipid composition which also comprises a bioactive agent.

"Liposome" refers to a generally spherical cluster or aggregate of amphipathic compounds, including lipid compounds, typically in the form of one or more concentric layers, for example, bilayers. They may also be referred to herein as lipid vesicles.

The term "long-chain lipid" refers to lipids having a carbon chain length of about 13, 14, 15, 16, 17, 18, 19, 20, 21, 22, 23 or 24. In one embodiment, the chain length is selected from a chain length of 18, 19, or 20. Examples of lipids that may be used with the present invention are available on the website for Avanti Polar Lipids, Inc. Representative examples of long chain lipids that may be used with the present invention include, but are not limited to the following lipids: [0094] 14:0 PS1,2-Dimyristoyl-sn-Glycero-3-[Phospho-L-Serine] (Sodium Salt) (DMPS); 16:0 PS 1,2-Dipalmitoyl-sn-Glycero-3-[Phospho-L-Serine] (Sodium Salt) (DPPS); 17:0 PS1,2-Diheptadecanoyl-sn-Glycero-3-[Phospho-L-Serine] (Sodium Salt); 18:0 PS1,2-Distearoyi-sn-Glycero-3-[Phospho-L-Serine] (Sodium Salt) (DSPS); 18:1 PS1,2-Dioleoyl-sn -Glycero-3-[Phospho-L-Serine] (Sodium Salt) (DOPS); 18:2 PS1,2-Dilinoleoyl-sn-Glycero-3-[Phospho-L-Serine] (Sodium Salt); 20:4 PS1,2-Diarachidonoyl-sn-Glycero-3-[Phospho-L-Serine] (Sodium Salt); 22:6 PS1,2-Didocosahexaenoyl-sn-Glycero-3-[Phospho-L-Serine] (Sodium Salt); 16:0-18:1 PS1-Palmitoyl-2-Oleoyl-sn-Glycero-3-[Phospho-L-Serine] (Sodium Salt) (POPS); 16:0-18:2 PS1-Palmitoyl-2-Linoleoyl-sn-Glycero-3-[Phospho-L-Serine] (Sodium Salt); 16:0-22:6 PS1-Palmitoyl-2-Docosahexaenoyl-sn-Glycero-3-[Phospho-L-Serine] (Sodium Salt); 18:0-18:1 PS1-Stearoyl-2-Oleoyl-sn-Glycero-3-[Phospho-L-Serine] (Sodium Salt); 18:0-18:2 PS1-Stearoyl-2-Linoleoyl-sn-Glycero-3-[Phospho-L-Serine] (Sodium Salt); 18:0-20:4 PS1-Stearoyl-2-Arachidonoyl-sn-Glycero-3-[Phospho-L-Serine] (Sodium Salt); 18:0-22:6 PS 1-Stearoyl-2-Docosahexaenoyl-sn-Glycero-3-[Phospho-L-Serine] (Sodium Salt); 16:0 PC 1,2-Dipalmitoyl-sn -Glycero-3-Phosphocholine (DPPC); 17:0 PC 1,2-Diheptadecanoyl-sn-Glycero-3-Phosphocholine; 18:0 PC 1,2-Distearoyl-sn-Glycero-3-Phosphocholine (DSPC); 16:1 PC(C is) 1,2-Dipalmitoleoyl -sn-Glycero-3-Phosphocholine; 16:1 Trans PC 1,2-Dipalmitelaidoyl-sn-Glycero-3-Phosphocholine; 18:1 PC Delta6 (cis) 1,2-Dipetroselinoyl-sn-Glycero-3-Phosphocholine; 18:2 PC (cis) 1,2-Dilinoleoyl-sn-Glycero-3-Phosphocholine; 18:3 PC (cis) 1,2-Dilinolenoyl-sn-Glycero-3-Phosphocholine; 20:1 PC (cis) 1,2-Dieicosenoyl-sn-Glycero-3-Phosphocholine; 22:1 PC (cis) 1,2-Dierucoyl-sn-Glycero-3-Phosphocholine; 22:0 PC 1,2-Dibehenoyl-sn-Glycero-3-Phosphocholine; 24:1 PC (cis) 1,2-Dinervonoyl-sn-Glycero-3-Phosphocholine; 16:0-18:0 PC 1-Palmitoyl-2-Stearoyl -sn-Glycero-3-Phosphocholine; 16:0-18:1 PC 1-Palmitoyl-2-Oleoyl-sn-Glycero-3-Phosphocholine; 16:0-18:2 PC 1-Palmitoyl-2-Linoleoyl-sn-Glycero-3-Phosphocholine; 18:0-18:1 PC 1-Stearoyl-2-Oleoyl-sn-Glycero-3-Phosphocholine; 18:0-18:2 PC 1-Stearoyl-2-Linoleoyl-sn-Glycero-3-Phosphocholine; 18:1-18:0 PC 1-Oleoyl-2-Stearoyl-sn-Glycero-3-Phosphocholine; 18:1-16:0 PC 1-Oleoyl-2-Palmitoyl-sn-Glycero-3-Phosphocholine; 18:0-20:4 PC 1-Stearoyl-2-Arachidonyl-sn -Glycero-3-Phosphocholine; 16:0-18:1 PG 1-Palmitoyl-2-Oleoyl-sn-Glycero-3-[Phospho-rac-(1-glycerol)] (Sodium Salt) (POPG); 18:1 PG 1,2-Dioleoyl-sn-Glycero-3-[Phospho-rac-(1-glycerol)] (Sodium Salt) (DOPG); 18:1 PA 1,2-Dioleoyl-sn-Glycero-3-Phosphate (Monosodium Salt) (DOPA); 18:1 PI 1,2-Dioleoyl-sn-Glycero-3-Phosphoinositol (Ammonium Salt); 16:0(D31)-18:1 PI 1-Palmitoyl(D31)-2-Oleoyl-sn-Glycero-3-Phosphoinositol (Ammonium Salt); 18:1 PE 1,2-Dioleoyl-sn-Glycero-3-Phosphoethanolamine (DOPE); 18:2 PE 1,2-Dilinoleoyl-sn-Glycero-3-Phosphoethanolamine.

The phrases "nucleic acid" or "nucleic acid sequence," as used herein, refer to a nucleotide, oligonucleotide, polynucleotide, or any fragment thereof. A "nucleic acid" refers to a string of at least two base-sugar-phosphate combinations. (A polynucleotide is distinguished from an oligonucleotide by containing more than 120 monomeric units.) Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. Anti-sense is a polynucleotide that interferes with the function of DNA and/or RNA. The term nucleic acid refers to a string of at least two base-sugar-phosphate combinations. Natural nucleic acids have a phosphate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of a tRNA (transfer RNA), siRNA (short interfering ribonucleic acid), snRNA (small nuclear RNA), rRNA (ribosomal RNA), mRNA (messenger RNA), anti-sense RNA, and ribozymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), siNA (short interfering nucleic acid), phosphorothioates, and other variants of the phosphate backbone of native nucleic acids.

As used herein, the term "nucleotide-based pharmaceutical agent" or "nucleotide-based drug" refer to a pharmaceutical agent or drug comprising a nucleotide, an oligonucleotide or a nucleic acid.

"Patient" or "subject" refers to animals, including mammals, preferably humans.

As used herein, "pharmaceutical agent or drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical agent" and "drug" encompass both the inactive drug and the active metabolite.

The phrase "pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system and the precise amount of the active depends on the physical condition of the patient, progression of the illness being treated etc.

As used herein, the term "saposin" refers to the family of prosaposin-derived proteins and polypeptides, including but not limited to naturally occurring saposins A, B, C and D as well as synthetic saposin-derived proteins and peptides and peptide analogs showing fusogenic activity. The saposin C and polypeptides derived therefrom may be used in one embodiment of the invention.

The term "short chain lipid" refers to lipids having a carbon chain length of 4, 5, 6, 7, 8, 9, 10, 11 or 12. In one embodiment, the carbon chain length is 6, 7, 8, 9 or 10. In one embodiment, the carbon chain length is 6, 7 or 8. Examples of negative short chain lipids are available at the website for Avanti Polar Lipids, Inc. Examples of short chain lipids that may be used with the present invention include, but are not limited to, the following: 06:0 PS (DHPS) 1,2-Dihexanoyl-sn-Glycero-3-[Phospho-L-Serine] (Sodium Salt); 08:0 PS1, 2-Dioctanoyl-sn-Glycero-3-[Phospho-L-Serine] (Sodium Salt); 03:0 PC 1,2-Dipropionoyl-sn -Glycero-3-Phosphocholine; 04:0 PC 1,2-Dibutyroyl-sn-Glycero-3-Phosphocholine; 05:0 PC 1,2-Divaleroyl-sn-Glycero-3-Phosphocholine; 06:0 PC (DHPC) 1,2-Dihexanoyl-sn-Glycero-3-Phosphocholine; 07:0 PC 1,2-Diheptanoyl-sn-Glycero-3-Phosphocholine; 08:0 PC 1,2-Dioctanoyl -sn-Glycero-3-Phosphocholine; 09:0 PC 1,2-Dinonanoyl-sn-Glycero-3-Phosphocholine; 06:0 PG 1,2-Dihexanoyl-sn-Glycero-3-[Phospho-rac-(1-glycerol)] (Sodium Salt); 08:0 PG 1,2-Dioctanoyl -sn-Glycero-3-[Phospho-rac-(1-glycerol)] (Sodium Salt); 06:0 PA 1,2-Dihexanoyl-sn-Glycero-3-Phosphate (Monosodium Salt); 08:0 PA 1,2-Dioctanoyl-sn-Glycero-3-Phosphate (Monosodium Salt); 06:0 PE 1,2-Dihexanoyl-sn-Glycero-3-Phosphoethanolamine; 08:0 PE 1,2-Dioctanoyl-sn -Glycero-3-Phosphoethanolamine.

As used herein, the term "short interfering nucleic acid", "siNA", "short interfering RNA", "siRNA", "short interfering nucleic acid molecule", "short interfering oligonucleotide molecule", or "chemically-modified short interfering nucleic acid molecule", refers to any nucleic acid molecule capable of inhibiting or down regulating gene expression or viral replication, for example by mediating RNA interference "RNAi" or gene silencing in a sequence-specific manner. Within exemplary embodiments, the siNA is a double-stranded polynucleotide molecule comprising self-complementary sense and antisense regions, wherein the antisense region comprises a nucleotide sequence that is complementary to a nucleotide sequence in a target nucleic acid molecule for down regulating expression, or a portion thereof, and the sense region comprises a nucleotide sequence corresponding to (i.e., which is substantially identical in sequence to) the target nucleic acid sequence or portion thereof. "siNA" means a small interfering nucleic acid, for example a siRNA, that is a short-length double-stranded nucleic acid (or optionally a longer precursor thereof), and which is not unacceptably toxic in target cells. The length of useful siNAs within the invention will in certain embodiments be optimized at a length of approximately 21 to 23 bp long. However, there is no particular limitation in the length of useful siNAs, including siRNAs. For example, siNAs can initially be presented to cells in a precursor form that is substantially different than a final or processed form of the siNA that will exist and exert gene silencing activity upon delivery, or after delivery, to the target cell. Precursor forms of siNAs may, for example, include precursor sequence elements that are processed, degraded, altered, or cleaved at or following the time of delivery to yield a siNA that is active within the cell to mediate gene silencing. Thus, in certain embodiments, useful siNAs within the invention will have a precursor length, for example, of approximately 100-200 base pairs, 50-100 base pairs, or less than about 50 base pairs, which will yield an active, processed siNA within the target cell. In other embodiments, a useful siNA or siNA precursor will be approximately 10 to 49 bp, 15 to 35 bp, or about 21 to 30 bp in length.

"Vesicle" refers to a spherical entity which is generally characterized by the presence of one or more walls or membranes which form one or more internal voids. Vesicles may be formulated, for example, from lipids, including the various lipids described herein, proteinaceous materials, polymeric materials, including natural, synthetic and semi-synthetic polymers, or surfactants. Preferred vesicles are those which comprise walls or membranes formulated from lipids. In these preferred vesicles, the lipids may be in the form of a monolayer or bilayer, and the mono- or bilayer lipids may be used to form one or more mono- or bilayers. In the case of more than one mono- or bilayer, the mono- or bilayers may be concentric. Lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Similarly, the vesicles prepared from proteins or polymers may comprise one or more concentric walls or membranes. The walls or membranes of vesicles prepared from proteins or polymers may be substantially solid (uniform), or they may be porous or semi-porous. The vesicles described herein include such entities commonly referred to as, for example, liposomes, micelles, bubbles, microbubbles, microspheres, lipid-, polymer-protein- and/or surfactant-coated bubbles, microbubbles and/or micro spheres, microballoons, aerogels, clathrate bound vesicles, and the like. The internal void of the vesicles may be filled with a liquid (including, for example, an aqueous liquid), a gas, a gaseous precursor, and/or a solid or solute material, including, for example, a targeting ligand and/or a bioactive agent, as desired.

Fusogenic Proteins or Polypeptides

In one embodiment, the present invention provides for phopholipid membranes comprising one or more lysosomal fusogenic protein or polypeptide. In another embodiment, the one or more lysosomal fusogenic protein or polypeptide is contained within anionic liposomes. In another embodiment, the anionic liposomes further comprise a pharmaceutical agent.

Suitable lysosomal fusogenic proteins and polypeptides for use in this invention include, but are not limited to, proteins of the saposin family, for example, saposin C. Also included are homologues of saposin C, wherein the homologue possesses at least 80% sequence homology, due to degeneracy of the genetic code which encodes for saposin C, and polypeptides and peptide analogues possessing similar biological activity as saposin C.

Examples of peptides or peptide analogues include:

```
                                            (SEQ. ID. No.1)
Ser-Asp-Val-Tyr-Cys-Glu-Val-Cys-Glu-Phe-Leu-Val-
Lys-Glu-Val-Thr-Lys-Leu-Ile-Asp-Asn-Asn-Lys-Thr-
Glu-Lys-Glu-Ile-Leu-Asp-Ala-Phe-Asp-Lys-Met-Cys-
Ser-Lys-Leu-Pro;

(SEQ. ID. No.2)
Val-Tyr-Cys-Glu-Val-Cys-Glu-Phe-Leu-Val-Lys-Glu-
Val-Thr-Lys-Leu-Ile-Asp-Asn-Asn-Lys-Thr-Glu-Lys-
Glu-Ile-Leu-Asp-Ala-Phe-Asp-Lys-Met-Cys-Ser-Lys-
Leu-Pro,
``` and derivatives, analogues, homologues, fragments and mixtures thereof.

Also included are polypeptides of the formula:

```
h-u-Cys-GlU-h-Cys-Glu-h-h-h-Lys-Glu-h-u-Lys-h-h-
Asp-Asn-Lys-u-Glu-Lys-Glu-h-h-Asp-h-h-Asp-Lys-h-
Cys-u-Lys-h-h,
``` where h=hydrophobic amino acids, including, Val, Leu, Ile, Met, Pro, Phe, and Ala; and u=uncharged polar amino acids, including, Thr, Ser, Tyr, Gly, Gln, and Asn.

Suitable lysosomal fusogenic proteins and polypeptides for use in this invention include, but are not limited to, proteins of the saposin family, preferably saposin C. Also included are homologues of saposin C, wherein the homologue possesses at least 80% sequence homology, due to degeneracy of the genetic code which encodes for saposin C, and polypeptides and peptide analogues possessing similar biological activity as saposin C.

As used herein, term "peptide analog" refers to a peptide which differs in amino acid sequence from the native peptide only by conservative amino acid substitutions, for example, substitution of Leu for Val, or Arg for Lys, etc., or by one or more non-conservative amino acid substitutions, deletions, or insertions located at positions which do not destroy the biological activity of the peptide (in this case, the fusogenic property of the peptide). A peptide analog, as used herein, may also include, as part or all of its sequence, one or more amino acid analogues, molecules which mimic the structure of amino acids, and/or natural amino acids found in molecules other than peptide or peptide analogues.

By "analogs" is meant substitutions or alterations in the amino acid sequences of the peptides of the invention, which substitutions or alterations do not adversely affect the fusogenic properties of the peptides. Thus, an analog might comprise a peptide having a substantially identical amino acid sequence to a peptide provided herein as SEQ ID NO:1 and 2 and in which one or more amino acid residues have been conservatively substituted with chemically similar amino acids. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated.

Phospholipid Membrane and Formation of Liposomes

This invention utilizes an anionic phospholipid membrane to effect the saposin-mediated membrane fusion for delivery of a particular pharmaceutical or imaging agent across either a dermal or mucosal membrane or across the blood-brain barrier or other cellular membranes. These anionic phospholipid membranes are generally used for preparing liposomes. Liposomes are microscopic vesicles consisting of concentric lipid bilayers and, as used herein, refer to small vesicles composed of amphipathic lipids arranged in spherical bilayers. Structurally, liposomes range in size and shape from long tubes to spheres, with dimensions from a few hundred angstroms to fractions of a millimeter. Regardless of the overall shape, the bilayers are generally organized as closed concentric lamellae, with an aqueous layer separating each lamella from its neighbor. Vesicle size normally falls in a range of between about 20 and about 30,000 nm in diameter.

The liquid film between lamellae is usually between about 3 and 10 nm. A variety of methods for preparing various liposome forms have been described in the periodical and patent literature. For specific reviews and information on liposome formulations, reference is made to reviews by Pagano and Weinstein (see Ann. Rev. Biophysic. Bioeng., 7, 435-68 (1978) and Ann. Rev. Biophysic. Bioeng., 9, 467-508 (1980)).

In one embodiment, the anionic phospholipid membrane is a vesicle. In another embodiment, the vesicle is a liposome. The liposomes are a form of nanocontainer and nanocontainers, such as nanoparticles or liposomes, are commonly used for encapsulation of drugs. The liposomes preferably have mean diameters of about 200 nanometers. In another embodiment, the liposomes have a mean diameter of between 50 and 350 nanometers. In another embodiment, the liposomes have a mean diameter of between 150 and 250 nanometers.

Specific delivery of liposomes to a target tissue such as a proliferating cell mass, neoplastic tissue, inflammatory tissue, inflamed tissue, and infected tissue can be achieved by selecting a liposome size appropriate for delivering a therapeutic agent to said target tissue. For example, liposomes with a mean diameter of 180 nm may not accumulate in a solid tumor; liposomes with a mean diameter of 140 nm accumulate in the periphery of the same solid tumor, and liposomes with a mean diameter of 110 nm accumulate in the peripheral and central portions of that solid tumor.

In connection with embodiments involving vesicle compositions, the size of the vesicles can be adjusted for the particular intended end use including, for example, diagnostic and/or therapeutic use. The size of the vesicles may preferably range from about 30 nanometers (nm) to about 300 micrometers (μm) in diameter, and all combinations and subcombinations of ranges therein. More preferably, the vesicles have diameters of from about 100 nm to about 10 μm, with mean diameters of from about 200 nm to about 7 μm being even more preferred. In connection with particular uses, for example, intravascular use, including magnetic resonance imaging of the vasculature, it may be preferred that the vesicles be no larger that about 30 μm in diameter, with smaller vesicles being preferred, for example, vesicles of no larger than about 12 μm in diameter. In certain preferred embodiments, the diameter of the vesicles may be about 7 μm or less, with vesicles having a mean diameter of about 5 μm or less being more preferred, and vesicles having a mean diameter of about 3 μm or less being even more preferred.

The size of the liposomes can be adjusted, if desired, by a variety of procedures including, for example, shaking, microemulsification, vortexing, extrusion, filtration, sonication, homogenization, repeated freezing and thawing cycles, extrusion under pressure through pores of defined size, and similar methods.

In addition to, or instead of, the lipid, proteinaceous and/or polymeric compounds discussed above, the compositions described herein may comprise one or more stabilizing materials. Exemplary of such stabilizing materials are, for example, biocompatible polymers. The stabilizing materials may be employed to desirably assist in the formation of vesicles and/or to assure substantial encapsulation of the gases or gaseous precursors. Even for relatively insoluble, non-diffusible gases, such as perfluoropropane or sulfur hexafluoride, improved vesicle compositions may be obtained when one or more stabilizing materials are utilized in the formation of the gas and gaseous precursor filled vesicles. These compounds may help improve the stability and the integrity of the vesicles with regard to their size, shape and/or other attributes.

The terms "stable" or "stabilized", as used herein, means that the vesicles may be substantially resistant to degradation, including, for example, loss of vesicle structure or encapsulated gas or gaseous precursor, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and gaseous precursor filled vesicles, may also be stable even under adverse conditions, such as temperatures and pressures which are above or below those experienced under normal ambient conditions.

The stability of the vesicles described herein may be attributable, at least in part, to the materials from which the vesicles are made, including, for example, the lipids, polymers and/or proteins described above, and it is often not necessary to employ additional stabilizing materials, although it is optional and may be preferred to do so. Such additional stabilizing materials and their characteristics are described more fully hereinafter.

The materials from which the vesicles are constructed are preferably biocompatible lipid, protein or polymer materials, and of these, the biocompatible lipids are preferred. In addition, because of the ease of formulation, including the capability of preparing vesicles immediately prior to administration, these vesicles may be conveniently made on site.

The biocompatible polymers useful as stabilizing materials for preparing the gas and gaseous precursor filled vesicles may be of natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, lucose, mannose, gulose, idose, galactose, talose, erytirulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthalate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of vesicles which employ polymers as stabilizing compounds will be readily apparent to those skilled in the art, once armed with the present disclosure, when the present disclosure is coupled with information known in the art, such as that described and referred to in U.S. Pat. No. 5,205,290, the disclosures of which are hereby incorporated herein by reference, in their entirety.

In general, the liposomes utilized in the present invention can be divided into three categories based on their overall size and the nature of the lamellar structure (see New York Academy Sciences Meeting, "Liposomes and Their Use in Biology and Medicine," of December 1977). The four classifications include multi-lamellar vesicles (MLV's), small uni-lamellar vesicles (SUV's), large uni-lamellar vesicles (LUV's) and giant unilamellar vesicles (GUV's). SUVs and LUVs, by definition, have only one bilayer, whereas MLVs contain many concentric bilayers. Spherical unilamellar vesicles (ULV) with a low polydispersity can spontaneously form in charged phospholipid mixtures. The formation of such low-polydispersity ULV usually requires a process of abrupt increase in temperature or sudden dilution. In some cases, the spontaneous low-polydispersity ULVs have been examined to be highly stable over time and upon dilution, which illustrates a great potential to be encapsulating carriers for drug delivery or gene therapy. See Nieh, et al. *Low-Polydispersity Phospholipid Unilamellar Ellipsoidal Vesicles and Their Interaction with Helical Domains of Saposin C.*, Manuscript.

Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart an overall neutral charge, phosphate and sulfate based lipids contribute a negative charge, glycerol-based lipids are generally negatively-charged, and sterols are generally neutral in solution but have charged groups. The lipids used in the present invention are both anionic and neutral lipids.

A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., Chemistry and Physics of Lipids, 1990 53, 37-46, the disclosures of which are hereby incorporated herein by reference in their entirety. Suitable freeze-thaw techniques are described, for example, in International Application Ser. No. PCT/US89/05040, filed Nov. 8, 1989, the disclosures of which are incorporated herein by reference in their entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug (Crescent Dental, Lyons, Ill.), a Mixomat, sold by Degussa AG, Frankfurt, Germany, a Capmix, sold by Espe Fabrik Pharmazeutischer Praeparate GMBH & Co., Seefeld, Oberay Germany, a Silamat Plus, sold by Vivadent, Lechtenstein, or a Vibros, sold by Quayle Dental, Sussex, England. Conventional microemulsification equipment, such as a Microfluidizer (Microfluidics, Woburn, Mass.) may also be used.

Spray drying may be also employed to prepare the vesicles. Utilizing this procedure, the lipids may be pre-mixed in an aqueous environment and then spray dried to produce gas-filled vesicles. The vesicles may be stored under a headspace of a desired gas.

Many liposomal preparatory techniques which may be adapted for use in the preparation of vesicle compositions are discussed, for example, in U.S. Pat. No. 4,728,578; U.K. Patent Application GB 2193095 A; U.S. Pat. Nos. 4,728,575; 4,737,323; International Application Ser. No. PCT/US85/01161; Mayer et al., Biochimica et Biophysica Acta, Vol. 858, pp. 161-168 (1986); Hope et al., Biochimica et Biophysica Acta, Vol. 812, pp. 55-65 (1985); U.S. Pat. No. 4,533,254; Mayhew et al., Methods in Enzymology, Vol. 149, pp. 64-77 (1987); Mayhew et al., Biochimica et Biophysica Acta, Vol 755, pp. 169-74 (1984); Cheng et al, Investigative Radiology, Vol. 22, pp. 47-55 (1987); International Application Ser. No. PCT/US89/05040; U.S. Pat. Nos. 4,162,282; 4,310,505; 4,921,706; and Liposome Technology, Gregoriadis, G., ed., Vol. 1, pp. 29-31, 51-67 and 79-108 (CRC Press Inc., Boca Raton, Fla. 1984), the disclosures of each of which are hereby incorporated by reference herein, in their entirety.

Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and inorganic mercurial salts. Such sterilization, which may also be achieved by other conventional means, such as by irradiation, will be necessary where the stabilized vesicles are used for imaging under invasive circumstances, e.g., intravascularly or intraperitonealy. The appropriate means of sterilization will be apparent to the artisan based on the present disclosure.

As with the preparation of lipid and/or vesicle compositions, a wide variety of techniques are available for the preparation of lipid formulations. For example, the lipid and/or vesicle formulations may be prepared from a mixture of lipid compounds, protein and bioactive agents. In this case, lipid compositions are prepared as described above in which the compositions also comprise bioactive agent. Thus, for example, micelles can be prepared in the presence of a bioactive agent.

As those skilled in the art will recognize, any of the lipid and/or vesicle compositions and/or lipid and/or vesicle formulations may be lyophilized for storage, and reconstituted, for example, with an aqueous medium (such as sterile water, phosphate buffered solution, or aqueous saline solution), with the aid of vigorous agitation. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

In general, the lipid mixtures of the present invention are comprised of anionic long-chain lipids. In one embodiment, the lipid mixture used to synthesize saposin C-containing liposomes is comprised of 1) anionic long-chain lipids, 2) neutral long-chain lipids, and 3) short-chain lipids. The short chain lipids may be either neutral or anionic.

In another embodiment, the lipid mixture is comprised only of anionic long-chain lipids and neutral or anionic short-chain lipids. The following table illustrates examples of combinations of phospholipids that may be used to synthesize liposomes containing saposin C such that the objects of the present invention are achieved. Saposin C or a polypeptide of Saposin C may be added to the following combinations of lipids using the methods described herein. The following Table 1 illustrates combinations of phospholipids that may be used to practice the present invention. The examples are not exhaustive, but are intended to illustrate possible embodiments of the present invention.

Table 1

TABLE 1

Combinations of Long Chain and Short Chain Phospholipids that may be used in combination with Saposin C or polypeptides of Saposin C to form fusogenic-protein-containing Liposomes in Accordance with the Present Invention.

| Long-Chain Phospholipid | | Short-Chain Phospholipid |
|---|---|---|
| 18:1 PS | 18:0 PC | 06:0 PC (DHPC) |
| 18:1 PS | | 06:0 PC (DHPC) |
| 18:1 PS | 18:0 PC | 06:0 PS (DHPS) |
| 18:1 PS | | 06:0 PS (DHPS) |
| 18:2 PS | 18:1 PG | 06:0 PS (DHPS) |
| 18:0-18:1 PS | 18:1 PE | 06:0 PC (DHPC) |
| 16:0 PS | 16:1 PC | 05:0 PC |
| 20:4 PS | 20:1 PC | 07:0 PC |

The presence of saposin C protein in the liposomal complex has been observed to destabilize and restructure the liposomal membrane, resulting in a limited shelf life for liposomal delivery systems utilizing this protein. See Mu-Ping Nieh et al., *Low-Polydispersity Phospholipid Unilamellar Ellipsoidal Vesicles and Their Interaction with Helical Domains of Saposin C;* 2005. The present invention addresses this problem. One embodiment of the present invention includes the use of at least one type of short-chain lipid. Addition of a short-chain lipid results in stabilization of the membrane and an increase in liposome shelf-life, increasing the utility and availability of liposomal-based therapeutics.

One example of a lipid mixture used to synthesize saposin-C liposomes is one that includes the negatively charged lipid dioleoylphosphatidylserine (DOPS) wherein a small amount of the neutral long chain lipid dipalmitoyl phosphatidylcholine (DPPC) and the neutral short-chain lipid dihexanoyl phosphatidycholine (DHPC) is added. See for example, Nieh et al., *Low-Polydispersity Phospholipid Unilamellar Ellipsoidal Vesicles and Their Interaction with Helical Domains of saposin C*, manuscript. Any lipid known in the art corresponding in charge and length may be used. Samples containing this composition of lipids doped with small amount of saposin C do not destabilize, but large aggregates can precipitate out of the solution for the system with a higher concentration of saposin C, indicating destabilization of the membrane. The DOPS/DPPC/DHPC samples are stable over a period of 24 months, indicating that the addition of the neutral long chain lipids and short chain lipids enhance the stability of the aggregates. However, any combination of long and short chain lipids may be used in accordance with the invention as described herein.

The negative long chain lipids of the present invention may be any long chain phospholipid that has a carbon chain about 14 to about 24 carbons in length, or about 18 to about 20 carbons in length. An exhaustive list of lipids is available at the website for Avanti Polar Lipids, Inc. One skilled in the art will appreciate which lipids can be used in the present invention. While any combination of long and short chain lipids may be used, some combinations yield more stable liposomes. For example, while not intending to limit the present invention, the following may guide selection of the composition from which liposomes are formed: where long-chains of about 20 to about 24 carbons in length are used, short-chain lipids having lengths of about 6 to about 8 may be used for improved liposome stability. Where long-chain lengths of about 14 to about 18 are used, short-chain lipids having lengths of about 6 to about 7 may be used for improved liposome stability. While these combinations of lipids yield more stable liposomes, other combinations may successfully be used, and are not intended to be disclaimed. Table 2 illustrates examples of phospholipid combinations that may be used to generate more stable liposomes. These examples, however, are not meant to imply that other combinations of phospholipids may not be used with the present invention.

Table 2

TABLE 2

Examples of Combinations of Long and Short-Chain Phosholipids that may be used with the Present Invention, based on Phospholipid Chain Length. The present invention is not limited to the following combinations.

| Long-Chain Phospholipid Length (Number of Carbons) | Short-Chain Phospholipid Length (Number of Carbons) |
|---|---|
| 14 to 24 | 4 to 8 |
| 16 to 22 | 5 to 7 |
| 18 to 20 | 6 to 7 |
| 20 to 24 | 7 to 8 |
| 14 to 18 | 4 to 6 |

Further, the presence or absence of saturating hydrocarbons on the lipid chain effect liposome stability. For example, lipids having chain lengths of about 18 or greater are used, the phospholipid may be saturated or unsaturated, preferably unsaturated. For shorter long-chain lipids such as those having about 14 to about 16 carbons, the lipid may be unsaturated, but use of saturated lipids yields improved performance of the present invention.

Examples of appropriate lipid ratios are as follows. The molar ratio of the selected neutral phospholipid to the selected negative phospholipid in the composition is about 1 to 10 (about 10% neutral phospholipids), or about 1 to 5 (about 20% neutral phospholipids), or about 1 to 1 (50% neutral phospholipids). The molar ratio of the selected long-chain phospholipid to the selected short-chain lipid in the composition is about 4 to 1 (about 20% short-chain), and can be about 10 to 1 (10% short-chain) to about 3 to 1 (about 33% short-chain). One example of the long-chain to short chain ratio in one embodiment is as follows: [neutral long-chain lipid]+[acidic long-chain lipid])/[neutral short-chain lipid] is about 4. As another example, in one embodiment, the molar ratio of DOPS to DPPC in the mixture ranges from about 10-8 to 1, or about 7-6 to 1, or about 5-3 to 1 or about 1-2 to 1, with ([DPPC]+[DOPS])/DHPC=about 4. Appropriate lipids for use in the present invention may be selected from any lipids known in the art or as provided at www.avantilipids.com.

Table 3

TABLE 3

Hydrodynamic radii (nm) from DLS data of DOPS/DPPC/DHPC aggregates in solution, where [DOPS] + [DPPC])/DHPC = 4.
Only the sample with DOPS/DPPC = 10 shows a bimodal distribution.

| DOPS/DPPC Ratio | Duration (Day) | $R_H$ nm (%) | | |
|---|---|---|---|---|
| | | 1-100 | 100-200 | 400-800 |
| 1 | 1 | 40 (79) | 145 (12) | 441 (9) |
| 1 | 40 | 42 (76) | 173 (7) | 705 (17) |
| 5 | 1 | 29 (78) | 157 (11) | 570 (11) |
| 5 | 40 | None | 147 (51) | 689 (49) |
| 10 | 1 | None | 138 (70) | 582 (30) |
| 10 | 40 | None | 178 (56) | 746 (44) |
| 10 | 240 | None | 161 (49) | 452 (51) |
| 10 | 365 | None | 159 (51) | 471 (49) |

In order for many drugs to have therapeutic potential, it is necessary for them to be delivered to the proper location in the body, and the drugs must have the capability to access the necessary tissues. Liposomes can form the basis for sustained drug release and delivery to specific cell types, or parts of the body. The therapeutic use of liposomes also includes the delivery of drugs which are normally toxic in the free form. In the liposomal form, the toxic drug is occluded, and may be directed away from the tissues sensitive to that drug and targeted to selected areas. Liposomes can also be used therapeutically to release drugs over a prolonged period of time, reducing the frequency of administration. In addition, liposomes can also provide a method for forming aqueous dispersions of hydrophobic or amphiphilic drugs, which are normally unsuitable for intravenous delivery.

The liposomes of the present invention may comprise one or more pharmaceutical agent and/or imaging agent that have been trapped in the aqueous interior or between bilayers, or by trapping hydrophobic molecules within the bilayer. Several techniques can be employed to use liposomes to target encapsulated drugs to selected host tissues, and away from sensitive tissues. These techniques include manipulating the size of the liposomes, their net surface charge, and their route of administration.

The liposomes of the present invention may also be delivered by a passive delivery route. Passive delivery of liposomes involves the use of various routes of administration, e.g., intravenous, subcutaneous, intramuscular and topical. Each route produces differences in localization of the liposomes.

The liposomes of the present invention are also ideal for delivery of therapeutic or imaging agents across the blood-brain barrier. The present invention relates to a method by which liposomes containing therapeutic agents can be used to deliver these agents to the CNS wherein the agent is contained within a liposome comprised of the above referenced lipids and saposin C, prosaposin or a variant of saposin. The liposome containing a therapeutic agent can be administered via IV injection, IM injection, trans-nasal delivery, or any other transvascular drug delivery method, using generally accepted methods in the art.

Without intending to be limited by theory, one possible mechanism as to how saposin-mediated membrane fusion occurs is through protein conformational changes. Of the pro-saposin derived proteins, saposin A and saposin C show the highest degree of amino acid identity/similarity. Computationally, both proteins are predicted to fold into amphipathic helical bundle motifs. In general, the saposin-fold is a common super secondary structure with five amphipathic α-helices folded into a single globular domain and is common to both proteins. In one embodiment, the folding is along a centrally located helix at amino-terminal, against which helices 2 and 3 are packed from one side and helices 4 and 5 from the other side. This fold may provide an interface for membrane interaction.

Figure 2:
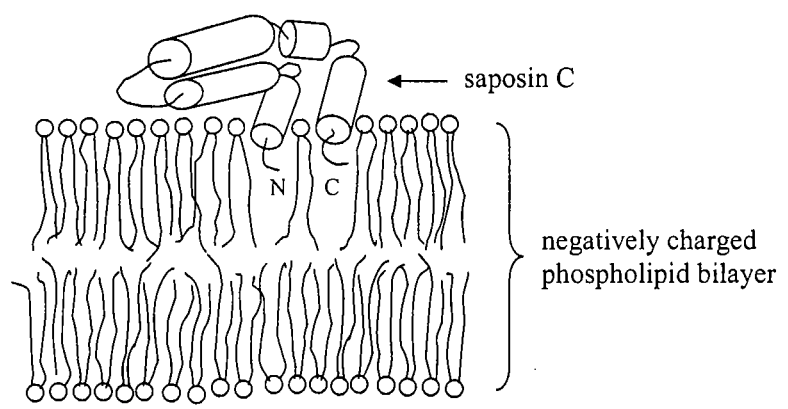
FIG. 2: Saposin C and liposome vesicle association: A conformational alteration of the saposin-fold found in lipid-bound saposin C. Membrane Topological interaction of saposin C indicated that amphipathic helices at amino- and carboxyl-termini were embedded into the lipid bilayer and the middle region of saposin C is exposed to aqueous phase. The middle region of saposin C is exposed to the aqueous phase.

A mechanism for saposin-mediated membrane fusion with anionic phospholipid membranes is thought to be a two-step process. In the first step, electrostatic interactions between the positively charged amino acids (basic form), lysine (Lys) and arginine (Arg), of the saposins and the negatively charged phospholipid membrane results in an association between these two species (see FIG. 1). In the second step, intramolecular hydrophobic interactions between the helices of two adjacent saposin proteins brings the two membranes in close enough proximity for fusion of the membranes to take place (see FIG. 2).

Thus, in accordance with the present invention, the association of saposins, and in particular saposin C, with a lipid generally requires a pH range from about 5.5 or less since the initial association of saposin C with the membrane arises through an electrostatic interaction of the positively charged basic amino acid residues of saposin C with the anionic membrane. Thus, it is highly desirable to have the basic amino acids exist in their protonated forms in order to achieve a high number of electrostatic interactions.

Alternatively, related fusion proteins and peptides derived from the saposin family of proteins may not have this lower pH range limitation and thus the pH range of other membrane fusion proteins and peptides can range from physiological pH (pH of about 7) to lower pH ranges.

Bioactive Agents

In accordance with the present invention, bioactive agents, e.g., pharmaceutical agents, are contained within the anionic phospholipid membrane or liposome for saposin-mediated transport within and/or beneath the dermal and mucosal membranes or across the blood-brain barrier or other cellular membranes. The active agents may be large biomolecules including, but not limited to, lipids, in particular ceramides, steroids, fatty acids, triacylglycerols, genes and proteins, DNA, RNA or siRNA. The active agent may also be comprised of small organic molecules. As used herein, "pharmaceutical agent" means any material or mixture of materials which provides a cosmetic or therapeutic benefit when delivered via saposin C liposomes.

Exemplary bioactive agents or drugs that may be delivered by the system of the present invention may include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, corticoids (steroids), antidepressants, depressants, diagnostic aids, diuretics, enzymes, expectorants, hormones, hypnotics, minerals, nutritional supplements, parasympathomimetics, potassium supplements, sedatives, sulfonamides, stimulants, sympathomimetics, tranquilizers, urinary antiinfectives, vasoconstrictors, vasodilators, vitamins, xanthine derivatives, and the like.

Digitalis Drugs

Preferred examples of pharmaceutical agents include the digitalis drugs, such as digoxin, digitoxin, digoxigenin, and digitoxigenin. These drugs are all primarily used as cardiac agents.

Steroidal Compounds

Steroidal compounds form another preferred class of pharmaceutical agent. An example of a steroidal pharmaceutical agent is testosterone (17 beta-hydroxyandrost-4-en-3-one), the principal male steroid. Its main therapeutic use is in the treatment of deficient endocrine function of the testes. Estradiol (estra-1,3,5(10)-triene-3,17 beta-diol) is also a preferred steroidal pharmaceutical agent. Estradiol and its ester derivatives are indicated for the treatment of symptoms of menopause and other conditions that cause a deficiency of endogenous estrogen production. Progesterone is also a preferred steroidal pharmaceutical agent. Progesterone is used primarily to suppress or synchronize estrus as well as to control habitual abortion and diagnose and treat menstrual disorders. Additional preferred steroidal pharmaceutical agents include 3-hydroxy-5 alpha-pregnan-20-one, 3-beta-hydroxy-pregn-5-ene-20-one and related compounds.

Nonsteroidal Anti-Inflammatory Drugs (NSAID's)

Examples of NSAID's includes piroxicam (4-hydroxy-2-methyl-N-2-pyridinyl-2H-1,2-benzothiazine-3-carboxamide 1,1-dioxide), diclofenac, ibuprofen, ketoprofen, meperidine, propoxyphene, nalbuphine, pentazocine, buprenorphine, aspirin, indomethacin, diflunisal, acetaminophen, naproxen, fenoprofen, piroxicam, sulindac, tolmetin, meclofenamate, zomepirac, penicillamine, phenylbutazone, oxyphenbutazone, chloroquine, hydroxychloroquine, azathiaprine, cyclophosphamide, levamisole, prednisone, prednisolone, betamethasone, triamcinolone, and methylprednisolone and indomethacin (1-(4-chlorobenzoyl)-5-methoxy-2-methyl-1H-indole-3-acetic acid).

Amino Acid-Based Drugs

Protein and peptide-based drugs, as well as other amino acid-based drugs, may also be used as pharmaceutical agents according to the present invention. The problems associated with conventional delivery strategies for protein and peptide drugs are widely appreciated. Oral administration of these drugs is generally impractical due to degradation and non-absorption in the gastrointestinal tract. Thus, the parenteral route remains the principal delivery route.

Amino acid-based drugs, such as the cephalosporins, will typically have molecular weight less than about 5000, and preferably, less than about 2500, and more preferably, less than about 1000. Protein and peptide drugs typically have a molecular weight of at least about 100 daltons, and more typically a molecular weight in the range of about 200 to 40,000 daltons. Examples of peptides and proteins in this size range include, but are not limited to luteinizing hormone-releasing hormone, somatostatin, bradykinin, goserelin, somatotropin, buserelin, platelet-derived growth factor, triptorelin, gonadorelin, asparaginase, nafarelin, bleomycin sulfate, leuprolide, chymopapain, growth hormone-releasing factor, parathyroid hormone (PTH), cholecystokinin, chorionic gonadotropin, insulin, corticotropin (ACTH), calcitonin erythropoietin, glucagon, hyaluronidase, interferons, e.g., alpha, interleukins, e.g., IL-1 thyrotropin-releasing hormone, menotropins, pituitary hormones (e.g., urofollitropin (Follicle hGH, hMG, hCG, FSH, etc.), melanocyte-stimulating hormone, gonadotropin releasing hormone, oxytocin, vasopressin, streptokinase, tissue plasminogen activator, angiotensin ii antagonists, bradykinin potentiatorB, bradykinin antagonists, bradykinin potentiator C, enkephalins, insulin-like growth factors, prostaglandin antagonists, tumor necrosis factor, epidermal growth factor (egf), amylin, lipotropin, and thyroid stimulating hormone.

An example of a preferred peptide pharmaceutical agent is parathyroid hormone (PTH) (see Harper et al., Eds., Review of Physiological Chemistry, 16th Ed., Lange Medical Publications, Los Altos, Calif. (1977) p. 468). Also, a fragment consisting of about 34 amino acid residues from the N-terminal has been isolated and found to display the full biological activity of PTH (see Potts et al., in Parathyroid Hormone and Thyrocalcitonin (Calcitonin), R. V. Talmage, et al., Eds. Excerpta Medica, New York (1968)). The sequence of the polypeptide varies slightly among mammalian species. According to the present invention, PTH is meant to include human parathyroid hormone, as well as the other variants and the 34 amino acid fragment. PTH serves as a regulatory factor in the homeostatic control of calcium and phosphate metabolism (see, e.g., Parsons, et al. "Physiology and Chemistry of Parathyroid Hormone" in Clinics in Endocrinology and Metabolism, I. MacIntyre, Ed. Saunders, Philadelphia (1972) pp. 33-78). The main therapeutic use for PTH is in the treatment of osteoporosis. PTH has also been used as a blood calcium regulator.

In one embodiment, calcitonin is also a preferred peptide pharmaceutical agent. Calcitonin is a polypeptide containing 32 amino acid residues (see Harper et al., Eds., Review of Physiological Chemistry, 16th Ed., Lange Medical Publications, Los Altos, Calif. (1977), p. 469). According to the present invention, calcitonin is meant to include all calcitonin, including that of humans, mammals, and fish, as well as other variants. Calcitonin is a calcium regulating hormone and has been used in the treatment of osteoporosis, hypercalcemia, and Paget's disease.

An additional preferred protein drug is the cytokine IL-10. IL-10 is produced by the TH2 helper subset, B cell subsets and LPs-activated monocytes. IL-10 inhibits several immune functions that are relevant to the skin immune response and thus, the development of the irritation and inflammation that is sometimes associated with the transdermal delivery of drugs. More specifically, the release of IFN-alpha, which initiates the cascade of cellular activation leading to the skin's immune response, is inhibited by IL-10. IL-10 also suppresses the synthesis of numerous pro-inflammatory cytokines by macrophages, as well as the proliferation of antigen-specific T cell proliferation by down regulating class II MHC expression.

Nucleic Acid-Based Drugs

Generally, nucleic acid-based drugs have had limited success as therapeutic agents, in part, because of problems associated with their stability and delivery. Nucleotide-based pharmaceutical agents frequently contain a phosphodiester bond which is sensitive to degradation by nucleases. Such degradation would be a significant impediment to the use of an oligonucleotide or nucleic acid as a pharmaceutical agent that depends upon the integrity of the sequence for its recognition specificity. Thus, naturally occurring oligonucleotides and nucleic acids often must typically be chemically modified to render them resistant to nucleases which would degrade them in vivo, or even in vitro unless care is taken to choose appropriate conditions. However, this is not necessary using the drug delivery system of the present invention.

The nucleotide-based drugs of the present invention include aptamers, antisense compounds, and triple helix drugs. The nucleotide-based drugs typically will have a molecular weight greater than about 350 and may range up to about 100 bases. Examples of nucleotide-based drugs include di- and trinucleotides, such as GS 375, a dinucleotide analog with potential therapeutic activity against the influenza virus (Gilead Sciences, Inc., Foster City, Calif.).

In one embodiment, the nucleotide-based drug comprises one or more therapeutic genes. The therapeutic gene which is encapsulated within the liposome can be any of the common therapeutic genes which are used to express therapeutic and diagnostic agents. Exemplary therapeutic genes include brain-derived neurotrophic factor (BDNF) for treatment of neurodegenerative disease, stroke, or brain trauma; tyrosine hydroxylase and/or aromatic amino acid decarboxylase for Parkinson's disease; .beta.-glucuronidase; hexosaminidase A; herpes simplex virus thymidine kinase or genes encoding antisense RNA to the epidermal growth factor receptor for treatment of brain tumors; lysosomal storage disorder replacement enzymes for Tay-Sachs and other lysosomal storage disorders; gene encoding antisense RNA for the treatment of the cerebral component of acquired immune deficiency syndrome (AIDS). In addition to the therapeutic gene, the plasmid DNA may also contain DNA sequences either before or after the therapeutic sequence and these additional parts of the plasmid may promote tissue-specific transcription of the plasmid in a particular cell in the brain, may promote enhanced translation and/or stabilization of the mRNA of the therapeutic gene, and may enable episomal replication of the transgene in brain cells. In general, the therapeutic gene will contain at least 100 nucleotides or have a molecular weight above 30,000 Daltons. It is preferred that the therapeutic gene be contained within a plasmid or other suitable carrier for encapsulation within the internal compartment of the liposome or nanocontainer.

A therapeutic gene may be encapsulated within the liposome according to any of the well known drug encapsulation processes. For example, encapsulation by sonication, freeze/thaw, evaporation, and extrusion through membrane filters.

The number of therapeutic genes encapsulated within the liposome may vary from 1 to many, depending on the disease being treated. The limiting factor will be the diameter of therapeutic gene that is encapsulated within the liposome. Using polycationic proteins such as histone, protamine, or polylysine, it is possible to compact the size of plasmid DNA that contains several thousand nucleotides to a structure that has a diameter of 10-30 nm. The volume of a 100 diameter liposome is 1000-fold and 35-fold greater than the volume of a 10 nm and 30 nm DNA compacted sphere, respectively. Therefore, it is possible to encapsulate many copies of the same gene or multiple copies of multiple genes within the liposome.

Bioactive agents include oligomers such as (1) antisense compounds and (2) other bioactive oligomers. As used herein, the term "antisense compound" encompasses, inter alia, single stranded antisense oligonucleotides (DNA, DNA-like, RNA, RNA-like) or double stranded or self-hybridizing constructs comprising an antisense orientation oligonucleotide, antisense PNAs, ribozymes and EGSs (described infra). Antisense compounds can exert their effect by a variety of means. One such means is the antisense-mediated direction of an endogenous nuclease, such as RNase H in eukaryotes or RNase P in prokaryotes, or dsRNAases in RNAi pathways to the target nucleic acid (Chiang et al., J. Biol. Chem., 1991, 266, 18162; Forster et al., Science, 1990, 249, 783). The sequences that recruit RNase P are known as External Guide Sequences, hence the abbreviation "EGSs" (Guerrier-Takada et al., Proc. Natl. Acad. Sci. USA, 1997, 94, 8468).

Another type of bioactive oligomer is an RNA-RNA hybrid molecule that can modulate gene expression. The double strand RNA may in some instances be described as siRNA. For the purposes of describing an embodiment of this invention, an siRNA is a combination of an antisense strand and a sense strand, each of a specified length sufficient to exhibit desirable properties such as a stability and target specificity, for example from about 8-30, about 12-27, about 17-25, or about 19-23 nucleotides long. Such a complementary pair of oligonucleotides can be blunt ended or can include additional nucleotides on either or both of their 5' or 3' ends. Further they can include other molecules or molecular structures on their 3' or 5' ends such as a phosphate group on the 5' end. A preferred group of compounds of the invention include a phosphate group on the 5' end of the antisense strand compound. Other preferred compounds also include a phosphate group on the 5' end of the sense strand compound. An even further preferred compounds would include additional nucleotides such as a two base overhang on the 3' end.

The term "other bioactive oligomer" encompasses, inter alia, aptamers and molecular decoys. As used herein, the term is meant to refer to any oligonucleotide (including an RNA or PNA) that (1) provides a prophylactic, palliative or therapeutic effect to an animal in need thereof and (2) acts by a non-antisense mechanism, i.e., by some means other than by hybridizing to a nucleic acid.

In one embodiment, the bioactive agent is an aptamer or molecular decoy. Aptamers are single-stranded oligonucleotides that bind specific ligands via a mechanism other than Watson-Crick base pairing. Aptamers are typically targeted to, e.g., a protein and are not designed to bind to a nucleic acid (Ellington et al., Nature, 1990, 346, 818). Molecular decoys are short double-stranded nucleic acids (including single-stranded nucleic acids designed to "fold back" on themselves) that mimic a site on a nucleic acid to which a factor, such as a protein, binds. Such decoys are expected to competitively inhibit the factor; that is, because the factor molecules are bound to an excess of the decoy, the concentration of factor bound to the cellular site corresponding to the decoy decreases, with resulting therapeutic, palliative or prophylactic effects. Methods of identifying and constructing decoy molecules are described in, e.g., U.S. Pat. No. 5,716,780 to Edwards et al.

Another type of bioactive oligomer is an RNA-DNA hybrid molecule that can direct gene conversion of an endogenous nucleic acid (Cole-Strauss et al., Science, 1996, 273, 1386). Any of the preceding bioactive oligomers may be formulated in the liposomes of the invention and used for prophylactic or therapeutic purposes. Some embodiments of the invention, a single oligonucleotide having both the antisense portion as a first region in the oligonucleotide and the sense portion as a second region in the oligonucleotide is selected. The first and second regions are linked together by either a nucleotide linker (a string of one or more nucleotides that are linked together in a sequence) or by a non-nucleotide linker region or by a combination of both a nucleotide and non-nucleotide structure. In each of these structures, the oligonucleotide, when folded back on itself, would be complementary at least between the first region, the antisense portion, and the second region, the sense portion. Thus the oligonucleotide would have a palindrome within it structure wherein the first region, the antisense portion in the 5' to 3' direction, is complementary to the second region, the sense portion in the 3' to 5' direction.

In further embodiments, the invention includes an oligonucleotide/protein composition. This composition has both an oligonucleotide component and a protein component. The oligonucleotide component comprises at least one oligonucleotide, either the antisense or the sense oligonucleotide but preferable the antisense oligonucleotide (the oligonucleotide that is antisense to the target nucleic acid). The protein component of the composition comprises at least one protein that forms a portion of the RNA-induced silencing complex, i.e., the RISC complex. The oligonucleotide component can also comprise both the antisense and the sense strand oligonucleotides.

RISC is a ribonucleoprotein complex that contains an oligonucleotide component and proteins of the Argonaute family of proteins. While we do not wish to be bound by theory, the Argonaute proteins are a class of proteins, some of which have been shown to contain a PAZ and Piwi domain and that have been implicated in processes previously linked to post-transcriptional silencing. The Argonaute family of proteins includes, but depending on species, are not necessary limited to e1F2C1 and e1F2C2. e1F2C2 is also known as human GERp95. While we do not wish to be bound by theory, at least the antisense oligonucleotide strand is bound to the protein component to form the RISC complex. Additional, the complex might also include the sense strand oligonucleotide.

The oligomeric compounds of the invention may be used in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or proteins to effect modification of the target nucleic acid.

One non-limiting example of such a protein is the RISC complex. Use of the RISC complex to effect cleavage of RNA targets thereby greatly enhances the efficiency of oligonucleotide-mediated inhibition of gene expression. Similar roles have been postulated for other ribonucleases such as those in the RNase III and ribonuclease L family of enzymes.

In another embodiment, the oligomeric compound of the invention include a single-stranded antisense oligonucleotide that binds in a RISC complex, a double stranded antisense/sense pair of oligonucleotide or a single strand oligonucleotide that includes both an antisense portion and a sense portion. Each of these compounds or compositions is used to induce potent and specific modulation of gene function. Such specific modulation of gene function has been shown in many species by the introduction of double-stranded structures, such as double-stranded RNA (dsRNA) molecules and has been shown to induce potent and specific antisense-mediated reduction of the function of a gene or its associated gene products. This phenomenon occurs in both plants and animals and is believed to have an evolutionary connection to viral defense and transposon silencing.

Figure 8:
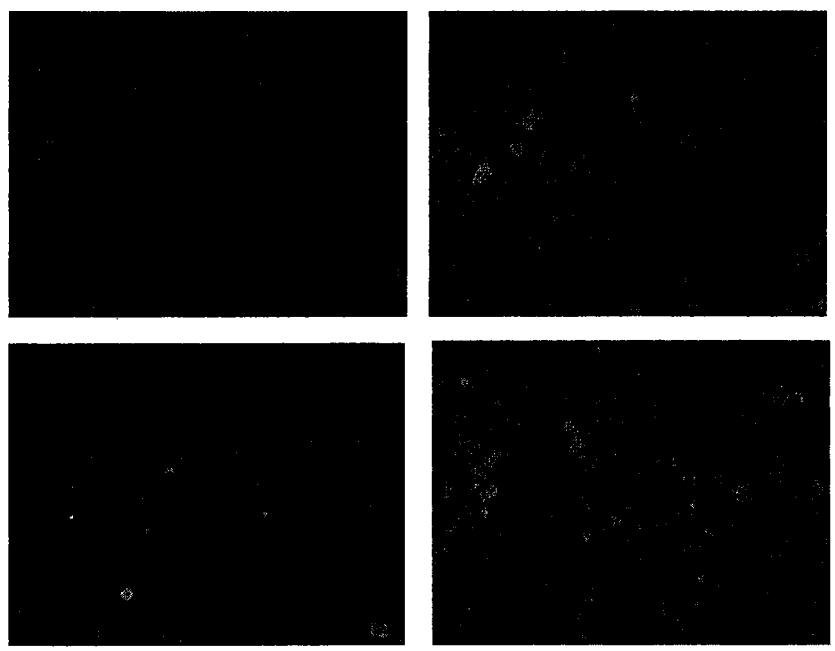
FIG. 8. Delivery of GFP22 siRNA into EGFP 4T1 cells using Sap-C-DOPS liposomes. GFP22 siRNA is a 22 nucleotide double-stranded RNA that specifically inhibits green fluorescent protein gene expression. (N J Caplen et al., PNAS, 2001, 98:9742-9747). Incubation time was 72 hours. 20×, 800 mSec exposure; Photoshop: input levels 27, 1.19, 164; output level 255. Size 3×2.29 inches.
Figure 9:
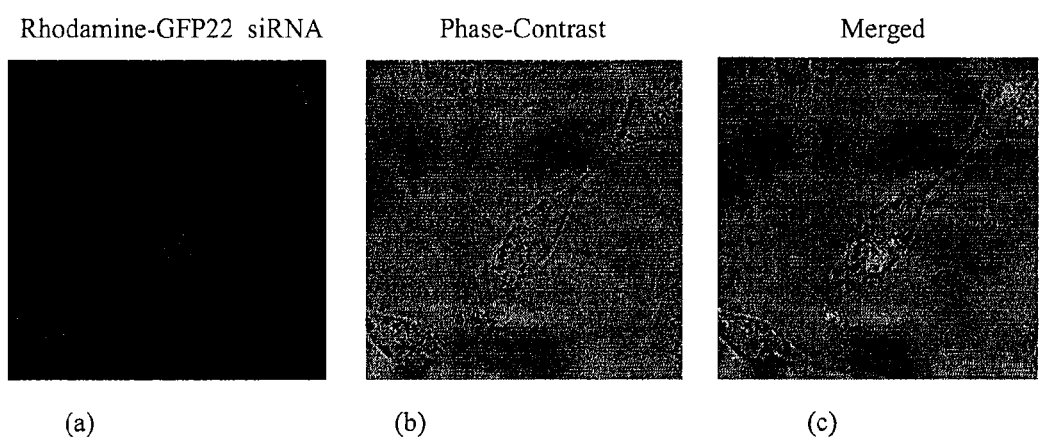
FIG. 9. Micrographs of the delivery of GFP 22 siRNA into neuroblastoma (CHLA-20) cancer cells showing (a) Rhodamine-GFP22 siRNA; (b) Phase-Contrast; and (c) merged.

Aptamers (or nucleic acid antibody) are single- or double-stranded DNA or single-stranded RNA molecules that bind specific molecular targets. Generally, aptamers function by inhibiting the actions of the molecular target, e.g., proteins, by binding to the pool of the target circulating in the blood. Examples of aptamers include Gilead's antithrombin inhibitor GS 522 and its derivatives (Gilead Science, Foster City, Calif.; see also Macaya et al. (1993) Proc. Natl. Acad. Sci. USA 90:3745-9; Bock et al. (1992) Nature (London) 355: 564-566; and Wang et al. (1993) Biochem. 32:1899-904). Similarly, siRNA (small interfering RNA molecules) as known in the art may be used with the present invention. See FIGS. 8 and 9.

For diseases that result from the inappropriate expression of genes, specific prevention or reduction of the expression of such genes represents an ideal therapy. In principle, production of a particular gene product may be inhibited, reduced or shut off by hybridization of a single-stranded deoxynucleotide or ribodeoxynucleotide complementary to an accessible sequence in the mRNA, or a sequence within the transcript which is essential for pre-mRNA processing, or to a sequence within the gene itself. This paradigm for genetic control is often referred to as antisense or antigene inhibition.

Antisense compounds are oligonucleotides that are designed to bind and disable or prevent the production of the mRNA responsible for generating a particular protein. Antisense compounds can provide a therapeutic function by inhibiting in vivo the formation of one or more proteins that cause or are involved with disease. Antisense compounds complementary to certain gene messenger RNA or viral sequences have been reported to inhibit the spread of disease related to viral and retroviral infectious agents (see, for example, Matsukura et al. (1987) Proc. Natl. Acad. Sci. USA 84:7706, and references cited therein). Others have reported that oligonucleotides can bind to duplex DNA via triple helix formation and inhibit transcription and/or DNA synthesis.

Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide (see Ching et al. Proc. Natl. Acad. Sci. U.S.A. 86:10006-10010 (1989); Broder et al. Ann. Int. Med. 113:604-618 (1990); Loreau et al. FEBS Letters 274:53-56 (1990)).

Triple helix compounds (also referred to as triple strand drugs) are oligonucleotides that bind to sequences of double-stranded DNA and are intended to inhibit selectively the transcription of disease-causing genes, such as viral genes, e.g., HIV and herpes simplex virus, and oncogenes, i.e., they stop protein production at the cell nucleus. These drugs bind directly to the double stranded DNA in the cell's genome to form a triple helix and thus, prevents the cell from making a target protein (see, for example U.S. Pat. No. 5,176,996, Hogan et al, Jan. 5, 1993).

The site specificity of oligonucleotides (e.g., antisense compounds and triple helix drugs) is not significantly affected by modification of the phosphodiester linkage or by chemical modification of the oligonucleotide terminus. Consequently, these oligonucleotides can be chemically modified; enhancing the overall binding stability, increasing the stability with respect to chemical degradation, increasing the rate at which the oligonucleotides are transported into cells, and conferring chemical reactivity to the molecules. The general approach to constructing various oligonucleotides useful in antisense therapy has been reviewed by vander Krol et al. (1988) Biotechniques 6:958-976 and Stein et al. (1988) Cancer Res. 48:2659-2668.

Accordingly, aptamers, antisense compounds and triple helix drugs also can include nucleotide substitutions, additions, deletions, or transpositions, so long as specific hybridization to or association with the relevant target sequence is retained as a functional property of the oligonucleotide. For example, some embodiments will employ phosphorothioate analogs which are more resistant to degradation by nucleases than their naturally occurring phosphate diester counterparts and are thus expected to have a higher persistence in vivo and greater potency (see, Campbell et al. (1990) J. Biochem. Biophys. Methods 20:259-267). Phosphoramidate derivatives of oligonucleotides also are known to bind to complementary polynucleotides and have the additional capability of accommodating covalently attached ligand species and will be amenable to the methods of the present invention (see Froehler et al. (1988) Nucleic Acids Res. 16(11): 4831).

In addition, nucleotide analogs, for example where the sugar or base is chemically modified, can be employed in the present invention. Analogous forms of purines and pyrimidines are those generally known in the art, many of which are used as chemotherapeutic agents.

Terminal modification also provides a useful procedure to modify cell type specificity, pharmacokinetics, nuclear permeability, and absolute cell uptake rate for oligonucleotide pharmaceutical agents. For example, substitutions at the 5' and 3' ends include reactive groups which allow covalent crosslinking of the nucleotide-based pharmaceutical agent to other species and bulky groups which improve cellular uptake (see Oligodeoxynucleotides: Antisense Inhibitors of Gene Expression, (1989) Cohen, Ed., CRC Press; Prospects for Antisense Nucleic Acid Therapeutics for Cancer and AIDS, (1991), Wickstrom, Ed., Wiley-Liss; Gene Regulation: Biology of Antisense RNA and DNA, (1992) Erickson and Izant, Eds., Raven Press; and Antisense RNA and DNA, (1992), Murray, Ed., Wiley-Liss. For general methods relating to antisense compounds, see Antisense RNA and DNA, (1988), D. A. Melton, Ed., Cold Spring Harbor Laboratory, Cold Spring Harbor, N.Y.).

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. The polynucleotide can be a sequence whose presence or expression in a cell alters the expression or function of cellular genes or RNA. A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Polynucleotides may contain an expression cassette coded to express a whole or partial protein, or RNA. An expression cassette refers to a natural or recombinantly produced polynucleotide that is capable of expressing a sequence. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences. The polynucleotide may contain sequences that do not serve a specific function in the target cell but are used in the generation of the polynucleotide. Such sequences include, but are not limited to, sequences required for replication or selection of the polynucleotide in a host organism.

In certain embodiments of the invention, as noted above, saposin fusogenic membranes or liposomes are used to facilitate delivery of larger nucleic acid molecules than conventional siNAs, including large nucleic acid precursors of siNAs. For example, the methods and compositions herein may be employed for enhancing delivery of larger nucleic acids that represent "precursors" to desired siNAs, wherein the precursor amino acids may be cleaved or otherwise processed before, during or after delivery to a target cell to form an active siNA for modulating gene expression within the target cell. For example, a siNA precursor polynucleotide may be selected as a circular, single-stranded polynucleotide, having two or more loop structures and a stem comprising self-complementary sense and antisense regions, wherein the antisense region comprises a nucleotide sequence that is complementary to a nucleotide sequence in a target nucleic acid molecule or a portion thereof, and the sense region having nucleotide sequence corresponding to the target nucleic acid sequence or a portion thereof, and wherein the circular polynucleotide can be processed either in vivo or in vitro to generate an active siNA molecule capable of mediating RNAi.

In mammalian cells, dsRNAs longer than 30 base pairs can activate the dsRNA-dependent kinase PKR and 2'-5'-oligoadenylate synthetase, normally induced by interferon. The activated PKR inhibits general translation by phosphorylation of the translation factor eukaryotic initiation factor 2.alpha. (eIF2.alpha.), while 2'-5'-oligoadenylate synthetase causes nonspecific mRNA degradation via activation of RNase L. By virtue of their small size (referring particularly to non-precursor forms), usually less than 30 base pairs, and most commonly between about 17-19, 19-21, or 21-23 base pairs, the siNAs of the present invention avoid activation of the interferon response.

In contrast to the nonspecific effect of long dsRNA, siRNA can mediate selective gene silencing in the mammalian system. Hairpin RNAs, with a short loop and 19 to 27 base pairs in the stem, also selectively silence expression of genes that are homologous to the sequence in the double-stranded stem. Mammalian cells can convert short hairpin RNA into siRNA to mediate selective gene silencing.

RISC mediates cleavage of single stranded RNA having sequence complementary to the antisense strand of the siRNA duplex. Cleavage of the target RNA takes place in the middle of the region complementary to the antisense strand of the siRNA duplex. Studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) has been reported to be tolerated.

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity.

Alternatively, the siNAs can be delivered as single or multiple transcription products expressed by a polynucleotide vector encoding the single or multiple siNAs and directing their expression within target cells. In these embodiments the double-stranded portion of a final transcription product of the siRNAs to be expressed within the target cell can be, for example, 15 to 49 bp, 15 to 35 bp, or about 21 to 30 bp long. Within exemplary embodiments, double-stranded portions of siNAs, in which two strands pair up, are not limited to completely paired nucleotide segments, and may contain nonpairing portions due to mismatch (the corresponding nucleotides are not complementary), bulge (lacking in the corresponding complementary nucleotide on one strand), overhang, and the like. Nonpairing portions can be contained to the extent that they do not interfere with siNA formation. In more detailed embodiments, a "bulge" may comprise 1 to 2 nonpairing nucleotides, and the double-stranded region of siNAs in which two strands pair up may contain from about 1 to 7, or about 1 to 5 bulges. In addition, "mismatch" portions contained in the double-stranded region of siNAs may be present in numbers from about 1 to 7, or about 1 to 5. Most often in the case of mismatches, one of the nucleotides is guanine, and the other is uracil. Such mismatching may be attributable, for example, to a mutation from C to T, G to A, or mixtures thereof, in a corresponding DNA coding for sense RNA, but other cause are also contemplated. Furthermore, in the present invention the double-stranded region of siNAs in which two strands pair up may contain both bulge and mismatched portions in the approximate numerical ranges specified.

The terminal structure of siNAs of the invention may be either blunt or cohesive (overhanging) as long as the siNA retains its activity to silence expression of target genes. The cohesive (overhanging) end structure is not limited only to the 3' overhang as reported by others. On the contrary, the 5' overhanging structure may be included as long as it is capable of inducing a gene silencing effect such as by RNAi. In addition, the number of overhanging nucleotides is not limited to reported limits of 2 or 3 nucleotides, but can be any number as long as the overhang does not impair gene silencing activity of the siNA. For example, overhangs may comprise from about 1 to 8 nucleotides, more often from about 2 to 4 nucleotides. The total length of siNAs having cohesive end structure is expressed as the sum of the length of the paired double-stranded portion and that of a pair comprising overhanging single-strands at both ends. For example, in the exemplary case of a 19 bp double-stranded RNA with 4 nucleotide overhangs at both ends, the total length is expressed as 23 bp. Furthermore, since the overhanging sequence may have low specificity to a target gene, it is not necessarily complementary (antisense) or identical (sense) to the target gene sequence. Furthermore, as long as the siNA is able to maintain its gene silencing effect on the target gene, it may contain low molecular weight structure (for example a natural RNA molecule such as tRNA, rRNA or viral RNA, or an artificial RNA molecule), for example, in the overhanging portion at one end.

In addition, the terminal structure of the siNAs may have a stem-loop structure in which ends of one side of the double-stranded nucleic acid are connected by a linker nucleic acid, e.g., a linker RNA. The length of the double-stranded region (stem-loop portion) can be, for example, 15 to 49 bp, often 15 to 35 bp, and more commonly about 21 to 30 bp long. Alternatively, the length of the double-stranded region that is a final transcription product of siNAs to be expressed in a target cell may be, for example, approximately 15 to 49 bp, 15 to 35 bp, or about 21 to 30 bp long. When linker segments are employed, there is no particular limitation in the length of the linker as long as it does not hinder pairing of the stem portion. For example, for stable pairing of the stem portion and suppression of recombination between DNAs coding for this portion, the linker portion may have a clover-leaf tRNA structure. Even if the linker has a length that would hinder pairing of the stem portion, it is possible, for example, to construct the linker portion to include introns so that the introns are excised during processing of a precursor RNA into mature RNA, thereby allowing pairing of the stem portion. In the case of a stem-loop siRNA, either end (head or tail) of RNA with no loop structure may have a low molecular weight RNA. As described above, these low molecular weight RNAs may include a natural RNA molecule, such as tRNA, rRNA or viral RNA, or an artificial RNA molecule.

The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., Cell., 110: 563-574 (2002) and Schwarz et al., Molecular Cell, 10: 537-568 (2002), or 5',3'-diphosphate.

As used herein, the term siNA molecule is not limited to molecules containing only naturally-occurring RNA or DNA, but also encompasses chemically-modified nucleotides and non-nucleotides. In certain embodiments, the short interfering nucleic acid molecules of the invention lack 2'-hydroxy (2'-OH) containing nucleotides. In certain embodiments short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions.

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (mRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

In other embodiments, siNA molecules for use within the invention may comprise separate sense and antisense sequences or regions, wherein the sense and antisense regions are covalently linked by nucleotide or non-nucleotide linker molecules, or are alternately non-covalently linked by ionic interactions, hydrogen bonding, van der waals interactions, hydrophobic interactions, and/or stacking interactions.

"Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. These antisense and sense RNAs have been conventionally synthesized with an RNA synthesizer. As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo. Optionally, the siRNA include single strands or double strands of siRNA.

An siHybrid molecule is a double-stranded nucleic acid that has a similar function to siRNA. Instead of a double-stranded RNA molecule, an siHybrid is comprised of an RNA strand and a DNA strand. Preferably, the RNA strand is the antisense strand as that is the strand that binds to the target mRNA. The siHybrid created by the hybridization of the DNA and RNA strands have a hybridized complementary portion and preferably at least one 3' overhanging end.

siNAs for use within the invention can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs). The antisense strand may comprise a nucleotide sequence that is complementary to a nucleotide sequence in a target nucleic acid molecule or a portion thereof, and the sense strand may comprise a nucleotide sequence corresponding to the target nucleic acid sequence or a portion thereof. Alternatively, the siNA can be assembled from a single oligonucleotide, where the self-complementary sense and antisense regions of the siNA are linked by means of a nucleic acid-based or non-nucleic acid-based linker(s).

Within additional embodiments, siNAs for intracellular delivery according to the methods and compositions of the invention can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof, and the sense region comprises a nucleotide sequence corresponding to the target nucleic acid sequence or a portion thereof.

Non-limiting examples of chemical modifications that can be made in an siNA include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, are shown to preserve RNAi activity in cells while at the same time, dramatically increasing the serum stability of these compounds.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

The siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

An siNA molecule may be comprised of a circular nucleic acid molecule, wherein the siNA is about 38 to about 70 (e.g., about 38, 40, 45, 50, 55, 60, 65, or 70) nucleotides in length having about 18 to about 23 (e.g., about 18, 19, 20, 21, 22, or 23) base pairs wherein the circular oligonucleotide forms a dumbbell shaped structure having about 19 base pairs and 2 loops.

A circular siNA molecule contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

Modified nucleotides present in siNA molecules, preferably in the antisense strand of the siNA molecules, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, Principles of Nucleic Acid Structure, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides. 2'-deoxy-2'-chloro nucleotides, 2'-azido nucleotides, and 2'-O-methyl nucleotides.

The sense strand of a double stranded siNA molecule may have a terminal cap moiety such as an inverted deoxybasic moiety, at the 3'-end, 5'-end, or both 3' and 5'-ends of the sense strand.

A siNA further may be further comprised of a nucleotide, non-nucleotide, or mixed nucleotide/non-nucleotide linker that joins the sense region of the siNA to the antisense region of the siNA. In one embodiment, a nucleotide linker can be a linker of >2 nucleotides in length, for example about 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. [See, for example, Gold et al, Annu. Rev. Biochem., 64: 763 (1995); Brody and Gold, J. Biotechnol., 74: 5 (2000); Sun, Curr. Opin. Mol. Ther., 2:100 (2000); Kusser, J. Biotechnol., 74: 27 (2000); Hermann and Patel, Science 287: 820 (2000); and Jayasena, Clinical Chemistry, 45: 1628. (1999)

A non-nucleotide linker may be comprised of an abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, Nucleic Acids Res., 18:6353 (1990) and Nucleic Acids Res., 15:3113 (1987); Cload and Schepartz, J. Am. Chem. Soc., 113:6324 (1991); Richardson and Schepartz, J. Am. Chem. Soc., 113: 5109 (1991); Ma et al., Nucleic Acids Res., 21:2585 (1993) and Biochemistry 32:1751 (1993); Durand et al., Nucleic Acids Res., 18:6353 (1990); McCurdy et al., Nucleosides & Nucleotides, 10:287 (1991); Jschke et al., Tetrahedron Lett., 34:301 (1993); Ono et al., Biochemistry, 30:9914 (1991); Arnold et al., International Publication No. WO 89/02439; Usman et al., International Publication No. WO 95/06731; Dudycz et al., International Publication No. WO 95/11910 and Ferentz and Verdine, J. Am. Chem. Soc., 113:4000 (1991). A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymidine, for example at the C1 position of the sugar.

The synthesis of a siNA molecule of the invention, which can be chemically-modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. Synthesis of RNA, including certain siNA molecules of the invention, follows general procedures as described, for example, in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59.

Heterocyclic Drugs

Heterocyclic drugs, and particularly those containing at least one nitrogen heterocyclic ring can be employed as pharmaceutical agents in the methods described herein. For example, yohimbine is an indole alkaloid that blocks alpha-2-adrenergic receptors. Its peripheral effects are to increase cholinergic activity at the same time that it decreases adrenergic activity. This combination has led to the use of yohimbine in the treatment and diagnostic classification of certain types of male erectile impotence.

Other examples of heterocyclic drugs includes, but is not limited to morphine, methotrexate (formerly Amethopterin, N-[4-[[(2,4-diamino-6-pteridinyl)-methyl]methylamino] benzoyl]-L-glutamic acid), Lorazepam (7-chloro-5-(o-chloro-phenyl)-1,3-dihydro-3-hydroxy-2H-1,4-benzodiazepin-2-one), 6-Mercaptopurine, (1,7-dihydro-6H-purine-6-thione monohydrate), 5-fluorouracil, nicotine, nicotinic acid and niacin.

Formulations and Delivery of Pharmaceutical Agents

The compositions of the present invention generally comprise a fusogenic saposin protein or polypeptide, which is associated with an anionic liposome comprised of either at least one anionic long-chain lipid, with or without at least one neutral long chain lipid, and at least one neutral or anionic short-chain lipids, containing a pharmaceutical or imaging agent in a safe and effective amount for the desired effect, all contained in a pharmaceutically acceptable carrier with an appropriate pH. A safe and effective amount of the active agent is defined as an amount which would cause the desired cosmetic or therapeutic effect in a patient. An experienced practitioner, skilled in this invention would have knowledge of the appropriate dosing ratios.

The appropriate dosage administered in any given case will, of course, vary depending upon known factors, such as the pharmacodynamic characteristics of the particular pharmaceutical agent, and its mode and route of administration; the age, general health, metabolism, weight of the recipient and other factors which influence response to the compound; the kind of concurrent treatment, the frequency of treatment, and the effect desired.

In one embodiment, the invention comprises a desired pharmaceutical agent, in a safe and effective amount, which is incorporated into anionic liposomes, in a buffered aqueous solution of a pH of about 5.5 or less. The preferred fusogenic protein or polypeptide is saposin C, in concentrations from about 20 nM to about 100 nM (nanomolar), preferably about 40 to about 50 nM, which is then introduced to the liposome-pharmaceutical agent mixture. The concentration of the liposomes is in excess to that of the fusogenic protein or polypeptide and is about a 1 to 10-fold excess, by molar ratio, or about a 3 to 7 fold excess to that of saposin C (i.e. at least a 1:10 by molar ratio of saposin C:liposome). In this embodiment, at least one imaging agent having at least one imaging property may be added to the liposomal composition. Alternatively, in this embodiment, the pharmaceutical agent may be substituted with the imaging agent.

In one embodiment, the liposome contains at least one type of negatively charged long-chain lipid such as dioleoylphosphatidyserine (DOPS). The liposomes may be made from any mixture of lipids that contain a suitable amount of anionic long-chain lipids. In one particular embodiment, the liposomes are made from a mixture containing anionic long-chain lipids (such as DOPS or dimyristoyl phosphatidylglcerol (DMPG)), neutral long-chain lipids (such as dipalmitoyl phosphatidylcholine (DPPC) or dimyristoyl phosphatidylcholine (DMPC)), and neutral short-chain lipids (such as DHPC). The overall charge of the resulting liposome derived from the mixture of lipids is negative. The short chain phospholipids may also be negatively charged.

Such a composition could then be applied topically to the skin or administered to other tissues or the brain and CNS via the methods described herein. Other examples of preparing such liposome-fusion protein complexes, in which an active agent is contained within the liposome, are given in U.S. Pat. No. 6,099,857, Gross, Aug. 8, 2000 and U.S. Pat. No. 5,766, 626, Gross, Jun. 16, 1998, which are herein incorporated by reference.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent to the body (see Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987)). Such dosage forms can be made by dissolving, dispersing, or otherwise incorporating the pharmaceutical agent, saposin C and anionic liposomes in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

For passive delivery systems, the rate of release is typically controlled by a membrane placed between the reservoir and the skin, by diffusion from a monolithic device, or by the skin itself serving as a rate-controlling barrier in the delivery system (see U.S. Pat. Nos. 4,816,258; 4,927,408; 4,904,475; 4,588,580, 4,788,062). The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Topical Treatments

Another aspect of this invention provides for the topical delivery of pharmaceutical compositions. This treatment regimen is suitable either for the systemic administration of the pharmaceutical agent or for localized therapy, i.e., directly to pathological or diseased tissue.

Typically, the topical formulations will comprise a preparation for delivering the pharmaceutical agent-chemical modifier complex directly to the affected skin comprising the complex, typically in concentrations in the range of from about 0.001% to 10%; preferably, from about 0.01 to about 10%; more preferably, from about 0.1 to about 5%; and most preferably, from about 1 to about 5%, together with a non-toxic, pharmaceutically acceptable topical carrier (see Dermatological Formulations: Percutaneous Absorption, Barry (ed.), Marcel Dekker Inc., (1983); for standard dosages of conventional pharmaceutical agents, see, e.g., Physicians Desk Reference (1992 Edition); and American Medical Association (1992) Drug Evaluations Subscriptions).

Topical preparations can be prepared by combining the pharmaceutical agent-chemical modifier complex with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, and the like. Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like.

Dosage forms for the topical administration of a complex of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels also may contain excipients, such as animal and vegetable fats, oils, waxes, paraffins, starch, tragacanth, cellulose derivatives, polyethylene glycols, silicones, bentonites, talc and zinc oxide, or mixtures thereof. Powders and sprays also can contain excipients such as lactose, talc, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transmucosal Delivery

Although much of the discussion herein has centered on techniques for transdermal delivery, the methods of the present invention are also applicable to the enhanced transport and delivery of pharmaceutical agents through mucosal membranes, such as gastrointestinal, sublingual, buccal, nasal, pulmonary, vaginal, corneal, and ocular membranes (see Mackay et al. (1991) Adv. Drug Del. Rev, 7:313-338). Specifically, there are many similarities between skin and mucosal membranes. For example, the membrane of the buccal cavity is non-keratinized. However, the buccal membrane is similar to the skin because both are stratified with the former consisting of polygonal cells at the basal membrane leading to squamous cells at the surface.

Transmucosal (i.e., sublingual, buccal and vaginal) drug delivery provides for an efficient entry of active substances to systemic circulation and reduce immediate metabolism by the liver and intestinal wall flora. Transmucosal drug dosage forms (e.g., tablet, suppository, ointment, gel, pessary, membrane, and powder) are typically held in contact with the mucosal membrane and disintegrate and/or dissolve rapidly to allow immediate systemic absorption.

Buccal Administration

For delivery to the buccal or sublingual membranes, typically an oral formulation, such as a lozenge, tablet, or capsule will be used. The method of manufacture of these formulations are known in the art, including but not limited to, the addition of the pharmaceutical agent-chemical modifier complex to a pre-manufactured tablet; cold compression of an inert filler, a binder, and either a pharmaceutical agent-chemical modifier complex or a substance containing the complex (as described in U.S. Pat. No. 4,806,356 incorporated by reference) and encapsulation.

Another oral formulation is one that can be applied with an adhesive, such as the cellulose derivative, hydroxypropyl cellulose, to the oral mucosa, for example as described in U.S. Pat. No. 4,940,587, incorporated by reference. This buccal adhesive formulation, when applied to the buccal mucosa, allows for controlled release of the pharmaceutical agent-chemical modifier complex into the mouth and through the buccal mucosa.

Nasal/Pulmonary Administration

For delivery to the nasal and/or pulmonary membranes, typically an aerosol formulation will be employed. The term "aerosol" includes any gas-borne suspended phase of the pharmaceutical agent-chemical modifier complex which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the pharmaceutical agent-chemical modifier complex suspended in air or other carrier gas, which may be delivered by inhalation from an inhaler device.

Delivery Across the Blood-Brain Barrier

Figure 5:
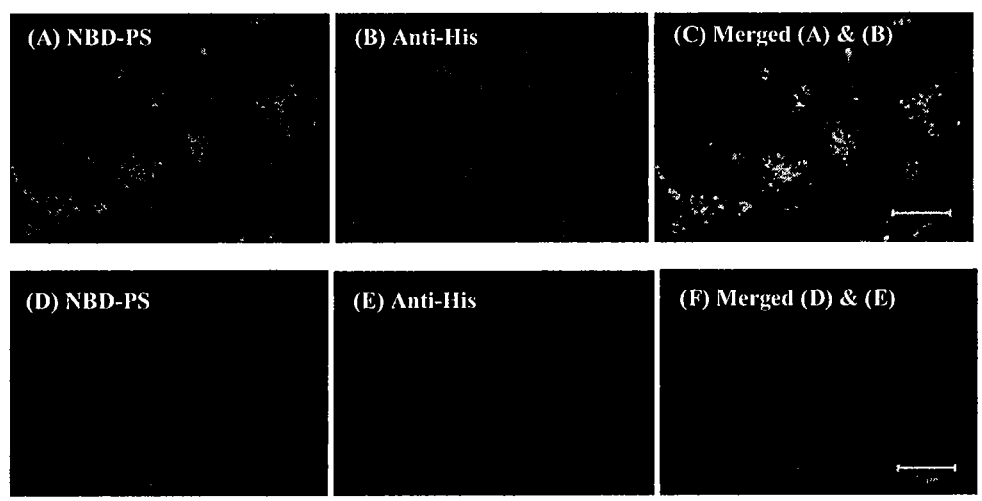
FIG. 5. Transport of NBD-DOPS and saposin C into cerebellum of mouse brains. NBD-DOPS-saposin C proteoliposomes (A,C,D) and PBS (B,E,F) were administered through tail veins of FBV/N adult mice. Frozen cerebellum sections were prepared at 48 hours after injection. NBD green fluorescence for detecting DOPS in (A) and (B) was visualized using a microscope (Zeiss Axioskop, 100×). NBD green fluorescence (C and E) and anti-His antibody (a rhodamine-conjugated secondary antibody, red fluorescence) for detecting saposin C (D and F) in Purkinje cells were imaged under a confocal microscope (LSM510, Zeiss). Bar: 20 µm (C—F). Terms: p=Purkinje cells; g=granular cells.
Figure 6:
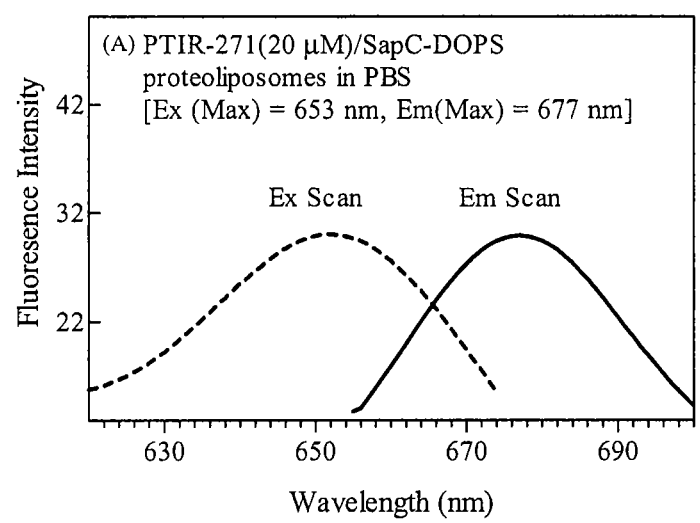
FIG. 6. Fluorescence Spectra for PTIR-271(20 µM)/Saposin C-DOPS proteoliposomes in PBS (FIG. 6A), and PTIR-316(20 µM)/SapC-DOPS proteoliposomes in PBS (FIG. 6B).
Figure 6:
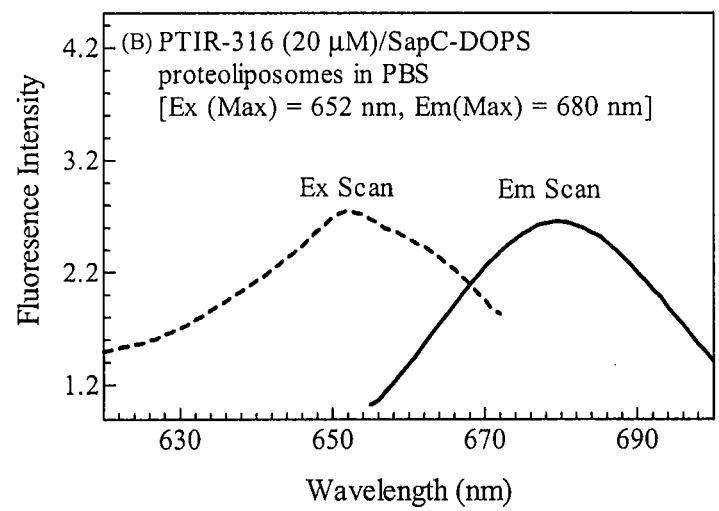

The present invention can also be used to transport pharmaceutical or imaging agents across the blood-brain barrier. Liposomes containing saposin C (or a variant or peptide thereof) and a negatively charged long-chain lipid such as DOPS can be administered intramuscularly, intravenously, intraocularly or transnasally for delivery to the CNS, specifically the brain, using methods as described in the art. Administration via the nasal cavity, for example, results in entry into the olfactory CSF then into the peripheral bloodstream similar to an intracerebroventricular infusion (ICV). As describe above in full, it should be understood by one skilled in the art that other, neutral long-chain lipids and/or short-chain lipids (neutral or negative) may be included in the composition of the liposome as described above to improve stability or utility of the final composition As an example of successful transport into the CNS, the inventor has demonstrated that saposin C can be transported into the cultured mouse cortical and hippocampal neurons, facilitated by complexes with DOPS liposomes. Saposin C can be transported into endosomal and lysosomal compartments using saposin-C liposomes containing long-chain anionic phospholipids. This method can be used for the treatment of neurological diseases including, for example, those in which MVB accumulation contributes to pathology and progression of disease. For example, in PSAP−/− mice, in which MVB formation is found in neurons and brain tissues, administration of the DOPS-saposin C liposomes via tail injection resulted in a reduction of accumulation of these structures. See FIGS. 5 and 7.

In another embodiment, a number of blood-brain targeting agents are conjugated to the surface of the liposome. Suitable targeting agents include insulin, transferrin, insulin-like growth factor, or leptin, as these peptides all have endogenous RMT systems within the BBB that also exist on the BCM, and these endogenous peptides could be used as "transportable peptides." Alternatively, the surface of the liposome could be conjugated with 2 different "transportable peptides," one peptide targeting an endogenous BBB receptor and the other targeting an endogenous BCM peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. The use of transferrin receptor (TfR)-specific peptidomimetic monoclonal antibodies as BBB "transportable peptides" are described in detail in U.S. Pat. Nos. 5,154,924; 5,182,107; 5,527,527; 5,672,683; 5,833,988; and 5,977,307. The use of an MAb to the human insulin receptor (HIR) as a BBB "transportable peptide" has been described.

The conjugation agents which are used to conjugate the blood-barrier targeting agents to the surface of the liposome can be any of the well-known polymeric conjugation agents such as sphingomyelin, polyethylene glycol (PEG) or other organic polymers. In one embodiment, PEG is the conjugation agent. In one embodiment, the molecular weight of the conjugation agent is between 1000 and 50,000 DA. In one embodiment, the conjugation agent is a bifunctional 2000 DA PEG which contains a lipid at one end and a maleimide group at the other end. The lipid end of the PEG binds to the surface of the liposome with the maleimide group bonding to the receptor-specific monoclonal antibody or other blood-brain barrier targeting vehicle. In one embodiment, from 5 to 1000 targeting vehicles is conjugated to each liposome. Liposomes having approximately 25-40 targeting vehicles conjugated thereto are provided in one embodiment.

Although the invention has been described using liposomes as the preferred nanocontainer, it will be recognized by those skilled in the art that other nanocontainers may be used. For example, the liposome can be replaced with a nanoparticle or any other molecular nanocontainer with a diameter <200 nm that can encapsulate the DNA and protect the nucleic acid from nucleases while the formulation is still in the blood or in transit from the blood to the intracellular compartment of the target cell. Also, the PEG strands can be replaced with multiple other polymeric substances such as sphingomylein, which are attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of genes to any group of cells or organs which have specific target receptors.

Treatment of Gaucher Disease with Fusogenic Saposin Proteins and Polypeptides

Additionally, saposin C is essential for hydrolysis of glucosylceramides to ceramide in vivo. A deficiency in epidermal glucocerebrosidase results in an altered glucosylceramide to ceramide ratio and this altered ratio is associated with skin barrier abnormalities characterized by Gaucher Disease. It is thought that saposin C is critical to the formation of the epidermal permeability barrier by maintaining physiologic concentrations of glucosylceramide and ceramide in the stratum corneum. According to this model, the role of saposin C in stimulating glucocerebrosidase is mediated by its destabilizing effect on the membranes. Thus, in patients with epidermal glucocerebrosidase deficiency, a topical application of a saposin C-liposome complex, wherein the liposome contains acid beta glucosidase, the mixture contained in a pharmaceutically acceptable carrier may be used to fuse cell membranes in order to facilitate the hydrolysis of glucosylceramide to ceramide to aid in regulation of skin barrier formation and function. These compositions can, for example, be formulated as creams, lotions, solutions or gels. The carrier may include, for example, pharmaceutically acceptable emollients, emulsifiers, thickening agents, solvents, preservatives, coloring agents and fragrances.

Saposin C Lysosomes as a Delivery System for Administration of Imaging Agents

In another embodiment of the present invention, the saposin C-containing liposome may be used to simultaneously deliver at least one imaging agent having one or more distinct imaging properties. These agents may use magnetic resonance imaging, fluorescence, or CT/PET detection properties. One or more imaging agents may be simultaneously integrated or encapsulated into the saposin-C-containing liposomes, such that a single population of saposin-C-containing liposomes may be used to deliver multiple imaging agents, with or without a pharmaceutical agent, to the desired tissues.

In a further embodiment of the present invention, the liposome based contrast medium of the invention may further comprise additional contrast agents such as conventional contrast agents, which may serve to increase the efficacy of the contrast medium for MRI. Many such contrast agents are well known to those skilled in the art and include paramagnetic and superparamagnetic contrast agents.

Exemplary paramagnetic contrast agents suitable for use in the subject invention include stable free radicals (such as, for example, stable nitroxides), as well as compounds comprising transition, lanthanide and actinide elements, which may, if desired, be in the form of a salt or may be covalently or noncovalently bound to complexing agents (including lipophilic derivatives thereof) or to proteinaceous macromolecules.

Preferable transition, lanthanide and actinide elements include Gd(III), Mn(II), Cu(II), Cr(III), Fe(II), Fe(III), Co(II), Er(II), Ni(II), Eu(III) and Dy(III). More preferably, the elements include Gd(III), Mn(II), Cu(II), Fe(II), Fe(III), Eu(III) and Dy(III), especially Mn(II) and Gd(III).

These elements may, if desired, be in the form of a salt, such as a manganese salt, e.g., manganese chloride, manganese carbonate, manganese acetate, and organic salts of manganese such as manganese gluconate and manganese hydroxylapatite; and such as an iron salt, e.g., iron sulfides and ferric salts such as ferric chloride. These elements may also, if desired, be bound, e.g., covalently or noncovalently, to complexing agents (including lipophilic derivatives thereof) or to proteinaceous macromolecules. Preferable complexing agents include, for example, diethylenetriamine-pentaacetic acid (DTPA), ethylene-diaminetetraacetic acid (EDTA), 1,4,7,10-tetraazacyclododecane-N,N',N'',N'''-tetraacetic acid (DOTA), 1,4,7,10-tetraazacyclododecane-N,N',N''-triacetic acid (DO3A), 3,6,9-triaza-12-oxa-3,6,9-tricarboxymethylene-10-carboxy-13-phenyl-tridecanoic acid (B-19036), hydroxybenzylethylene-diamine diacetic acid (HBED), N,N'-bis(pyridoxy)-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N'N'',N'''-tetraacetic acid (TETA), kryptands (that is, macrocyclic complexes), and desferrioxamine. More preferably, the complexing agents are EDTA, DTPA, DOTA, DO3A and kryptands, most preferably DTPA. Preferable lipophilic complexes thereof include alkylated derivatives of the complexing agents EDTA, DOTA, etc., for example, EDTA-DDP, that is, N,N'-bis-(carboxy-decylamidomethyl-N-2,3-dihydroxypropyl)-ethylenediamine-N,N'-diacetate; EDTA-ODP, that is N,N'-bis-(carboxy-octadecylamido-methyl-N-2,3-dihydroxypropyl)-ethylenedia mine-N,N'-diacetate; EDTA-LDP N,N'-Bis-(carboxy-laurylamidomethyl-N-2,3-dihydroxypropyl)-ethylenediamine-N,N'-diacetate; etc.; such as those described in U.S. Ser. No. 887,290, filed May 22, 1992, the disclosures of which are hereby incorporated herein by reference in its entirety. Preferable proteinaceous macromolecules include albumin, collagen, polyarginine, polylysine, polyhistidine, gamma-globulin and beta-globulin. More preferably, the proteinaceous macromolecules comprise albumin, polyarginine, polylysine, and polyhistidine.

Suitable complexes thus include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)-DTPA.

Nitroxides are paramagnetic contrast agents which increase both T1 and T2 relaxation rates by virtue of one unpaired electron in the nitroxide molecule. The paramagnetic effectiveness of a given compound as an MRI contrast agent is at least partly related to the number of unpaired electrons in the paragmagnetic nucleus or molecule, specifically to the square of the number of unpaired electrons. For example, gadolinium has seven unpaired electrons and a nitroxide molecule has only one unpaired electron; thus gadolinium is generally a much stronger MRI contrast agent than a nitroxide. However, effective correlation time, another important parameter for assessing the effectiveness of contrast agents, confers potential increased relaxivity to the nitroxides. When the effective correlation time is very close to the proton Larmour frequency, the relaxation rate may increase dramatically. When the tumbling rate is slowed, e.g., by attaching the paramagnetic contrast agent to a large structure, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The liposomes of the present invention are ideal for attaining the goals of slowed rotational correlation times and resultant improvement in relaxivity. Although not intending to be bound by any particular theory of operation, it is contemplated that since the nitroxides may be designed to coat the perimeters of the liposomes, e.g., by making alkyl derivatives thereof, that the resulting correlation times can be optimized. Moreover, the resulting contrast medium of the present invention may be viewed as a magnetic sphere, a geometric configuration which maximizes relaxivity.

If desired, the nitroxides may be alkylated or otherwise derivitized, such as the nitroxides 2,2,5,5-tetramethyl-1-pyrrolidinyloxy, free radical, and 2,2,6,6-tetramethyl-1-piperidinyloxy, free radical (TMPO), Exemplary superparamagnetic contrast agents suitable for use in the subject invention include metal oxides and sulfides which experience a magnetic domain, ferro- or ferrimagnetic compounds, such as pure iron, magnetic iron oxide (such as magnetite), .gamma-Fe2O3, manganese ferrite, cobalt ferrite and nickel ferrite.

The contrast agents, such as the paramagnetic and superparamagnetic contrast agents described above, may be employed as a component within the microspheres or in the contrast medium comprising the microspheres. They may be entrapped within the internal space of the microspheres, administered as a solution with the microspheres or incorporated into the stabilizing compound forming the microsphere wall.

For example, if desired, the paramagnetic or superparamagnetic agents may be delivered as alkylated or other derivatives incorporated into the stabilizing compound, especially the lipidic walls of the microspheres. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups, via a number of different linkages, e.g., an acetyloxy group. Such adducts are very amenable to incorporation into the stabilizing compounds, especially those of a lipidic nature, which form the walls of the microspheres of the present invention.

Mixtures of any one or more of the paramagnetic agents and/or superparamagnetic agents in the contrast media may similarly be used.

The paramagnetic and superparamagnetic agents described above may also be coadministered separately, if desired.

The liposomes used in the present invention may not only serve as effective carriers of the superparamagnetic agents, e.g., iron oxides, but also appear to magnify the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, e.g., 100 nm diameter, have much higher R2 relaxivities than R1 relaxivities but the smaller particles, e.g., 10 to 15 nm diameter have somewhat lower R2 relaxivities, but much more balanced R1 and R2 values. The smallest particles, e.g., monocrystalline iron oxide particles, 3 to 5 nm in diameter, have lower R2 relaxivities, but probably the most balanced R1 and R2 relaxation rates. Ferritin can also be formulated to encapsulate a core of very high relaxation rate superparamagnetic iron. It has been discovered that stabilized liposomes used in the present invention can increase the efficacy and safety of these conventional iron oxide based MRI contrast agents.

Incorporation of imaging agents into liposomes is advantageous for determining uptake and delivery of the pharmaceutical agent contained therein. Further, such agents can also permit the imaging of tissue structure, or in the case of cancers, the extent of metastasis or tumor growth. In one embodiment of the present invention, saposin-C-containing liposomes can transfer both pharmaceutical and imaging agents across biological membranes. In another embodiment, multiple imaging agents can be incorporated into the liposomal membrane, or, imaging agents having multiple imaging properties (such as the PTIR agents described above and in the Examples) can be used. Either method allows the clinician or researcher to utilize multiple methods of detection with a single administration of the liposomal composition.

Imaging agents may use magnetic resonance imaging, fluorescence or PT/CAT devices. The use of magnetic resonance imaging (MRI) contrast enhancement agents or radioactive isotopes in the body is practiced by a variety of methods. For example, Li, et al., U.S. Pat. No. 6,569,451, incorporated herein by reference, teaches a method by which polymerized liposome particles may be used to deliver contrast agents such as those using magnetic resonance imaging.

In one embodiment of the present invention, MR contrast agents (such as Ultrasmall SuperParamagnetic Iron Oxide (USPIO) nanoparticles) can be encapsulated within the aqueous interior of the liposome. MRI scanning may employ chelates of gadolinium or manganese. However, labeling of non-phagocytic cells for MR detection requires that the liposomes encapsulate and deliver sufficient quantities of the contrast agent. Tumor-specific liposomes can be used to deliver the agent to the tissue, aiding in earlier detection and better visualization using MRI. Delivery and uptake of targeted drugs can also be estimated using contrast enhanced MR microimaging, by using liposomes of the present invention as dual carriers for the drug and the contrast agent. For example, COMBIDEX (Advanced Magnetics, MA, size of 0 nm) a molecular imaging agent detected using MRI can be encapsulated in liposomes made of dioleylphosphatidyserine (DOPS). These liposomes can then be effectively delivered to human neuroblastoma cells. This is described in detail in Example 3 of the present invention.

If desired, two or more different ions may be used in combination. As those skilled in the art will recognize, once armed with the present disclosure, various combinations of the lipsoluble compounds and paramagnetic ions may be used to modify the relaxation behavior of the resulting contrast agent. The subject paramagnetic ion and liposoluble compound complexes of the invention have been found to be extremely effective contrast enhancement agents for magnetic resonance imaging.

The liposoluble compounds of the present invention may be employed singlely or in combination with one another, and in combination with one or more paramagnetic ions as contrast agents for magnetic resonance imaging. Exemplary paramagnetic ions include transition, lanthanide (rare earth) and actinide ions, as will be readily apparent to those skilled in the art, in view of the present disclosure. Preferable paramagnetic ions include those selected from the group consisting of Cr3, Co2, Mn2, Ni2, Fe3, Fe2, La3, Cu2, Gd3, Ce3, Tb3, Pr3, Dy3, Nd3, Ho3, Pm3, Er3, Sm3, Tm3, Eu3, Yb3 and Lu3. More preferably, the paramagnetic ion is selected from the group consisting of Mn2, Fe3 and Gd3, most preferably Mn2.

Multiple contrast agents are available for enhancing tissue contrast in magnetic resonance Imaging. Some of the most commonly used contrast agents are chelates of Gadolinium, such as Gd-DTPA, Gd-DTPA-BMA, and Gd-DOTA. Most currently available contrast agent formulations are of small molecular size. In one embodiment, the contrast agent is selected from the group consisting of iodine, gadolinium and magnetite.

Figure 7:
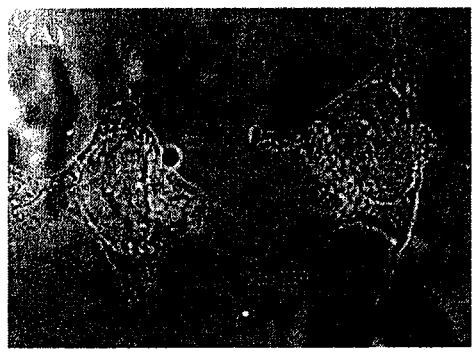
FIG. 7. Uptake of Saposin-C-DOPS containing PTIR-271 and PTIR-316 into human neuroblastoma cells (CHLA-20).
Figure 7:
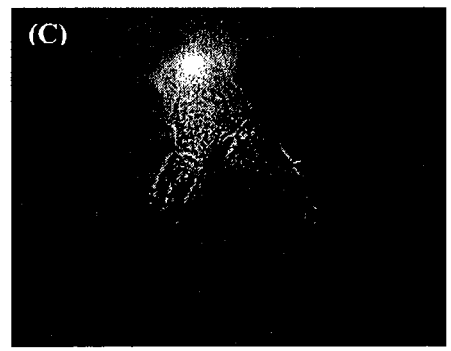
Figure 7:
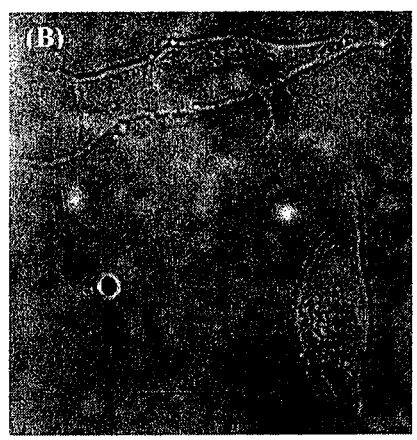
Figure 7:

Additionally, fluorescent imaging agents may be incorporated within the liposomes of the present invention, thus providing an additional means of detection. For example, NBD, Rhodamine, the PTIR labels described above, or other known fluorescent agents may be used. Any commercially available fluorescent label or fluorescently labeled dye (either lipophilic or containing a lipophilic moiety) such as those described above may be used with the present invention. Hui, L. et al. describes methods wherein the PTIR contrast agents can be used to label LDL particles, and is incorporated herein by reference. Hui, L. et al., *MR and Fluorescent Imaging of Low Density Lipoproteing Receptors*, Acad Radiol 2004; 11:1251-1259. The total concentration of the fluorescent agent in the lipid composition is about 1% to about 5% or about 2% to about 4%. Of the fluorescent agents, markers emitting longer wavelengths (red fluorescence) such as PTIR 271 and 316 yield less background in vivo. Blue and green wavelengths have greater background signal. PTIR 271 has been demonstrated by the inventors to incorporate into saposin-C-containing liposomes with minimal background and clearly detectable signal. FIG. 7 illustrates uptake of DOPS liposomes containing PTIR 271 and 316.

Liquid, iodine-containing compounds, suitably iodo- or polyiodophenyl derivatives, are used as iodine-containing contrast agents. Suitable materials include Iopromide, Ioxitalamate, Ioxaglate, Iopamidol, Iohexyl, Ilotralon, Metrizamide or Ultravist. At the same time, the contrasting agent serves as solvent for the mixture of the lyophilisates. Either gadolinium- or magnetite-containing contrasting agents are used for the magnetic resonance tomography (MRT). Suitably from 30 mg to 90 mg lyophilized particles are mixed in the required. amounts of cytostatic drug and subsequently dissolved in from 3 ml to 6 ml of contrasting agent.

The new preparation and its use enable without the help of indirect methods, using X-ray fluoroscopy, a sufficient embolization being portrayed directly, the tumor with its blood vessels being imaged as a still picture; using gadolinium- or magnetite-containing contrast drugs in combination with flow-coded measurement sequences, and the embolization can also be portrayed with the help of magnetic resonance. tomography; the attainable concentration of cytostatic drugs in the tumor tissue is considerably increased (by up to a factor of 20) in comparison to other forms of administration; and the application is simplified while, at the same time, the safety is increased (retrograde faulty perfusion is avoided).

Finally, imaging agents that use computed tomography (CT scan) or positron emission tomography (PET) can be used. The most commonly employed radionuclide imaging agents include radioactive iodine and indium. Imaging by CT scan may employ a heavy metal such as iron chelates. Additionally, positron emission tomography (PET) may be possible using positron emitters of oxygen, nitrogen, iron, carbon, or gallium. Example of radionuclides useful in imaging procedures include: $^{43}$K, $^{52}$Fe, $^{57}$Co, $^{67}$Cu, $^{67}$Ga, $^{68}$Ga, $^{77}$Br, $^{81}$Rb, $^{81}$Kr, $^{87}$Sr, $^{99}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi. These imaging agents detectable by CT/PET can be incorporated into the saposin-C liposome using methods known by those skilled in the art.

One having ordinary skill in the art may conjugate a saposin-C polypeptide to a radionuclide using well-known techniques. For example, Magerstadt, M. (1991) Antibody Conjugates And Malignant Disease, CRC Press, Boca Raton, Fla.; and Barchel, S. W. and Rhodes, B. H., (1983) Radioimaging and Radiotherapy, Elsevier, New York, N.Y., each of which is incorporated herein by reference, teach the conjugation of various therapeutic and diagnostic radionuclides to amino acids of antibodies. Such reactions may be applied to conjugate radionuclides to saposin-C peptides or to saposin-C peptides with an appropriate linker.

Labels

The compositions of this invention optionally include one or more labels; e.g., optically detectable labels, such as fluorescent or luminescent labels, and/or non-optically detectable labels, such as magnetic labels. A number of fluorescent labels are well known in the art, including but not limited to, quantum dots, hydrophobic fluorophores (e.g., coumarin, rhodamine and fluorescein), and green fluorescent protein (GFP) and variants thereof (e.g., cyan fluorescent protein and yellow fluorescent protein). See e.g., Haughland (2002) Handbook of Fluorescent Probes and Research Products, Ninth Edition or the current Web Edition, both available from Molecular Probes, Inc. Likewise, a variety of donor/acceptor and fluorophore/quencher combinations, using e.g., fluorescence resonance energy transfer (FRET)-based quenching, non-FRET based quenching, or wavelength-shifting harvester molecules, are known. Example combinations include cyan fluorescent protein and yellow fluorescent protein, terbium chelate and TRITC (tetrarhodamine isothiocyanate), lanthanide (e.g., europium or terbium) chelates and allophycocyanin (APC) or Cy5, europium cryptate and Allophycocyanin, fluorescein and tetramethylrhodamine, IAEDANS and fluorescein, EDANS and DABCYL, fluorescein and DABCYL, fluorescein and fluorescein, BODIPY FL and BODIPY FL, and fluorescein and QSY 7 dye. Nonfluorescent acceptors such as DABCYL and QSY 7 and QSY 33 dyes have the particular advantage of eliminating background fluorescence resulting from direct (i.e., nonsensitized) acceptor excitation. See, e.g., U.S. Pat. Nos. 5,668,648, 5,707,804, 5,728,528, 5,853,992, and 5,869,255 to Mathies et al. for a description of FRET dyes.

For use of quantum dots as labels for biomolecules, see, e.g., Dubertret et al. (2002) Science 298:1759; Nature Biotechnology (2003) 21:41-46; and Nature Biotechnology (2003) 21:47-51. In the context of the present invention, such quantum dots can be used to label any nucleic acid of interest, e.g., an interfering RNA.

Other optically detectable labels can also be used in the invention. For example, gold beads can be used as labels and can be detected using a white light source via resonance light scattering. Suitable non-optically detectable labels are also known in the art. For example, magnetic labels can be used in the invention (e.g., 3 nm superparamagnetic colloidal iron oxide as a label and NMR detection; see e.g., Nature Biotechnology (2002) 20:816-820).

Labels can be introduced to nucleic acids during synthesis or by postsynthetic reactions by techniques established in the art. For example, a fluorescently labeled nucleotide can be incorporated into an RNA or DNA during enzymatic or chemical synthesis of the nucleic acid, e.g., at a preselected or random nucleotide position. Alternatively, fluorescent labels can be added to RNAs or DNAs by postsynthetic reactions, at either random or preselected positions (e.g., an oligonucleotide can be chemically synthesized with a terminal amine or free thiol at a preselected position, and a fluorophore can be coupled to the oligonucleotide via reaction with the amine or thiol). Reagents for fluorescent labeling of nucleic acids are commercially available; for example, a variety of kits for fluorescently labeling nucleic acids are available from Molecular Probes, Inc., and a kit for randomly labeling double-stranded RNA is available from Ambion, Inc. (the Silencer™ siRNA labeling kit). Quenchers can be introduced by analogous techniques.

Attachment of labels to oligos during automated synthesis and by post-synthetic reactions has been described. See, e.g., Tyagi and Kramer (1996) "Molecular beacons: probes that fluoresce upon hybridization" Nature Biotechnology 14:303-308; U.S. Pat. No. 6,037,130 to Tyagi et al. (Mar. 14, 2000), entitled "Wavelength-shifting probes and primers and their use in assays and kits"; and U.S. Pat. No. 5,925,517 (Jul. 20, 1999) to Tyagi et al. entitled "Detectably labeled dual conformation oligonucleotide probes, assays and kits." Additional details on synthesis of functionalized oligos can be found in Nelson, et al. (1989) "Bifunctional Oligonucleotide Probes Synthesized Using A Novel CPG Support Are Able To Detect Single Base Pair Mutations" Nucleic Acids Research 17:7187-7194.

Labels and/or quenchers can be introduced to the oligonucleotides, for example, by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazo-phenyl-4'-maleimide (DABMI) can be used when the site of attachment is a sulfhydryl group. Similarly, fluorescein can be introduced into oligos, either using a fluorescein phosphoramidite that replaces a nucleoside with fluorescein, or by using a fluorescein dT phosphoramidite that introduces a fluorescein moiety at a thymidine ring via a spacer. To link a fluorescein moiety to a terminal location, iodoacetoamidofluorescein can be coupled to a sulfhydryl group. Tetrachlorofluorescein (TET) can be introduced during automated synthesis using a 5'-tetrachloro-fluorescein phosphoramidite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulfhydryl group; an isothiocyanate of tetramethylrhodamine coupled to an amino group; or a sulfonylchloride of Texas red coupled to a sulfhydryl group. Labeled oligonucleotides can be purified, if desired, e.g., by high pressure liquid chromatography or other methods.

Similarly, signals from the labels (e.g., absorption by and/or fluorescent emission from a fluorescent label) can be detected by essentially any method known in the art. For example, multicolor detection, detection of FRET (including, e.g., time-resolved or TR-FRET, e.g., between lanthanide chelate donors and fluorescent dye acceptors; see, e.g., Journal of Biomolecular Screening (2002) 7:3-10), and the like, are well known in the art. In brief, FRET (Fluorescence Resonance Energy Transfer) is a non-radiative energy transfer phenomenon in which two fluorophores with overlapping emission and excitation spectra, when in sufficiently close proximity, experience energy transfer by a resonance dipole induced dipole interaction. The phenomenon is commonly used to study the binding of analytes such as nucleic acids, proteins and the like. FRET is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, e.g., Haughland (2003) Handbook of Fluorescent Probes and Research Products Ninth Edition, available from Molecular Probes. A straightforward discussion of FRET can be found in the Handbook and the references cited therein.

As another example, fluorescence polarization can be used. Briefly, in the performance of such fluorescent binding assays, a typically small, fluorescently labeled molecule, e.g., a ligand, antigen, etc., having a relatively fast rotational correlation time, is used to bind to a much larger molecule, e.g., a receptor protein, antibody etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

As those skilled in the art will recognize, any of the lipid compounds and preparations containing the lipid compounds (including the lipid and contrast agent preparations), may be lyophilized for storage, and reconstituted in, for example, an aqueous medium (such as sterile water or phosphate buffered saline), with the aid of vigorous agitation. In order to prevent agglutination or fusion of the lipids as a result of lyophilization, it may be useful to include additives in the formulation to prevent such fusion or agglutination. Additives which may be useful include sorbitol, mannitol, sodium chloride, glucose, trehalose, polyvinylpyrrolidone and polyethyleneglycol (such as PEG 400). These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

The contrast agent of the invention may further, if desired, comprise a suspending agent. Preferable suspending agents include polyethylene glycol, lactose, mannitol, sorbitol, ethyl alcohol, glycerin, lecithin, polyoxyethylene sorbitan monoleate, sorbitan monoleate and albumin. As those skilled in the art would recognize, various sugars and other polymers may also be employed, such as polyethylene, polyvinylpyrrolidone, propylene glycol, and polyoxyethylene. The amount of paramagnetic acylated MR contrast agent, e.g., Mn-DDP-EDTA, may vary from about 1 to 75 percent by weight of the total ingredients used to formulate the paramagnetic MR contrast agent emulsion.

The present invention is useful in imaging a patient generally, and/or in specifically diagnosing the presence of diseased tissue in a patient. The imaging process of the present invention may be carried out by administering a contrast medium of the invention to a patient, and then scanning the patient using magnetic resonance imaging to obtain visible images of an internal region of a patient and/or of any diseased tissue in that region. By region of a patient, it is meant the whole patient, or a particular area or portion of the patient.

Any of the various types of magnetic resonance imaging devices can be employed in the practice of the invention, the particular type or model of the device not being critical to the method of the invention. The magnetic resonance imaging techniques which are employed are conventional and are described, for example, in Kean, D. M., and M. A. Smith, Magnetic Resonance Imaging: Principles and Applications (Williams and Wilkins, Baltimore 1986), the disclosures of which are hereby incorporated herein by reference in their entirety. Contemplated magnetic resonance imaging techniques include, but are not limited to, nuclear magnetic resonance (NMR), NMR spectroscopy, and electronic spin resonance (ESR). The preferred imaging modality is NMR.

As one skilled in the art would recognize, administration of the contrast agent to the patient may be carried out in various fashions, such as intravascularly, orally, rectally, etc., using a variety of dosage forms. Preferably, administration is by intravascularly. The useful dosage to be administered and the particular mode of administration will vary depending upon the age, weight and the particular animal and region thereof to be scanned, and the particular contrast agent of the invention to be employed. Typically, dosage is initiated at lower levels and increased until the desired contrast enhancement is achieved. By way of general guidance, typically between about 0.1 mg and about 1 g of the liposoluble compound of the present invention, and between about 1 and about 50 micromoles of paramagnetic ion, each per kilogram of patient body weight, is administered, although higher and lower amounts can be employed. Similarly, by way of general guidance, where lipids or suspending agents are used in the formulation, generally between about 0.5 and about 50 percent by weight of the entire formulation of each may be employed, although higher and lower amounts may also be used.

In carrying out the method of the present invention, the contrast agent may be used alone, or in combination with other diagnostic, therapeutic or other agents. Such other agents include excipients such as flavoring or coloring materials.

In one embodiment, the method is particularly useful in a human suspected of having a proliferation of a cellular mass. It can also be used with other imaging techniques and devices, as described herein. Imaging can begin pre-administration of drug using a similar composition to determine the best liposome size or after injection to follow the biodistribution of the liposomes carrying drugs. Typically, the composition is injected into a vessel of a human. Imaging comprises imaging at least 10 hours post injection of said composition or sooner. The composition can be administered using a device selected from the group consisting of an intravenous syringe injection, a catheter, an intravenous drip and an intraperitoneal syringe injection. A lipid dosage range can be established using known methods and can include a dose of 0.10 to 0.50 millimoles of lipid per kilogram of body weight.

Specific delivery of liposomes to a target tissue such as a proliferating cell mass, neoplastic tissue, inflammatory tissue, inflamed tissue, and infected tissue can be achieved by selecting a liposome size appropriate for delivering a therapeutic agent to said target tissue. For example, liposomes with a mean diameter of 180 nm may not accumulate in a solid tumor; preferably liposomes with a mean diameter of 140 nm accumulate in the periphery of the same solid tumor, and preferably liposomes with a mean diameter of 110 nm accumulate in the peripheral and central portions of that solid tumor.

In another embodiment of the invention, liposome preparations of different sizes carrying imaging agents can be used to probe capillary permeability and pore size in vivo. This information can be used to determine the optimal particle size of liposomes carrying therapeutic agents for treatment of a particular type of disease in a few experiments (e.g. 2-3). Since tumors are biologically heterogeneous and even the same tumor type may behave differently between different patients, this information can be very useful for tailoring liposome size and for the most advantageous preparation for treatment of a particular type of disease such as cancer or inflammatory tissue. In another embodiment, the specificity of delivery of liposomes to a target tissue may be further enhanced by labelling the liposomes with antibodies (e.g. therapeutic agents) or other tissue markers. In another embodiment, antibody labelling can be used to achieve or enhance intracellular delivery of the therapeutic agent.

In one embodiment, the invention provides for a method of imaging comprising
    a) administering to a mammal need thereof a composition, comprising:
        i) a sufficient amount of imaging agent,
        ii) a liposome comprising a bilayer, a fusogenic protein or polypeptide and an interior volume, wherein said liposome is in an amount sufficient to permit delivery of said liposome to a tissue, and said liposome carries the Imaging agent,
    b) imaging a tissue of the mammal.

In another embodiment, the composition used in the imaging method further comprises a therapeutic agent in an therapeutic amount, wherein said liposome carries said therapeutic agent.

The present invention also provides for methods of drug delivery, drug delivery monitoring, tumor killing, tumor regression, tumor growth monitoring and drug dosing based on delivery in a mammal. The drug delivery method can comprise:
    a) administering to a mammal need thereof a composition, comprising:
        i) a paramagnetic chelate with a paramagnetic ion, said paramagnetic chelate is in an amount sufficient to enhance NMR imaging,
        ii) a liposome comprising a bilayer, a fusogenic protein or polypeptide and an interior volume, wherein said liposome is in an amount sufficient to permit delivery of said liposome to a tissue, and said liposome carries said paramagnetic chelate,
    b) MNR imaging a tissue of said mammal.

In another embodiment, the composition used in the imaging method further comprises a therapeutic agent in an therapeutic amount, wherein said liposome carries said therapeutic agent.

Preferably, the imaging is quantitative and amount of said liposome delivered to said tissue can be estimated and the amount of selectively delivered drug calculated. These methods can be combined with methods of monitoring tissue mass to evaluate the therapeutic effectiveness of the drug delivery method and the drug. For instance, determining the volume of the tissue in order to monitor tissue volume, to indicate tissue proliferation, or to monitor a reduction in tissue mass can be accomplished. Such methods may also be used to determine the optimal delivery regime to a particular pathologic tissue in a particular patient.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonics signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may be pulsed also. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter (cm.2) to about 5.0 W/cm.2, with energy levels of from about 0.5 to about 2.5 W/cm.2 being preferred. Energy levels for therapeutic ultrasound involving hyperthermia are generally from about 5 W/cm.2 to about 50 W/cm.2. For very small vesicles, for example, vesicles having a diameter of less than about 0.5 μm, higher frequencies of sound are generally preferred. This is because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosures of which are hereby incorporated herein by reference, in their entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, K. et al., Ultrasonics Sonochemistry, Vol. 3, pp. 1-5 (1996), the disclosures of which are hereby incorporated herein by reference, in their entirety.

In connection with methods involving ultrasonic imaging, particularly in embodiments involving vesicles, diagnostic ultrasound imaging may be carried out simultaneously with the application of therapeutic ultrasonic waves so as to rupture the vesicles for purposes, such as, for example, enhanced cavitation or the targeted release of a bioactive agent combined with the vesicles. The method comprises the steps of (i) administering to the patient a quantity of vesicles; (ii) insonating the vesicles in a region of the patient with therapeutic ultrasonic waves at a frequency and energy to cause the vesicles to rupture; and (iii) simultaneously receiving ultrasonic emissions from the insonated vesicles at a harmonic of the frequency of the therapeutic ultrasonic waves and generating an image of said region from the received ultrasonic emissions. Simultaneous imaging allows an operator to monitor the rupture of the vesicles in real time.

As one skilled in the art would recognize, once armed with the teachings in the present disclosure, widely varying amounts of vesicles may be employed in the practice of the methods described herein. As used herein, the term "quantity of vesicles" is intended to encompass all such amounts.

Diagnostic imaging is a means to visualize internal body regions of a patient. Diagnostic imaging includes, for example, ultrasound (US), magnetic resonance imaging (MRI), nuclear magnetic resonance (NMR), computed tomography (CT), electron spin resonance (ESR); nuclear medicine when the contrast medium includes radioactive material; and optical imaging, particularly with a fluorescent contrast medium. Diagnostic imaging also includes promoting the rapture of the vesicles via the methods of the present invention. For example, ultrasound may be used to visualize the vesicles and verify the localization of the vesicles in certain tissue. In addition, ultrasound may be used to promote rapture of the vesicles once the vesicles reach the intended target, including tissue and/or receptor destination, thus releasing a bioactive agent and/or diagnostic agent.

In accordance with the present invention, there are provided methods of imaging a patient generally, and/or in specifically diagnosing the presence of diseased tissue in a patient. The imaging process of the present invention may be carried out by administering a contrast medium of the invention to a patient, and then scanning the patient using, for example, ultrasound, computed tomography, and/or magnetic resonance imaging, to obtain visible images of an internal region of a patient and/or of any diseased tissue in that region. By region of a patient, it is meant the whole patient or a particular area or portion of the patient.

In employing the contrast agents, they are preferably suspended in aqueous solution and the contrast medium formulated using sterile techniques. An advantage to using smaller liposomes (e.g., 200 nm and below in size) and micelles or emulsified lipids, as well as the simple suspension of paramagnetic ions and liposoluble compounds, is that the contrast agents may be filtered through 0.22 micron line filters either immediately prior to administration, such as by intravenous injection, or as a terminal step in formulation of the contrast agents, to remove any potential pyrogens.

For formulating these contrast agents into stable preparations other additives may be employed. For example, in formulating contrast agents for intravenous injection, parenteral additives may be included in the preparation. Such additives to include tonicity adjusting additives such as dextrose and sodium chloride, to formulate an isosmotic contrast medium. These tonicity additives are generally provided in minor amounts, such as about 0.1% to about 0.5% by weight of the total formulation. In addition, antimicrobial additives may be included in the final preparation so as to avoid bacterial growth. Such antimicrobial additives, in generally acceptable amounts, may include but are not limited to benzalkonium chloride (typically 0.01% by weight of the total formulation), benzyl alcohol (typically 1-2% by weight), chlorobutanol (typically 0.25-0.5% by weight), metacresol (typically 0.1-0.3% by weight), butyl p-hydroxybenzoate (typically 0.015% by weight), methyl p-hydroxybenzoate (typically 0.1-0.2% by weight), propyl p-hydroxybenzoate (typically 0.2% by weight), phenol (0.25-0.5% by weight) and thimerosal (typically 0.01% by weight). Additionally, antioxidants may be included in the preparation, and are particularly useful where the contrast agent contains unsaturated lipids. Such antioxidants in their generally useful amounts include ascorbic acid (typically 0.01-0.5% by weight), cysteine (typically 0.1-0.5% by weight), monothioglycerol (typically 0.1-1.0% by weight), sodium bisulfite (typically 0.1-1.0% by weight), sodium metabisulfite (typically 0.1-1.0% by weight), and tocopherols (typically 0.05-0.5% by weight). As those skilled in the art will recognize, the contrast agents of the invention may be formulated in a variety of means to be particularly suitable for intravascular delivery, delivery into any body cavity, or other delivery targets.

Additional Agents

It is also contemplated to be a part of the present invention to prepare microspheres using compositions of matter in addition to the biocompatible lipids and polymers described above, provided that the microspheres so prepared meet the stability and other criteria set forth herein.

Propylene glycol may be added to remove cloudiness by facilitating dispersion or dissolution of the lipid particles. The propylene glycol may also function as a thickening agent which improves microsphere formation and stabilization by increasing the surface tension on the microsphere membrane or skin. It is possible that the propylene glycol further functions as an additional layer that coats the membrane or skin of the microsphere, thus providing additional stabilization. As examples of such further basic or auxiliary stabilizing compounds, there are conventional surfactants which may be used, e.g., U.S. Pat. Nos. 4,684,479 and 5,215,680.

Additional auxiliary and basic stabilizing compounds include such agents as peanut oil, canola oil, olive oil, safflower oil, corn oil, or any other oil commonly known to be ingestible which is suitable for use as a stabilizing compound in accordance with the requirements and instructions set forth in the instant specification.

In addition, compounds used to make mixed micelle systems may be suitable for use as basic or auxiliary stabilizing compounds, and these include, but are not limited to: lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=$C_{12},C_{14},C_{16}$), benzyldimethyldodecylammonium bromide/chloride, benzyldimethyl hexadecylammonium bromide/chloride, benzyldimethyl tetradecylammonium bromide/chloride, cetyl-dimethylethylammonium bromide/chloride, or cetylpyridinium bromide/chloride.

It has been found that the liposomes used in the present invention may be controlled according to size, solubility and heat stability by choosing from among the various additional or auxiliary stabilizing agents described herein. These agents can affect these parameters of the microspheres not only by their physical interaction with the lipid coatings, but also by their ability to modify the viscosity and surface tension of the surface of the liposome. Accordingly, the liposomes used in the present invention may be favorably modified and further stabilized, for example, by the addition of one or more of a wide variety of (a) viscosity modifiers, including, but not limited to carbohydrates and their phosphorylated and sulfonated derivatives; and polyethers, preferably with molecular weight ranges between 400 and 100,000; di- and trihydroxy alkanes and their polymers, preferably with molecular weight ranges between 200 and 50,000; (b) emulsifying and/or solubilizing agents may also be used in conjunction with the lipids to achieve desired modifications and further stabilization; such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer (e.g., poloxamer 188, poloxamer 184, and poloxamer 181), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents that may be used with the lipids include, but are not limited to, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, methylcellulose, pectin, polyethylene oxide, povidone, propylene glycol alginate, silicon dioxide, sodium alginate, tragacanth, xanthum gum, alpha-d-gluconolactone, glycerol and mannitol; (d) synthetic suspending agents may also be utilized such as polyethyleneglycol (PEG), polyvinylpyrrolidone (PVP), polyvinylalcohol (PVA), polypropylene glycol, and polysorbate; and (e) tonicity raising agents may be included; such agents include but are not limited to sorbitol, propyleneglycol and glycerol.

The diluents which can be employed to create an aqueous environment include, but are not limited to water, either deionized or containing any number of dissolved salts, etc., which will not interfere with creation and maintenance of the stabilized microspheres or their use as MRI contrast agents; and normal saline and physiological saline.

Although this invention has been described in connection with its most preferred embodiment, additional embodiments are within the scope and spirit of the claimed invention. The preferred device of this invention is intended merely to illustrate the invention, and not limit the scope of the invention as it is defined in the claims that follow.

EXPERIMENTAL EXAMPLES

Example 1

Saposin C and Liposome Preparation and Delivery In Vitro and In Vivo

Materials—The following materials are from commercial sources: mouse laminin, P/S, fetal bovine serum, and DMEM (Gibco BRL, Gaithersborg, Md.); Neurobasal medium with B27 supplement (Life Technologies); restriction endonucleases (New England Biolabs, Beverly, Mass.); pET21a(+) DNA vector, E. Coli host strain [BL21(DE3)], and His·Bind resin (Novagen, Medison, Wis.); monoclonal anti-His antibody conjugated with Alexa Fluor488 (QIAGEN, Valencia, Calif.); fluorescein-conjugated goat anti-rabbit and rhodamine-conjugated sheep anti-mouse antibodies (ICN/CAPPEL, Aurora, Ohio); antifade reagent (Ventana Medical Systems, Tucson, Ariz.); $C_4$ reverse-phase HPLC column (Alltech Association Inc., Deerfield, Ill.); DOPS and 1,2-Dioleoyl-sn-Glycero-3-Phospho-L-Serine-N-(7-nitro-2-1,3-benzoxadiazol-4-yl) (NBD-DOPS) as stock solutions in chloroform (Avanti Polar Lipids, Alabaster, Ala.); polyethylenimine and papain (Sigma, St. Louis, Mo.). Anionic lipids are sodium salts. All other chemicals are reagent grade or better.

Fibroblast Cell Cultures—Human and mouse primary fibroblasts are used for all experiments and established with standard procedures in this laboratory.[15] Mouse prosaposin deficient fibroblasts from PSAP–/– mice. All the cells are cultured in DMEM/FBS (10%) media at 37° C. in monolayer for next use.

Primary Cortical Neuron Cultures—Cortical neurons are cultured in serum-free Neuroblasal medium with B27 supplements as described by Whitmarsh et al.[44] Take out E16 mouse embryos, cut the head and place them into ice-cold Ca/Mg-free Hank Balance Salt Solution (HBSS) with papain (1 mg/ml). The brain is dissected out and place scalpel along the dorsal midline between the two cerebral hemispheres but slightly deviate towards to the side as it cut. This will give a clean cerebral cortex. Peel out the meninges gently without touching the medial side of the cortex where the hippocampus is located. Cut out the cortex with curved fine surgical scissors and collect them in ice-cold HBSS. The cortical tissue is replaced in papain HBSS solution for 15-20 minutes at room temperature to soften up the tissues. Transfer them to papain-inhibitor solution for another 5 minutes at room temperature and finally back to 2 ml ice-cold HBSS. Fisherbran 12-546 (18CIR-2) coverglasses in 12-well plate are coated with PEI containing laminin overnight. The isolated cortical tissues are cultured on the PEI coated coverglass in the plate with Neurobasal/B27 medium. Kainate treatment is performed by addition of the drug to the medium.

Saposin C and Liposomes Preparation

Recombinant saposin C is routinely produced using IPTG-inducing pET system in E. coli cells in our laboratory.[11] All expressed proteins contained a His-tag, and are purified on a nickel column and with C4 reverse phase HPLC chromatography using a linear (0-100%) gradient of acetonitrile in 0.1% trifluoroacetic acid. The major protein peak is collected and lyophilized. The protein concentrations are determined as previously described by Qi et al.[11]

DOPS lipids (16.2 µg) in chloroform are dried under $N_2$ and vacuum to form a lipid film. Saposin C (79 µg) is added into the lipid film, and are suspended in 50 µl of 0.1 M citric acid/0.2 M phosphate (pH 4.7). Additional medium or PBS is added. Large unilamellar vesicles (LUV) are prepared by bath sonications.[14] Liposome size is measured by photon correlation spectroscopy with a N4+ submicron particle size analyzer (Coulter, Miami, Fla.). The sizes of the populations of LUV are evaluated using the N4+ sub-micron particle size analyzer and are dispersed with an average diameter 250±100 nm.

Delivery of Saposin C-DOPS Proteoliposomes In Vitro and In Vivo

Cells ($10^5$) are grown in DMEM medium for 48 h in a 8 wells chamber slide with coverglass (Lab-Tek II, Nalge Nunc International). Saposin C-DOPS complex in the medium is added into cell cultures. After incubated at 37° C. for 48 h, the cells are washed with PBS twice, and fixed with 2% paraformaldehyde for immunofluorescence assay. For in vivo study, the proteoliposomes in PBS are injected into mice through tail veins. Mouse brain tissues are collected at 48 h after administration of the protein-lipid complex for immunofluorescence assay.

Histopathology and Immunofluorescence

Mice brain tissues are fixed and snap frozen in 10% formalin prior to be processed. The paraffin sections are stained with hematoxylin and eosin (H&E), and analyzed under a light microscopy.

Immunofluorescence staining is done as described with minor modification.[15] Cultured cells ($1\times10^5$) in a dish with coverslips are washed with PBS and fixed with 2% paraformaldehyde for 10 min at room temperature. After treating with 0.1% Triton X-100 in PBS, the samples are incubated with each respective primary antiserum (for 2 h) and fluorescence-conjugated secondary antibody (for 1 h) at 37° C. The dilutions of primary and secondary antibodies are 1:30 and 1:60, respectively. Mouse brain tissue sections in 4% paraformaldehyde are incubated with a block solution contains 5% mouse serum prior to addition of primary anti-His antibody. Rhodamine-conjugated anti-mouse antibody is used as secondary antibody for detection. Antifade is added on the section to prevent the fluorescence quenching. Fluorescence signals are detected by a confocal microscopy (LSM510, Zeiss) or a fluorescence microscopy (Zeiss Axioskop).

Example 2

Synthesis of Liposomes Using Acidic Long-Chain Lipids, Neutral Long-Chain Lipids and Neutral Short-Chain Lipids Materials and Methods All the phospholipids DOPS, DPPC and DHPC are purchased in powder form from Avanti polar lipids and used without further purification. For dynamic light scattering (DLS) measurements, the molar ratio of DOPS to DPPC in the mixtures ranges from about 10 to about 1 with ([DPPC]+[DOPS])/DHPC=about 4 for all the samples. The lipid mixtures are dissolved in filtered ultra-pure $H_2O$ (Millipore EASYpure UV) at a total lipid concentration of 10 wt. % using a combination of vortexing and temperature cycling, between 50 and 4° C. The homogenized 10 wt. % solutions are then progressively diluted into 5, 2, 1, 0.5 and 0.1 wt. % with filtered $H_2O$.

Prior to DLS, stock lipid samples are diluted 5, 50 and 200 fold and are analyzed using an $N4^+$ particle sizer (Coulter, Miami, Fla.). It is determined that diluting the system had no effect on size determination. In the case of SANS experiments, the same sample preparation protocol is applied to the [DOPS]/[DPPC]=10 sample except that, $D_2O$ (99.9%, Chalk River Laboratories, Chalk River, ON) instead of $H_2O$ is used to obtain a sample having a total lipid concentration of 0.5 wt. %. The 0.5 wt. % solution is then further diluted into 0.1 and 0.05 wt. % mixtures using an acidic buffer composed of equal-volumes of 0.1N sodium acetate (NaAc) and 0.1N acetic acid (HAc). The resultant solution had a pH value of 4.78±0.02 in $D_2O$, and the buffer's pH is stable over 12 times dilution with $D_2O$.

In the case of SANS experiments, the same sample preparation procedure is applied to the [DOPS]/[DPPC]=10 sample except that $D_2O$ (99.9%, Chalk River Lab.) is in replacement of filtered $H_2O$ until the total lipid concentration is 0.5 wt. %. The 0.5 wt. % solution is then diluted into 0.1 and 0.05 wt. % with an acidic buffer composed of equal-volume mixture of 0.1N sodium acetate (NaAc) and 0.1N acetic acid (HAc) solution yielding a pH value of (4.78±0.02) in $D_2O$. The pH value of buffer is stable over 12 times of dilution with $D_2O$.

SapC is overexpressed in *E. coli* cells by using IPTG-inducing pET system (26). Expressed proteins with a His-tag are eluted from nickel columns. After dialysis, the proteins are further purified by HPLC chromatography as follows: The C4 reverse phase column is equilibrated with 0.1% trifluoroacetic acid (TFA) for 10 minutes, and then, the proteins are eluted in a linear (0-100%) gradient of 0.1% TFA in acetonitrile over 60 minutes. The major protein peak is collected and lyophilized. The protein concentrations are determined as previously described. Qi et al, 1994.

H1 (YCEVCEFLVKEVTKLID) (SEQ ID No. 15) and H2 (EKEILDAFDKMCSKLPK) (SEQ ID No. 16) peptides are synthesized by SynPep Corp. (California, USA) and dissolved in $D_2O$ at a concentration of 1.5 mg/mL. The 0.1 wt. % lipid solution with [DOPS]/[DPPC]=10 and ([DPPC]+[DOPS])/DHPC=4 is then individually added with the two peptide solutions (1.5 mg/mL) at a volume ratio of about 12:1 and the SapC solution with a volume ratio of about 12:1 to yield the final peptide (or SapC) concentration of 62.5 .mu.M, which is greater than the SapC concentration needed to induce membrane destabilization. (Wang, et al., 2003).

The SANS experiment is conducted at one of the 30 m SANS instruments, NG7, located at National Institute of Standards and Technology (NIST) Center for Neutron Research (NCNR, Gaithersburg, Md., USA). A wavelength, λ, of 8.09 Å and neutron focusing lens in combination of a long sample-to-detector distance (SDD) of 15.3 m are used to procure smaller values of scattering vector, $q=4\pi/\lambda \cdot \sin(\theta/2)$, where θ is the scattering angle. The other two SDD of 5 and 1 m are also employed to cover a whole q range from 0.002 to 0.35 Å$^{-1}$. The raw 2-D data are then corrected by the detector sensitivity, background, empty cell scattering and transmission of the sample, and are then circularly averaged around the beam center to yield 1-D data. The 1-D data are put on the absolute scale according to the flux of the direct beam. The incoherent plateau is determined averaging the intensity of the last 10~20 data points and subtracted from the reduced data.

Liposome size is measured by photon correlation spectroscopy with a N4+ sub-micron particle size analyzer (Coulter, Miami, Fla.) as described (14, 15). The sizes of the populations of LUV are evaluated using the N4+ sub-micron particle size analyzer and are polydispersed with an average diameter between 20-800 nm. The data for liposome size estimation is acquired at a 90° angle and processed using size distribution process (SDP) analysis with a fair autocorrelation function. The size is presented with a major fraction of vesicles by SDP determination. Statistical significance is estimated with ANOVA analysis. Error bars denote standard deviation.

Transmission electron microscopy (TEM) images are taken with a Hitachi TEM (H-7600, HITACHI, Japan). A droplet of each sample is placed on a nickel grid coated with a support formvar film (200 mesh, a thickness range from 30 to 75 nm, Electron Microscopy Sciences, PA). The grid is placed on the filter paper at room temperature for 2 h prior to TEM analysis. The TEM is operated at an acceleration voltage of 80 kV. The imaging background is optimized at high magnification while the area of interest is located at low magnification (50-1,000×). A single vesicle is focused on using up to 50,000× magnification. Contrast and brightness are manually adjusted until a "sharp" image is obtained and imaging background is optimized at high magnification. TEM micrographs are taken using a dual AMT CCD digital camera (2K×2K, 16 bit) with appropriate image acquisition software.

With respect to the embodiment using short-chain lipids, the generally accepted model for the kinetics of forming low-polydispersity ULV is described as follows:

Initially, the discoidal micelle precursor starts to form with the short-chain lipid coating at the rim and long-chain lipids at the planar bilayered surface of the disks to minimize the curvature energy at the rim. Either dilution or temperature elevation causes the loss of the short-chain lipid at the rim to the bilayer or solution, resulting in an increase of line tension and consequently coalescence between disks to form larger disks. As the increase of line tension overwhelms the coalescence of the nearby discoidal micelles, the contour length of the rim has to decrease, causing the bilayer to fold into a spherical shell with an opening, whose rim is covered by the short-chain lipid. Eventually, the opening can close up with the disappearance of the short-lipid around the rim, resulting in the morphology of vesicles.

Example 3

MR Detection of Tumor Cells Labeled with USPIO Using DOPS Liposomes

To prepare the liposomes containing MR detectable labels such as USPIO, the following method is used. Sonication of dextran coated USPIO particles in aqueous solution with DOPS does not yield sufficient encapsulation in the liposomes. In order to increase USPIO content in liposomes, a chemical coupling method as described by Bogdanov et al, Trapping of dextran-coated colloids in liposomes by transient binding to aminophospholipid: preparation of ferrosomes. Biochim Biophys Acta, 1994. 1193(1): p. 212-8 is used with minor modifications. Briefly, the dextran coating on the USPIO particles is oxidized to generate aldehyde groups. Aldehydes form a covalent Schiff bond at high pH with amines of DOPS. Liposomes obtained have a mean size of 150 nm as confirmed by N4+ Particle Sizer (Beckman Coulter, CA) analysis. The liposome solution is dialyzed against a low pH solution to detach USPIO bound to the external layer of the liposomes. Unencapsulated USPIO are removed by affinity chromatography using a Con-A Sepharose 4B column (Amersham Biosciences Corp., NJ).

The USPIO-DOPS liposome structure is confirmed by conventional electron microscopy. A standard R2 relaxivity curve generated using known quatities of free USPIO and DOPS liposome mixtures is used to estimate the iron concentration in the DOPS liposomes. A maximum content of 32 µg Fe/ml is achieved using 1 mM DOPS concentration. Four samples of neuroblastoma cells are prepared with approximately 10,000 cells per group. The first and second samples are incubated with 100 uM and 300 µM USPIO-DOPS liposome preparation in growth medium respectively. The third sample contained cells with no USPIO or liposomes. After incubation for 36 hours, the cells are washed 4 times, trypsinized and fixed in a mixture of 0.5% agarose solution and growth medium (1:1) in 4 ml glass vials.

High resolution MR imaging of the cells is performed using a 7T Bruker Biospec scanner using gradient echo methods optimized for T2 weighting. A 3D FLASH imaging sequence with TR/TE/θ of 200 ms/35 ms/10' and a 320×320×64 matrix is used for a 3.2 cm×3.2 cm×0.64 cm FOV resulting in an isotropic 100 um resolution.

The MR images indicates uptake of USPIO particles by cells in samples 1 and 2, with sample 2 showing an increased uptake corresponding to the higher concentration of USPIO-DOPS liposomes. A much lower number of cells is detected in sample containing cells with liposome-USPIO solution prepared by sonication. An estimate of the number of cells detected in each vial is obtained using a post-processing algorithm written in IDL. The number of cells detected in vial 2 is approximately 1.4 times compared to vial 1. The average contrast-to-noise ratio (CNR) between the gel and hypo-intensity regions representing cells is 20.15, SD 11.

Example 4

Preparation of SapC-DOPS Proteoliposomes

Protonation of SapC is used to promote the bind of SapC and DOPS membranes. First, SapC is protonated by dissolving in an aliquot acidic buffer (pH 5, 20 µl), then diluted with PBS or neutral buffer (pH 7) into 1 ml final volume. Alternatively, Brønsted acid (such as TFE, chloroform, methonal, etc.) can be used to dissolve SapC with DOPS lipids. These Bronsted acids have been reported to be a good H-bond donor and to have a protonation effect on the proteins (1). These solvents can be evaporated to dry under $N_2$ gas or a vacuum system. Suitable plecable (such as PBS) is added to form SapC-DOPS proteoliposomes. This procedure is to avoid the DOPS liposome fusion induced by SapC at acidic pH. The proteoliposomes prepared by this approach are in a monodisperse form with an average size at 200 nm.

Example 5

Temperature Control Leakage of SapC-DOPS Proteoliposomes

SapC-DOPS proteoliposomes are designed with various lipid compositions to be sensitive to the temperature for leakage of the contents encapsulated into the liposomes.

Example 6

Characterization of Liposomes/Saposin C

To elucidate the temporal and spatial interaction of saposins with liposomal membranes, the Inventor has focused efforts on the development of intrinsic (Trp) and/or extrinsic (NBD, pyrene, etc.) fluorescence determination methods. These approaches include maximal emission spectrum shift, fluorescence resonance energy transfer, fluorescence stopped-flow analysis, flow-analysis of fluorescent bead-saposin-liposome complexes, and fluorescence microscopy. In addition, circular dichroism (CD) is used to evaluate relative secondary structure changes from lipid-free to lipid-bound saposins. Analyses of the initial results evolved into the proposed hypothesis.

Summarized below are the studies related to the expression, purification, functional analysis, mutagenesis, as well as fluorescence analyses of saposin-phospholipid interaction and membrane fusion.

I. Purification and Characterization of Natural and Recombinant Saposins a) Expression of Saposins from Prokaryotic Systems Although natural saposins have been isolated and characterized, it is important to establish a recombinant expression system to provide an accessible source of large amounts of normal, mutated and Trp-labeled saposins for the proposed investigations. A prokaryotic system is developed, based on the following: 1) Saposins have at least one occupied N-glycosylation site, but, for saposins B and C, occupancy of these sites are not needed for function. 2) Expression of proteins in eukaryotic systems is labor and resource intensive, and slow. In comparison, prokaryotic systems are rapid and give high yields of wild-type and mutant proteins. And 3) The proteins can be labeled with Trp residues as intrinsic fluorescence probes, since wild-type A is the only saposin that contains a natural Trp (37W).

b) Production of Active Saposins in *E. Coli*

Functional saposins were overexpressed in BL21(DE3) cells using a pET 21a series vector. Following IPTG induction at 37° C. or 30° C., large amounts of saposins containing His-Tag were found in the soluble fraction of the disrupted cells. These were conveniently purified to electrophoretic homogeneity on nickel-loaded columns. Alternatively, saposins without His-Tag were generated by introducing a stop codon after protein coding region, and then purified using immuno-affinity columns with T7-taq monoclonal antibody. The purified recombinant saposin C shows excellent activation of acid β-glucosidase and other biologic properties. Circular dichroism spectra, light scattering, and ES-MS analyses were used to evaluate the physical properties of the purified saposins, such as aggregation status and molecular weight. Trp-saposins without His-Tag were also generated for necessary control experiments. The functional integrity of recombinant saposin C is determined using delipidated and homogenous acid β-glucosidase in a liposomal reconstitution system and in neuritogenic assays. Recombinant saposin B function is determined using a sulfatide binding assay. The in vitro function of recombinant saposins B and C are similar to the natural or deglycosylated saposins.

II. Functional Conformations of Saposins Induced by Phospholipids

To determine the specificity of saposin C-phospholipid interaction, a liposomal system is developed using CD, fluorescence emission shifts, and fluorescence quenching methods. Mutated saposins C's, produced to contain individual Trp (W), are termed saposin C(0W), (S37W), and (81W). These Trp-labeled saposin C's are as follows: saposin C(0W) has a Trp preceding the first $NH_2$-terminal amino acid of mature saposin C, saposin C(S37W) has a Trp at residue 37 (i.e., in the middle), and saposin C(81W) has a Trp after the last COOH-terminal amino acid. These substitutions had no effect on the activation properties or CD spectra of saposin C.

a) CD Spectra

Using CD spectroscopy, relative secondary structural changes of recombinant saposins are induced by membrane binding. The relative secondary structural changes of saposins obtained from the acidic, unsaturated phosphatidylserine (PS)/saposin C complexes and the neutral phosphatidylcholine (PC)/saposin B complexes are similar and result in a decrease the β-strand and an increase the α-helix content (Table 4).

TABLE 4

Circular Dichroism (195-250 nm) Analyses of Saposins with Various Phospholipids

| II. Saposin | % α | % β | % T | % R |
|---|---|---|---|---|
| C Only | 29.9 | 41.7 | 0.0 | 28.4 |
| C + Phosphatidylserine (18:0, 0) | 30.1 | 40.4 | 1.4 | 28.1 |
| C + Phosphatidylcholine (18:1, 1) | 30.6 | 41.0 | 0.0 | 28.4 |
| C + Phosphatidylserine (18:1, 1) | 49.8 | 3.9 | 14.0 | 32.4 |
| B only | 43.7 | 36.6 | 0.0 | 19.7 |
| B + Phosphatidylserine (18:1, 1) | 43.8 | 38.8 | 0.0 | 17.9 |
| B + Phosphatidylcholine (18:1, 1) | 68.2 | 24.2 | 5.3 | 2.3 |
| A only | 44.0 | 31.9 | 0.0 | 24.1 |
| A + Phosphatidylserine (18:1, 1) | 39.3 | 34.9 | 0.5 | 25.4 |

No changes are observed with saposin A and B in the PS (18:1,1) complexes. These results indicate that saposin A and B have a different membrane interaction from that of saposins C. The CD data are collected on a Jasco 710 instrument, and deconvoluted using Yang's method (see Chang, C. T., Wu, C. S., and Yang, J. T. Anal. Biochem (1978) 91, 13-31).

b) Fluorescence Emission Spectra

Emission spectra of proteins shift when the tryptophanyl environments change polarity. The fluorescence spectra of saposins A(0W), A(37W), A(81W), C(0W), and C(81W) obtained upon addition of brain phosphatidylserine (BPS) liposomes, showed blue-shifts (Table 5).

TABLE 5

Fluorescence Emission Maxima of Trp-saposins in the Absence and Presence of Brain phosphatidylserine (BPS)

| Saposins | Emission Maxima (EM, nm) | | |
|---|---|---|---|
| | −BPS | +BPS | EM Shifts |
| C(0W) | 339 | 333 | Blue |
| C(S37W) | 351 | 351 | No |
| C(S37W, Q48N) | 345 | 339 | Blue |
| C(S37W, Q48A/E49A) | 338 | 329 | Blue |
| C(81W) | 339 | 323 | Blue |
| A(0W) | 345 | 333 | Blue |
| A(37W) | 351 | 338 | Blue |
| A(37W, G64E) | 344 | 358 | Red |
| A(37W, K63L/G64E/M65V) | 339 | 350 | Red |
| A(81W) | 345 | 336 | Blue |

Experiments conditions: pH 4.7, protein:lipid=1:20 to 40. No differences are observed at 22 or 37° C.

The blue-shifts suggest interaction of saposins with lipids during complex formation. However, saposin C(S37W) shows no shift in the presence of BPS. This implies that the $NH_2$—(0W) and COOH-(81W) termini of saposin C enter the membrane whereas the middle of the sequence does not. With saposin A, the reverse is true with the middle of the sequence (37W) in the membrane. This means that saposin A-membrane associations are quite different from those of the saposin C. These results are consistent with the CD analysis. Maximal emission wavelength changes are not observed with saposin As or Cs in the presence of neutral EPC nor with PS containing saturated fatty acid chains.

1. Temporal and Spatial Interaction of Saposins and Phospholipid Membranes

To investigate temporal and spatial interactions of saposins and liposomal membrane, fluorescence stopped-flow and quenching approaches are used with Trp as the intrinsic fluorescence probe of the saposins. These experiments allow identification of regional interactions between saposins and lipid bilayers, and also the kinetics of their binding.

Temporal Interactions

Fluorescence intensity increased significantly upon saposin C(0W) binding to synthetic phosphatidylserine [PS (18:1,1)] vesicles at acidic pH. This binding induces change is lipid-concentration dependent and requires at least one unsaturated fatty acid chain. To evaluate the kinetics of this interaction, stopped-flow experiments are conducted the change in fluorescence during saposin C/liposome complex formation is monitored. When saposin C(0W) is mixed with PS(18:1,1) or BPS vesicles, fluorescence of Trp is increased, but the time course of this change is undetectable due to limitation of the machine's capability. Apparently, the interaction of saposin C and unsaturated PS containing membranes occurs within at least 10 ms.

From CD and emission spectra data, saposin C binds negatively charged, unsaturated phospholipids. This suggests there is an electrostatic interaction between positively charged residues in saposin C and the negatively charged membrane surface. This initial interaction is followed by the protein embedding into membrane through a hydrophobic interaction. No shift in emission or change in intensity of Trp fluorescence is observed with the saposin C(0W) and PS(18: 0,0) mixture.

Spatial Interactions

To determine the depth of saposin insertion into BPS liposomes, spin-labeled phosphatidylcholines (SLPCs) are incorporated into BPS liposomes with increasing mole percentages (0-50%). SLPCs, hydrophobic fluorescence quenchers, contain doxyl groups which are located at different carbons (n) in the acyl chain: SLPC5 (n=5), SLPC 10 (n=10), and SLPC16 (n=16). After addition of Trp-saposins, the protein-liposome mixture (protein:lipid=1:20) is incubated at room temperature for 30 minutes, and then, the fluorescence intensity changes are recorded. For the Trp-saposins that show the blue-shifts in Table 2, significant quenching effects (30-60%) are observed with BPS/SLPC5 liposomes. The quenching efficiency is dependent upon the location in the acyl chain of the doxyl groups on SLPC. The deeper the doxyl group is in the membrane, the lower quenching efficiency. With BPS/SLPC10, the tryptophanyl fluorescence of saposin C (0W) is quenched by 30%.

2. Saposin C-Induced Membrane Fusion

Saposin C is a multifunctional molecule having lysosomal enzyme activation and neuritogenic activities. Detailed function/structure organization of saposin C is shown in FIG. 3.

The amino acid residues 51-67 are necessary, but not sufficient, for its optimal enzymatic activation function. The disulfide structure and conformational alteration of saposin C upon lipid binding are also required for this activity. Three approaches are used for this study: (1) stopped-flow monitoring reduction of self-quenching resulting from fusion of fluorescence probe-containing vesicle with non-fluorescent vesicle induced by saposin C; (2) monitoring the lipid vesicle size changes upon addition of saposin C to vesicles, the size distribution as determined using N4 plus submicron particle sizer (Coulter Co.); (3) monitoring intrinsic fluorescence of Trp-saposin C change during liposomal fusion. These results define the fusogenic activity regions at the 1-helical domain at amino- and carboxyl-terminus in saposin C, and kinetics of saposin C induced liposomal fusion (see below).

Saposin C Induced Liposomal Fusion

Fluorescence probes have been widely used to determine membrane fusion, such as fluorescence dequenching, and fluorescence resonance energy transfer (FET), and can be used for quantitative and kinetics analyses. The dequenching approach is used to investigate saposin C's fusogenic activity. Octadecyl rhodamine B (R18) is selected as fluorescence probe and is entrapped in internal aqueous compartment of liposomal vesicles by co-sonication with BPS or PS(18:1,1). R18 shows self-quenching at high concentrations.

Fluorescence increase (dequenching) of R18 occurs upon R18 concentration decreases. After non-labeled and labeled vesicles fuse, the R18 concentration is diluted, resulting in an increase in intensity of fluorescence. R18-labeled vesicles (lipid:R18=96:4, mol:mol) are mixed with the same lipid vesicles without fluorescence probe. Stopped-flow assays are conducted to quickly mix these vesicles with saposin C or $Ca^{2+}$ ion. Time-trace curves are generated for kinetic analysis. Induction of unsaturated PS(18:1,1) membrane fusion by saposin C shows the same kinetics as those with $Ca^{2+}$. Fusion occurs extensively when reaction temperature is above the phase Transition temperature ($T_c$) of phospholipids. The $T_c$ of synthetic PS(18:1) is about −11° C., while the $T_c$ of PS(18:0) is very high (68° C.). Thus, the lipid bilayer phase of PS(18:1,1) is different to that of BPS(18:0 and 18:1) at 24° C. The results indicate that kinetics of saposin C-induced membrane fusion is determined by the physical state of the bilayer lipids.

3. Size Change Determination

Figure 4:
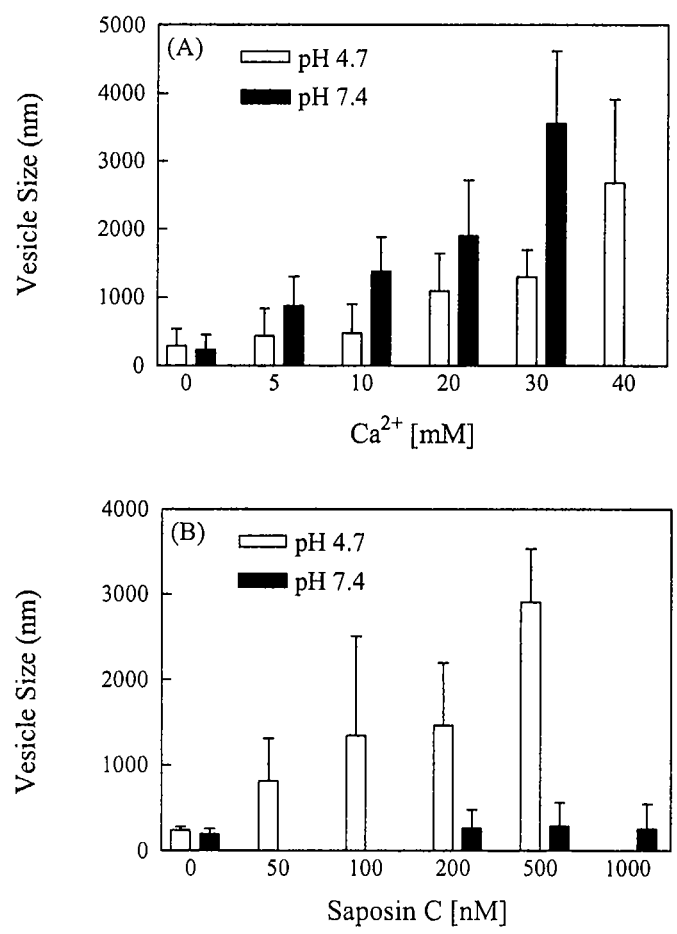
FIG. 4: Size changes of BPS (brain phosphatidylserine) liposomes induced by $Ca^{2+}$ (a) or Saposin C (b) at pH 4.7 or 7.4. Fair autocorrelation function, dust=0.0%, base line error <1%, room temperature.

Electron microscopy (EM) is used for vesicle fusion analysis, since the size of fused vesicles is bigger than those of non-fused. N4 plus submicron particle size is used to estimate particle sizes in the range of 3 nm to 3 μm since most liposomes fit in this range. Sonication conditions with a cup sonicator give mono-dispersed BPS-liposomes with ~200 nm in size. Upon addition of saposin C, these vesicles change to a larger size up to 2-3 μm. The size increase is related to vesicles fusion as shown by the above dequenching experiments. Saposin C enlarges vesicle size at pH 4.7, but not at pH 7.4 over a 10 min period (see FIG. 4).

These data suggest a pH-sensitive fusogenic activity of saposin C. Saposin C promotes the size changes at ~50 nM concentration. To define the regions responsible for this fusion property, peptides containing only 50% of the $NH_2$-terminal or 50% of the COOH-terminal halves in saposin C are tested. Both peptides show fusion activity. These data suggest linear sequence(s) mediated fusion located on both saposin C ends.

4. Mechanism of Fusion

Protein conformational changes are thought to play a role in protein-mediated membrane fusion. This fusion mechanism is evaluated using saposin C-dependent membrane fusion. First, saposin C—PS(18:1,1) liposome complexes are formed. In this saposin C-anchored membrane, protein conformation is altered. This complex is stable from pH 3 to 10, and in low concentrations of SDS solution. This indicated that dissociated rate of saposin C from PS vesicles is very slow.

Since the Trp in saposin C(0W) is embedded inside of lipid bilayer, the change of its signal is indicative of that the surrounding environment of Trp has been changed. After about 20 to 30 ms, Trp fluorescence signal decreases to the starting level. This indicates that saposin C in the complexes interacted with additional PS-vesicles. Shortly after this, the signal drops back to starting level signaling on end of the fusion process. These data indicate that saposin C retains the fusogenic activity even when it bound to lipid membrane. Therefore, a conformational change of saposin C upon lipid binding is not required for its fusogenic activity. This result is consistent with the conclusion that a linear sequence(s) is sufficient to induce membrane fusion XI. Saposin C Gene Optimization and Synthesis The Saposin C DNA sequence is codon-optimized for expression in *E. coli*, with consideration of mRNA secondary structure and elimination of restriction sites later to be used for subcloning. The restriction sites NdeI and SalI are added at the 5' and 3' ends, respectively, of the gene, and double stop codons are added at the end of the Saposin C coding sequence to ensure proper termination of the expressed protein. Gene synthesis is contracted to DNA2.0, and the optimized gene is confirmed by sequencing and supplied to VTI in the cloning vector "pJ2". This vector construct is referred to as pJ2-SapCg; the optimized Saposin C gene cassette, bordered by the restriction sites NdeI and SalI, is referred to as SapCg.

Cloning into pET24a

Cloning of SapCg into pET24a is carried out in the following manner. SapCg is cut out of pJ2-SapCg using restriction sites NdeI and SalI and ligated into the expression vector pET24a (Novagen), which has also been cut at those same sites. This ligated construct is transformed into *E. coli* cloning strain TOP10 (Invitrogen). Selection is carried out with kanamycin (50 mg/L). Colony PCR is carried out to determine which transformed colonies carried vector with SapCg insert. One colony is chosen for further work from those that tested positive. Plasmid DNA is prepared by plasmid miniprep kit (Qiagen) from this clone, and the presence of SapCg insert DNA is confirmed by restriction and sequence analysis. This plasmid construct is called pET24a-SapCg.

Shake Flask Induction

The expression construct, pET24a-SapCg, is transformed into competent *E. coli* expression strain BL21(DE3) (Novagen). Three colonies (clones) are chosen and tested for initial test expression of Saposin C. This small scale expression is carried out in 125 ml shake-flasks using LB media with kanamycin (50 mg/L) for BL21 (DE3) clones. Induction is achieved by addition of IPTG to a final concentration of 1 mM when cell OD600 reached approximately 0.6. Samples are taken immediately prior to and at four hours after induction. Expression of protein of the correct size is similar for all three BL21 (DE3) clones. Working glycerol seed stocks are prepared for all three clones. One clone is randomly selected for further development.

Fermentation Conditions

The clone used for fermentation is pET24a-SapCg (described above) transformed in the *E. coli* expression strain BL21(DE3). Fermentation is conducted using an 8-liter NBSC BioFlow 3000 fermentor, and consisted of fed-batch fermentation with DO-Stat feeding strategy. Initial culture volume is 5 liters. Batch media and feeding media composition is shown in Tables 1 and 2. The fermentation temperature prior to induction is 30° C. Induction is accomplished by addition of IPTG to a final concentration of 1 mM at late log phase, accompanied by a temperature shift to 37° C. The entire fermentation lasted 22 hours, with induction for 10 hours.

TABLE 1

Batch media

| | Component | Amt/L | Unit |
|---|---|---|---|
| 1 | $(NH_4)_2HPO_4$ | 4 | g |
| 2 | $KH_2PO_4$ | 13.3 | g |

TABLE 1-continued

Batch media

| Component | Amt/L | Unit |
|---|---|---|
| 3  MgSO$_4$•7H$_2$O | 1.2 | g |
| 4  Citric acid | 1.7 | g |
| 5  Yeast extract | 2 | g |
| 6  Trace metal solution | 10 | ml |
| 7  Glucose•H$_2$O | 22 | g |
| 8  Adjust volume to 5 L with Type I water, pH 6.8 | QS | ml |

TABLE 2

Feeding media

| Component | Amt/L | Unit |
|---|---|---|
| 1  D-glucose-monohydrate | 660 | g |
| 2  Yeast extract | 60 | g |
| 3  MgSO$_4$•7H$_2$O | 20 | g |
| 4  Type I water | QS | ml |

Inclusion Prep

An inclusion body prep is carried out using paste from the above fermentation. Approximately 20 g paste is resuspended in a total of 200 ml lysis buffer (50 mM Tris pH8, 1 mM EDTA, 100 mM NaCl). After resuspension and complete homogenization, microfluidization is used to break open cells. The insoluble portion of the cell lysate is pelleted by centrifugation for 60 min at 16,000×g at 4° C. Pellets are homogenized in a total of 800 ml lysis buffer plus 1% triton X-100 and mixed 45 minutes at room temperature. Centrifugation is carried out for 60 min at 16,000×g and 4° C. Two more washes are carried out using lysis buffer with 1% triton X-100 and one time using lysis buffer without triton X-100. Pellets are then resuspended in a total of 600 ml 6M urea pH8.5 (buffered with 20 mM Tris) and stirred at room temperature for 3 hrs. Centrifugation is carried out for 60 min at 16,000×g and 4° C. to clarify sample. The resulting supernatant is used for further purification after confirmation of the presence of Saposin C using a Saposin C specific antibody.

SapC Chromatography and Refolding

The following chromatography, refolding, and concentration steps are all performed under endotoxin-free conditions. Purification of Saposin C from inclusion bodies is carried out by ion exchange chromatography using Q-sepharose Fast Flow resin (GE Amersham). Equilibration buffer (Buffer A) is 6 M urea/0.02M Tris, pH8.5. Elution buffer (Buffer B) is 6 M urea/1 M NaCl/0.02 M Tris, pH8.5. Elution is initially carried out by step gradient, with 5% BufferB/95% BufferA for 10 column volumes, then 10% BufferB/90% BufferA for 10 column volumes, followed by a linear gradient from 10% to 100% BufferB over 10 column volumes. All fractions are collected and retained. Analysis of fractions for presence of Saposin C is carried out by SDS-PAGE, and the fraction containing the majority of Saposin C is chosen for refolding.

Refolding is carried out by dialysis into McIlvaine buffer (0.05 M citric acid/0.1 M phosphate, pH 4.7). Saposin C protein is then concentrated to approximately 0.2 mg/ml. This preparation is determined to be approximately 90% pure by visual examination of SDS-PAGE.

What is claimed is:

1. A method of delivering an anti-cancer agent or an imaging agent to a lesion of the nervous system, said method comprising the step of systemically administering to a patient a composition comprising:

a) one or more phospholipids selected from the group consisting of anionic long-chain lipids, neutral long chain lipids, neutral short chain lipids, anionic short-chain lipids, and mixtures thereof;

b) a safe and effective amount of the agent; and c) a saposin c polypeptide;

wherein the composition forms nanoparticles having a mean diameter between 200 and 350 nanometers,
wherein the overall charge of the nanoparticle is negative, and
wherein the lesion is a brain cancer.

2. The method of claim 1 wherein the phospholipids comprise a mixture of anionic long-chain lipids and neutral long-chain lipids.

3. The method of claim 1 wherein the phospholipids comprise a mixture of anionic long-chain lipids, neutral long-chain lipids and neutral short-chain lipids.

4. The method of claim 3 wherein the nanoparticle contains cationic phospholipids.

5. The method of claim 3 wherein the amount of the anionic long-chain lipids, the neutral long-chain lipids and the neutral short-chain lipids is governed by a formula of ([neutral long chain lipids]+[anionic long chain lipids])/(neutral short chain lipids), and wherein the result of the formula equals about 4.

6. The method of claim 1 wherein the nanoparticle comprises dioleoylphosphatidylserine, dipalmitoyl phosphatidylcholine and hexanoyl phosphatidylcholine, wherein the amount of the anionic long-chain lipids, the neutral long-chain lipids and the neutral short-chain lipids is governed by a formula of ([neutral long chain lipids]+[anionic long chain lipids])/(neutral short chain lipids), and wherein the result of the formula equals about 4.

7. The method of claim 1, wherein the pH of the composition is between about 5.5 and about 2.

8. The method of claim 1 wherein the concentration of the phospholipids is in at least about 1 to about 10-fold excess, by molar ratio, to that of the polypeptide.

9. The method of claim 6 wherein the molar ratio of dioleoylphosphatidylserine to dipalmitoyl phosphatidylcholine is from about 10 to about 1.

10. The method of claim 1, wherein the composition further comprises a pharmaceutically acceptable carrier.

11. The method of claim 1, wherein the brain cancer is neuroblastoma.

12. The method of claim 1, wherein the agent is an imaging agent.

13. The method of claim 12 wherein the imaging agent is selected from the group consisting of magnetic resonance detectable label, fluorescence, and CT/PET detectable label.

14. The method of claim 12 wherein the imaging agent has two or more imaging properties.

15. The method of claim 14 wherein the imaging agent is a PTIR dye containing both a fluorophore and a Gd(Ill) moiety that can be detected via magnetic resonance imaging (MRI) or confocal fluorescence microscopy.

* * * * *

```
                        SEQUENCE LISTING

<160> NUMBER OF SEQ ID NOS: 18

<210> SEQ ID NO 1
<211> LENGTH: 40
<212> TYPE: PRT
<213> ORGANISM: Homo sapiens

<400> SEQUENCE: 1

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro
        35                  40

<210> SEQ ID NO 2
<211> LENGTH: 22
<212> TYPE: PRT
<213> ORGANISM: Homo sapiens

<400> SEQUENCE: 2

Val Tyr Cys Glu Val Cys Glu Phe Leu Val Lys Glu Val Thr Lys Leu
1               5                   10                  15

Met Cys Ser Lys Leu Pro
            20

<210> SEQ ID NO 3
<211> LENGTH: 38
<212> TYPE: PRT
<213> ORGANISM: Homo sapiens
<220> FEATURE:
<221> NAME/KEY: MISC_FEATURE
```

-continued

```
<222> LOCATION: (1)..(1)
<223> OTHER INFORMATION: Wherein the amino acid located at 1 is a
      hydrophobic amino acid, including V, L, I, M, P, F, and A
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (8)..(10)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(17)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (26)..(27)
<223> OTHER INFORMATION: Xaa can be any naturally occurring amino acid
<220> FEATURE:
<221> NAME/KEY: MISC_FEATURE
<222> LOCATION: (29)..(30)
<223> OTHER INFORMATION: Xaa can be any naturally occurring amino acid
<220> FEATURE:
<221> NAME/KEY: MISC_FEATURE
<222> LOCATION: (33)..(33)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: Xaa can be any naturally occurring amino acid
<220> FEATURE:
<221> NAME/KEY: MISC_FEATURE
<222> LOCATION: (37)..(38)
<223> OTHER INFORMATION: Xaa can be any naturally occurring amino acid

<400> SEQUENCE: 3

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35

<210> SEQ ID NO 4
<211> LENGTH: 39
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Where the amino acids located at 1 and 2 are
      hydrophobic amino acids, including V, L, I, M, P, F, and A
<220> FEATURE:
<221> NAME/KEY: MISC_FEATURE
<222> LOCATION: (3)..(3)
<223> OTHER INFORMATION: Xaa can be any naturally ocurring amino acid
<220> FEATURE:
<221> NAME/KEY: MISC_FEATURE
<222> LOCATION: (6)..(6)
<223> OTHER INFORMATION: Xaa can be any naturally ocurring amino acid
<220> FEATURE:
<221> NAME/KEY: MISC_FEATURE
```

-continued

```
<222> LOCATION: (9)..(11)
<223> OTHER INFORMATION: Xaa can be any naturally ocurring amino acid
<220> FEATURE:
<221> NAME/KEY: MISC_FEATURE
<222> LOCATION: (14)..(15)
<223> OTHER INFORMATION: Xaa can be any naturally ocurring amino acid
<220> FEATURE:
<221> NAME/KEY: MISC_FEATURE
<222> LOCATION: (17)..(18)
<223> OTHER INFORMATION: Xaa can be any naturally ocurring amino acid
<220> FEATURE:
<221> NAME/KEY: MISC_FEATURE
<222> LOCATION: (23)..(23)
<223> OTHER INFORMATION: Xaa can be any naturally ocurring amino acid
<220> FEATURE:
<221> NAME/KEY: MISC_FEATURE
<222> LOCATION: (27)..(28)
<223> OTHER INFORMATION: Xaa can be any naturally ocurring amino acid
<220> FEATURE:
<221> NAME/KEY: MISC_FEATURE
<222> LOCATION: (30)..(31)
<223> OTHER INFORMATION: Xaa can be any naturally ocurring amino acid
<220> FEATURE:
<221> NAME/KEY: MISC_FEATURE
<222> LOCATION: (34)..(34)
<223> OTHER INFORMATION: Xaa can be any naturally ocurring amino acid
<220> FEATURE:
<221> NAME/KEY: MISC_FEATURE
<222> LOCATION: (36)..(36)
<223> OTHER INFORMATION: Xaa can be any naturally ocurring amino acid
<220> FEATURE:
<221> NAME/KEY: MISC_FEATURE
<222> LOCATION: (38)..(39)
<223> OTHER INFORMATION: Xaa can be any naturally ocurring amino acid

<400> SEQUENCE: 4

Xaa Xaa Xaa Cys Glu Xaa Cys Glu Xaa Xaa Xaa Lys Glu Xaa Xaa Lys
1               5                   10                  15

Xaa Xaa Asp Asn Asn Lys Xaa Glu Lys Glu Xaa Xaa Asp Xaa Xaa Asp
            20                  25                  30

Lys Xaa Cys Xaa Lys Xaa Xaa
        35

<210> SEQ ID NO 5
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Where the amino acid located at 1 is a
      hydrophobic amino acid, including V, L, I, M, P, F, and A
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (8)..(10)
<223> OTHER INFORMATION: Xaa can be any naturally occurring amino acid
<220> FEATURE:
<221> NAME/KEY: MISC_FEATURE
<222> LOCATION: (13)..(14)
<223> OTHER INFORMATION: Xaa can be any naturally occurring amino acid
<220> FEATURE:
<221> NAME/KEY: MISC_FEATURE
<222> LOCATION: (16)..(17)
<223> OTHER INFORMATION: Xaa can be any naturally occurring amino acid
<220> FEATURE:
<221> NAME/KEY: MISC_FEATURE
<222> LOCATION: (22)..(22)
```

```
<223> OTHER INFORMATION: Xaa can be any naturally occurring amino acid
<220> FEATURE:
<221> NAME/KEY: MISC_FEATURE
<222> LOCATION: (26)..(27)
<223> OTHER INFORMATION: Xaa can be any naturally occurring amino acid
<220> FEATURE:
<221> NAME/KEY: MISC_FEATURE
<222> LOCATION: (29)..(30)
<223> OTHER INFORMATION: Xaa can be any naturally occurring amino acid
<220> FEATURE:
<221> NAME/KEY: MISC_FEATURE
<222> LOCATION: (33)..(33)
<223> OTHER INFORMATION: Xaa can be any naturally occurring amino acid
<220> FEATURE:
<221> NAME/KEY: MISC_FEATURE
<222> LOCATION: (35)..(35)
<223> OTHER INFORMATION: Xaa can be any naturally occurring amino acid
<220> FEATURE:
<221> NAME/KEY: MISC_FEATURE
<222> LOCATION: (37)..(38)
<223> OTHER INFORMATION: Xaa can be any naturally occurring amino acid

<400> SEQUENCE: 5

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35

<210> SEQ ID NO 6
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Where the amino acid located at 1 is a
      hydrophobic amino acid, including V, L, I, M, P, F, and A
<220> FEATURE:
<221> NAME/KEY: MISC_FEATURE
<222> LOCATION: (2)..(2)
<223> OTHER INFORMATION: Xaa can be any naturally occuring amino acid
<220> FEATURE:
<221> NAME/KEY: MISC_FEATURE
<222> LOCATION: (5)..(5)
<223> OTHER INFORMATION: Xaa can be any naturally occuring amino acid
<220> FEATURE:
<221> NAME/KEY: MISC_FEATURE
<222> LOCATION: (8)..(10)
<223> OTHER INFORMATION: Xaa can be any naturally occuring amino acid
<220> FEATURE:
<221> NAME/KEY: MISC_FEATURE
<222> LOCATION: (13)..(14)
<223> OTHER INFORMATION: Xaa can be any naturally occuring amino acid
<220> FEATURE:
<221> NAME/KEY: MISC_FEATURE
<222> LOCATION: (16)..(17)
<223> OTHER INFORMATION: Xaa can be any naturally occuring amino acid
<220> FEATURE:
<221> NAME/KEY: MISC_FEATURE
<222> LOCATION: (20)..(20)
<223> OTHER INFORMATION: Xaa can be any naturally occuring amino acid
<220> FEATURE:
<221> NAME/KEY: MISC_FEATURE
<222> LOCATION: (22)..(22)
<223> OTHER INFORMATION: Xaa can be any naturally occuring amino acid
<220> FEATURE:
<221> NAME/KEY: MISC_FEATURE
<222> LOCATION: (26)..(27)
<223> OTHER INFORMATION: Xaa can be any naturally occuring amino acid
<220> FEATURE:
<221> NAME/KEY: misc_feature
<222> LOCATION: (29)..(30)
<223> OTHER INFORMATION: Xaa can be any naturally occuring amino acid
```

```
<220> FEATURE:
<221> NAME/KEY: MISC_FEATURE
<222> LOCATION: (33)..(33)
<223> OTHER INFORMATION: Xaa can be any naturally occuring amino acid
<220> FEATURE:
<221> NAME/KEY: MISC_FEATURE
<222> LOCATION: (35)..(35)
<223> OTHER INFORMATION: Xaa can be any naturally occuring amino acid
<220> FEATURE:
<221> NAME/KEY: MISC_FEATURE
<222> LOCATION: (37)..(38)
<223> OTHER INFORMATION: Xaa can be any naturally occuring amino acid

<400> SEQUENCE: 6

Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35

<210> SEQ ID NO 7
<211> LENGTH: 22
<212> TYPE: PRT
<213> ORGANISM: Homo sapiens

<400> SEQUENCE: 7

Cys Gln Phe Val Met Asn Lys Phe Ser Glu Leu Ile Val Asn Asn Ala
1               5                   10                  15

Thr Glu Glu Leu Leu Tyr
            20

<210> SEQ ID NO 8
<211> LENGTH: 21
<212> TYPE: PRT
<213> ORGANISM: Homo sapiens

<400> SEQUENCE: 8

Cys Gln Leu Val Asn Arg Lys Leu Ser Glu Leu Ile Ile Asn Asn Ala
1               5                   10                  15

Thr Glu Glu Leu Leu
            20

<210> SEQ ID NO 9
<211> LENGTH: 22
<212> TYPE: PRT
<213> ORGANISM: Homo sapiens

<400> SEQUENCE: 9

Cys Glu Tyr Val Val Lys Lys Val Met Leu Leu Ile Asp Asn Asn Arg
1               5                   10                  15

Thr Glu Glu Lys Ile Ile
            20

<210> SEQ ID NO 10
<211> LENGTH: 22
<212> TYPE: PRT
<213> ORGANISM: Homo sapiens

<400> SEQUENCE: 10

Cys Glu Phe Val Val Lys Glu Val Ala Lys Leu Ile Asp Asn Asn Arg
1               5                   10                  15

Thr Glu Glu Glu Ile Leu
            20
```

<210> SEQ ID NO 11
<211> LENGTH: 22
<212> TYPE: PRT
<213> ORGANISM: Homo sapiens
<220> FEATURE:
<221> NAME/KEY: MISC_FEATURE
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (6)..(10)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (19)..(20)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa can be any naturally occurring amino acid

<400> SEQUENCE: 11

Cys Xaa Xaa Xaa Val Xaa Xaa Xaa Xaa Leu Ile Xaa Asn Asn Xaa
1               5                   10                  15

Thr Glu Xaa Xaa Xaa Xaa
            20

<210> SEQ ID NO 12
<211> LENGTH: 22
<212> TYPE: PRT
<213> ORGANISM: Homo sapiens

<400> SEQUENCE: 12

Cys Lys Asp Val Val Thr Ala Ala Gly Asp Met Leu Lys Asp Asn Ala
1               5                   10                  15

Thr Glu Glu Glu Ile Leu
            20

<210> SEQ ID NO 13
<211> LENGTH: 523
<212> TYPE: PRT
<213> ORGANISM: Homo sapiens

<400> SEQUENCE: 13

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

```
Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Gly Asp Val Cys Gln Asp Cys Ile Gln Met Val Thr Asp Ile Gln
        195                 200                 205

Thr Ala Val Arg Thr Asn Ser Thr Phe Val Gln Ala Leu Val Glu His
    210                 215                 220

Val Lys Glu Glu Cys Asp Arg Leu Gly Pro Gly Met Ala Asp Ile Cys
225                 230                 235                 240

Lys Asn Tyr Ile Ser Gln Tyr Ser Glu Ile Ala Ile Gln Met Met Met
                245                 250                 255

His Met Gln Pro Lys Glu Ile Cys Ala Leu Val Gly Phe Cys Asp Glu
            260                 265                 270

Val Lys Glu Met Pro Met Gln Thr Leu Val Pro Ala Lys Val Ala Ser
        275                 280                 285

Lys Asn Val Ile Pro Ala Leu Asp Leu Val Asp Pro Ile Lys Lys His
    290                 295                 300

Glu Val Pro Ala Lys Ser Asp Val Tyr Cys Glu Val Cys Glu Phe Leu
305                 310                 315                 320

Val Lys Glu Val Thr Lys Leu Ile Asp Asn Asn Lys Thr Glu Lys Glu
                325                 330                 335

Ile Leu Asp Ala Phe Asp Lys Met Cys Ser Lys Leu Pro Lys Ser Leu
            340                 345                 350

Ser Glu Glu Cys Gln Glu Val Val Asp Thr Tyr Gly Ser Ser Ile Leu
        355                 360                 365

Ser Ile Leu Leu Glu Glu Val Ser Pro Glu Leu Val Cys Ser Met Leu
    370                 375                 380

His Leu Cys Ser Gly Thr Arg Leu Pro Ala Leu Thr Val His Val Thr
385                 390                 395                 400

Gln Pro Lys Asp Gly Gly Phe Cys Glu Val Cys Lys Lys Leu Val Gly
                405                 410                 415

Thr Leu Asp Arg Asn Leu Glu Lys Asn Ser Thr Lys Gln Glu Ile Leu
            420                 425                 430

Ala Ala Leu Glu Lys Gly Cys Ser Phe Leu Pro Asp Pro Tyr Gln Lys
        435                 440                 445

Gln Cys Asp Gln Phe Val Ala Glu Tyr Glu Pro Val Leu Ile Glu Ile
    450                 455                 460

Leu Val Glu Val Met Asp Pro Ser Phe Val Cys Leu Lys Ile Gly Ala
465                 470                 475                 480

Cys Pro Ser Ala His Lys Pro Leu Leu Gly Thr Glu Lys Cys Ile Trp
                485                 490                 495
```

```
Gly Pro Ser Tyr Trp Cys Gln Asn Thr Glu Thr Ala Ala Gln Cys Asn
            500                 505                 510

Ala Val Glu His Cys Lys Arg His Val Trp Asn
        515                 520

<210> SEQ ID NO 14
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (2)..(2)
<223> OTHER INFORMATION: where the uncharged polar amino acids include
      T, S, Y, G, Q, and N, and mixtures thereof
<220> FEATURE:
<221> NAME/KEY: MISC_FEATURE
<222> LOCATION: (5)..(5)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (8)..(10)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (13)..(13)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (14)..(14)
<223> OTHER INFORMATION: where the uncharged polar amino acids include
      T, S, Y, G, Q, and N, and mixtures thereof
<220> FEATURE:
<221> NAME/KEY: MISC_FEATURE
<222> LOCATION: (16)..(17)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (22)..(22)
<223> OTHER INFORMATION: where the uncharged polar amino acids include
      T, S, Y, G, Q, and N, and mixtures thereof
<220> FEATURE:
<221> NAME/KEY: MISC_FEATURE
<222> LOCATION: (26)..(27)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (29)..(30)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (33)..(33)
<223> OTHER INFORMATION: where the amino acids are hydrophobic amino
      acids, including V, L, I, M, P, F, and A
<220> FEATURE:
<221> NAME/KEY: MISC_FEATURE
<222> LOCATION: (35)..(35)
<223> OTHER INFORMATION: where the amino acids are uncharged polar amino
      acids, including T, S, Y, G, Q, and N, and mixtures thereof
<220> FEATURE:
<221> NAME/KEY: MISC_FEATURE
<222> LOCATION: (37)..(38)
<223> OTHER INFORMATION: where the amino acids are hydrophobic amino
      acids, including V, L, I, M, P, F, and A

<400> SEQUENCE: 14
```

```
Xaa Xaa Cys Glu Xaa Cys Glu Xaa Xaa Xaa Lys Glu Xaa Xaa Lys Xaa
1               5                   10                  15

Xaa Asp Asn Asn Lys Xaa Glu Lys Glu Xaa Xaa Asp Xaa Xaa Asp Lys
            20                  25                  30

Xaa Cys Xaa Lys Xaa Xaa
        35

<210> SEQ ID NO 15
<211> LENGTH: 17
<212> TYPE: PRT
<213> ORGANISM: Homo sapiens

<400> SEQUENCE: 15

Tyr Cys Glu Val Cys Glu Phe Leu Val Lys Glu Val Thr Lys Leu Ile
1               5                   10                  15

Asp

<210> SEQ ID NO 16
<211> LENGTH: 17
<212> TYPE: PRT
<213> ORGANISM: Homo sapiens

<400> SEQUENCE: 16

Glu Lys Glu Ile Leu Asp Ala Phe Asp Lys Met Cys Ser Lys Leu Pro
1               5                   10                  15

Lys

<210> SEQ ID NO 17
<211> LENGTH: 80
<212> TYPE: PRT
<213> ORGANISM: Homo sapiens

<400> SEQUENCE: 17

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
            35                  40                  45

Glu Val Val Asp Thr Tyr Gly Ser Ser Ile Leu Ser Ile Leu Leu Glu
            50                  55                  60

Glu Val Ser Pro Glu Leu Val Cys Ser Met Leu His Leu Cys Ser Gly
65                  70                  75                  80

<210> SEQ ID NO 18
<211> LENGTH: 22
<212> TYPE: PRT
<213> ORGANISM: Homo sapiens

<400> SEQUENCE: 18

Cys Glu Phe Leu Val Lys Glu Val Thr Lys Leu Ile Asp Asn Asn Lys
1               5                   10                  15

Thr Glu Lys Glu Ile Leu
            20
```